United States Patent
Wang et al.

(10) Patent No.: US 11,352,363 B1
(45) Date of Patent: Jun. 7, 2022

(54) SPIROPYRROLIDINE DERIVED ANTIVIRAL AGENTS

(71) Applicant: Enanta Pharmaceuticals, Inc., Watertown, MA (US)

(72) Inventors: Guoqiang Wang, Belmont, MA (US); Xuri Gao, Newtonville, MA (US); Ruichao Shen, Belmont, MA (US); Yong He, Lexington, MA (US); Jiajun Zhang, Cambridge, MA (US); Joseph D. Panarese, Newton, MA (US); Hui Cao, Belmont, MA (US); Xuechao Xing, Wilmington, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 17/479,530

(22) Filed: Sep. 20, 2021

Related U.S. Application Data

(60) Provisional application No. 63/117,170, filed on Nov. 23, 2020, provisional application No. 63/142,663, filed on Jan. 28, 2021.

(51) Int. Cl.
  *C07D 487/10* (2006.01)
  *A61P 31/14* (2006.01)

(52) U.S. Cl.
  CPC ............ *C07D 487/10* (2013.01); *A61P 31/14* (2018.01)

(58) Field of Classification Search
  CPC ................................. C07D 487/10; A61P 31/14
  See application file for complete search history.

(56) References Cited

U.S. PATENT DOCUMENTS

| | | | |
|---|---|---|---|
| 9,290,757 B2 | 3/2016 | Madison | |
| 9,328,147 B2 | 3/2016 | Wu et al. | |
| 9,309,284 B2 | 4/2016 | Chang et al. | |
| 9,347,044 B2 | 5/2016 | Brown et al. | |
| 9,428,739 B2 | 8/2016 | Coit et al. | |
| 9,447,382 B2 | 9/2016 | Mack | |
| 9,474,759 B2 | 10/2016 | Chang et al. | |
| 9,512,443 B2 | 12/2016 | Richmond et al. | |
| 9,587,235 B2 | 3/2017 | Buechler et al. | |
| 9,591,858 B2 | 3/2017 | Valles et al. | |
| 9,688,978 B2 | 6/2017 | Buechler et al. | |
| 9,772,328 B2 | 9/2017 | Stein et al. | |
| 9,791,436 B2 | 10/2017 | Alexandrov et al. | |
| 9,828,342 B2 | 11/2017 | Horne et al. | |
| 9,975,885 B2 | 5/2018 | St. John et al. | |
| 10,017,463 B2 | 7/2018 | Hedstrom et al. | |
| 10,023,879 B2 | 7/2018 | Flynn et al. | |
| 10,093,915 B2 | 10/2018 | Wu et al. | |
| 10,130,701 B2 | 11/2018 | Bickerton et al. | |
| 10,196,444 B2 | 2/2019 | Jarjour et al. | |
| 10,221,396 B2 | 3/2019 | Brown et al. | |
| 10,260,048 B2 | 4/2019 | Mack | |
| 10,383,929 B2 | 8/2019 | Morgan et al. | |
| 10,428,142 B2 | 10/2019 | Jarjour et al. | |
| 10,457,731 B2 | 10/2019 | Jarjour et al. | |
| 10,472,618 B2 | 11/2019 | Wu et al. | |
| 10,479,975 B2 | 11/2019 | Friedman | |
| 10,590,084 B2 | 3/2020 | Buckman et al. | |
| 10,624,960 B2 | 4/2020 | Morgan et al. | |
| 10,639,358 B2 | 5/2020 | Morgan et al. | |
| 10,639,359 B2 | 5/2020 | Morgan et al. | |
| 10,646,558 B2 | 5/2020 | Morgan et al. | |
| 10,711,260 B2 | 7/2020 | Wu et al. | |
| 10,774,343 B2 | 9/2020 | Morgan et al. | |
| 10,784,994 B2 | 9/2020 | Yi et al. | |
| 10,793,843 B2 | 10/2020 | Jarjour et al. | |

(Continued)

FOREIGN PATENT DOCUMENTS

| | | |
|---|---|---|
| WO | 2004101742 A3 | 6/2005 |
| WO | 2005113580 | 12/2005 |

(Continued)

OTHER PUBLICATIONS

Efremov, I. et al., "Discovery and Optimization of a Novel Spiropyrrolidine Inhibitor of B-Secretase (BACE1) through Fragment-Based Drug Design", J. Med. Chem., vol. 55, Apr. 2, 2012, 9069-9088.

Halford, B., "Pfizer unveils its oral SARS-00V-2 inhibitor—The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/99/i13, (a version appeared in 99(13)), Apr. 7, 2021, 2 pgs.

Halford, B., "Pfizer's novel COVID-19 antiviral heads to clinical trials—The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, Sep. 17, 2020, 2 pgs.

(Continued)

*Primary Examiner* — Rebecca L Anderson
(74) *Attorney, Agent, or Firm* — Edgar W. Harlan; Carolyn S. Elmore; Elmore Patent Law Group, P.C.

(57) ABSTRACT

The present invention discloses compounds of Formula (Ia), and pharmaceutically acceptable salts, thereof:

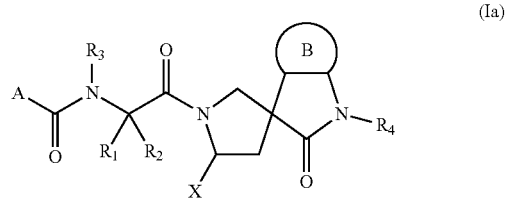

(Ia)

which inhibit coronavirus replication activity. The invention further relates to pharmaceutical compositions comprising a compound of Formula (Ia) or a pharmaceutically acceptable slat thereof, and methods of treating or preventing a coronavirus infection in a subject in need thereof, comprising administering to the subject a therapeutically effective amount of a compound of Formula (Ia) or a pharmaceutically acceptable salt thereof.

9 Claims, No Drawings

(56) References Cited

U.S. PATENT DOCUMENTS

| | | |
|---|---|---|
| 10,927,367 B2 | 2/2021 | Jarjour et al. |
| 10,934,261 B2 | 3/2021 | Buckman et al. |
| 10,934,575 B2 | 3/2021 | Grosveld et al. |
| 10,954,529 B2 | 3/2021 | Flynn et al. |
| 10,959,969 B1 | 3/2021 | Johnson |
| 10,986,848 B2 | 4/2021 | Holz-Schietinger et al. |
| 11,013,779 B2 | 5/2021 | Chang et al. |
| 11,020,466 B2 | 6/2021 | Morgan et al. |
| 11,021,513 B2 | 6/2021 | Schinazi et al. |
| 11,033,600 B2 | 6/2021 | Chang et al. |
| 11,045,546 B1 | 6/2021 | Kelly et al. |
| 11,058,763 B2 | 7/2021 | Zhang et al. |
| 11,058,779 B2 | 7/2021 | Lu et al. |
| 11,072,787 B2 | 7/2021 | Wu et al. |
| 11,124,497 B1 | 9/2021 | Arnold et al. |
| 11,174,231 B1 | 11/2021 | Arnold et al. |
| 11,207,370 B2 | 12/2021 | Schinazi et al. |
| 2005/0143320 A1 | 6/2005 | Yang et al. |
| 2006/0014821 A1 | 1/2006 | He et al. |
| 2009/0137818 A1 | 5/2009 | Hilgenfeld et al. |
| 2014/0243341 A1 | 8/2014 | Chang et al. |
| 2021/0355111 A1 | 11/2021 | Arnold et al. |

FOREIGN PATENT DOCUMENTS

| | | |
|---|---|---|
| WO | 2006061714 | 8/2006 |
| WO | 2012099454 A1 | 7/2012 |
| WO | 2013049382 A3 | 5/2013 |
| WO | 2013166319 A1 | 11/2013 |
| WO | 2018042343 A2 | 3/2018 |
| WO | 2021205296 A1 | 10/2021 |
| WO | 2021206876 A1 | 10/2021 |
| WO | 2021206877 A1 | 10/2021 |
| WO | 2021207409 A2 | 10/2021 |
| WO | 2021226546 A1 | 11/2021 |
| WO | 2021250648 A1 | 12/2021 |
| WO | 2021252491 A1 | 12/2021 |
| WO | 2022020711 A1 | 1/2022 |

OTHER PUBLICATIONS

Xu, J. et al., "Green Oxidation of Indoles Using Halide Catalysis", Nature Communications, 10:4754, https://doi.org/10.1038/s41467-019-12768-4, Oct. 18, 2019, 1-11.

Konno, S., et al. "3CL Protease Inhibitors with an Electrophilic Arylketone Moiety as Anti-SARS-CoV-2 Agents," J. Medicinal Chemistry, https://doi.org/10.1021/acs.jmedchem.1c00665, pp. 1-14, 2021.

U.S. Appl. No. 17/506,981, filed Oct. 21, 2021.
U.S. Appl. No. 17/379,409, filed Jul. 19, 2021.
U.S. Appl. No. 17/479,244, filed Sep. 20, 2021.
U.S. Appl. No. 17/479,669, filed Sep. 20, 2021.
U.S. Appl. No. 17/479,248, filed Sep. 20, 2021.
U.S. Appl. No. 17/479,455, filed Sep. 20, 2021.

Lee., C. et al., "Structural Basis of Inhibition Specificities of 3C and 3C-like Proteases by Zinc-coordinating and Peptidomimetic Compounds", J. Biological Chem., vol. 284, No. 12, Mar. 20, 2009, 7646-7655.

Yang, S. et al., "Synthesis, Crystal Structure, Structure-Activity Relationships, and Antiviral Activity of a Potent SARS Coronavirus 3CL Protease Inhibitor", J. Med. Chem., vol. 49, Jul. 14, 2006, 4971-4980.

PubChem, SID 367622864, May 25, 2018.

Zhou, L. et al., "An Overview of Spirooxindole as a Promising Scaffold for Novel Drug Discovery", Expert Opinion on Drug Discovery, vol. 15, Iss. 5, Feb. 2020, 603-625.

SPIROPYRROLIDINE DERIVED ANTIVIRAL AGENTS

RELATED APPLICATIONS

This application claims the benefit of U.S. Provisional Application No. 63/117,170, filed on Nov. 23, 2020 and U.S. Provisional Application No. 63/142,663, filed on Jan. 28, 2021. The entire teachings of the above applications are incorporated herein by reference.

TECHNICAL FIELD

The invention relates to compounds and methods of inhibiting coronavirus replication activity by targeting the 3C-Like protease (sometimes referred to as "3CLpro", "Main protease", or "Mpro") with a therapeutically effective amount of a 3C-Like protease inhibitor. The invention further relates to pharmaceutical compositions containing the coronavirus 3C-Like protease inhibitor in a mammal by administering effective amounts of such coronavirus 3C-Like protease inhibitor.

BACKGROUND OF THE INVENTION

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO 2004101742 A2, US 2005/0143320 A1, US 2006/0014821 A1, US 2009/0137818 A1, WO 2013/049382 A2, WO 2013/166319 A1, WO2018042343, WO2018023054, WO2005113580, and WO2006061714).

More effective therapies for coronavirus infections are needed due to this high unmet clinical need. This invention provides compounds which inhibit the coronavirus lifecycle and methods for preparation and use of these compounds. These compounds are useful for treating or preventing coronavirus infections and decreasing occurrence of disease complications such as organ failure or death.

SUMMARY OF THE INVENTION

The present invention relates to novel antiviral compounds, pharmaceutical compositions comprising such compounds, as well as methods to treat or prevent viral (particularly coronavirus) infection in a subject in need of such therapy with said compounds. Compounds of the present invention inhibit the protein(s) encoded by a coronavirus or interfere with the life cycle of a coronavirus and are also useful as antiviral agents. In addition, the present invention provides processes for the preparation of said compounds.

In certain embodiments, the present invention provides compounds represented by Formula (Ia), and pharmaceutically acceptable salts, esters and prodrugs thereof,

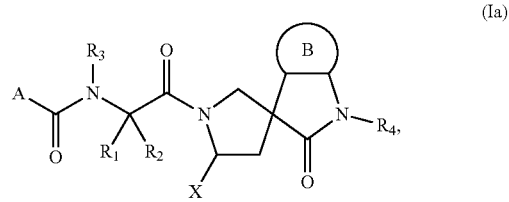

(Ia)

wherein:
A is selected from:
  1) —$R_{11}$;
  2) —$OR_{12}$; and
  3) —$NR_{13}R_{14}$;
B is an optionally substituted aryl or optionally substituted heteroaryl;
X is selected from:
  1) —CN;
  2) —C(O)$R_{15}$;
  3) —CH(OH)SO$_3$$R_{16}$;
  4) —C(O)$NR_{13}R_{14}$; and
  5) —C(O)C(O)$NR_{13}R_{14}$;
$R_1$, $R_2$, and $R_3$ are each independently selected from:
  1) Hydrogen;
  2) Optionally substituted —$C_1$-$C_8$ alkyl;
  3) Optionally substituted —$C_2$-$C_8$ alkenyl;
  4) Optionally substituted —$C_2$-$C_8$ alkynyl;
  5) Optionally substituted —$C_3$-$C_8$ cycloalkyl;
  6) Optionally substituted 3- to 8-membered heterocloalkyl;
  7) Optionally substituted aryl;
  8) Optionally substituted arylalkyl;
  9) Optionally substituted heteroaryl; and
  10) Optionally substituted heteroarylalkyl;
alternatively, $R_1$ and $R_2$ are taken together with the carbon atom to which they are attached to form an optionally substituted 3- to 8-membered carbocyclic ring or an optionally substituted 3- to 8-membered heterocyclic ring.
$R_4$ is hydrogen, optionally substituted —$C_1$-$C_4$ alkyl, optionally substituted $C_2$-$C_4$-alkenyl, or optionally substituted —$C_3$-$C_6$ cycloalkyl.
$R_{11}$ and $R_{12}$ are each independently selected from:
  1) Optionally substituted —$C_1$-$C_8$ alkyl;
  2) Optionally substituted —$C_2$-$C_8$ alkenyl;
  3) Optionally substituted —$C_2$-$C_8$ alkynyl;
  4) Optionally substituted —$C_3$-$C_8$ cycloalkyl;
  5) Optionally substituted 3- to 8-membered heterocloalkyl;
  6) Optionally substituted aryl;
  7) Optionally substituted arylalkyl;
  8) Optionally substituted heteroaryl; and
  9) Optionally substituted heteroarylalkyl;
$R_{13}$ and $R_{14}$ each independently selected from:
  1) Hydrogen;
  2) Optionally substituted —$C_1$-$C_8$ alkyl;
  3) Optionally substituted —$C_2$-$C_8$ alkenyl;
  4) Optionally substituted —$C_2$-$C_8$ alkynyl;

5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;
alternatively, $R_{13}$ and $R_{14}$ are taken together with the nitrogen atom to which they are attached to form an optionally substituted 3- to 8-membered heterocyclic ring; $R_{15}$ is hydrogen, hydroxy, or optionally substituted —$C_1$-$C_8$ alkyl; and $R_{16}$ is hydrogen or $Na^+$.

In certain embodiments, the present invention provides compounds represented by Formula (I), and pharmaceutically acceptable salts, esters and prodrugs thereof,

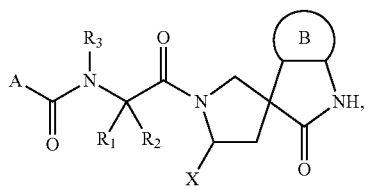
(I)

wherein:
A is selected from:
1) —$R_{11}$;
2) —$OR_{12}$; and
3) —$NR_{13}R_{14}$;
B is an optionally substituted aryl or optionally substituted heteroaryl;
X is selected from:
1) —CN;
2) —$C(O)R_{15}$;
3) —$CH(OH)SO_3R_{16}$;
4) —$C(O)NR_{13}R_{14}$; and
5) —$C(O)C(O)NR_{13}R_{14}$;
$R_1$, $R_2$, and $R_3$ are each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;
alternatively, $R_1$ and $R_2$ are taken together with the carbon atom to which they are attached to form an optionally substituted 3- to 8-membered carbocyclic ring or an optionally substituted 3- to 8-membered heterocyclic ring.
$R_{11}$ and $R_{12}$ are each independently selected from:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted 3- to 8-membered heterocycloalkyl;
6) Optionally substituted aryl;
7) Optionally substituted arylalkyl;
8) Optionally substituted heteroaryl; and
9) Optionally substituted heteroarylalkyl;

$R_{13}$ and $R_{14}$ each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;
alternatively, $R_{13}$ and $R_{14}$ are taken together with the nitrogen atom to which they are attached to form an optionally substituted 3- to 8-membered heterocyclic ring;
$R_{15}$ is hydrogen, hydroxy, or optionally substituted —$C_1$-$C_8$ alkyl; and
$R_{16}$ is hydrogen or $Na^+$.

DETAILED DESCRIPTION OF THE INVENTION

In one embodiment of the present invention is a compound of Formula (I) or Formula (Ia) as described above, or a pharmaceutically acceptable salt thereof.

In one embodiment of the present invention, the compound of Formula (Ia) is represented by Formula (Ia-A) or Formula (Ia-B), or a pharmaceutically acceptable salt, ester or prodrug thereof:

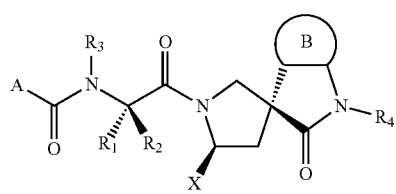
(Ia-A)

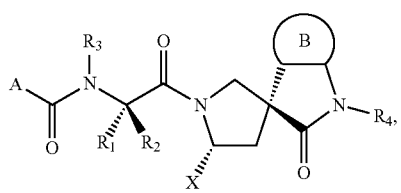
(Ia-B)

wherein A, B, X, $R_1$, $R_2$, $R_3$, and $R_4$ are as previously defined.

In a preferred embodiment, the compound of Formula (Ia) has the stereochemistry shown in Formula (Ia-A).

In one embodiment of the present invention, the compound of Formula (I) is represented by Formula (I-A) or Formula (I-B), or a pharmaceutically acceptable salt, ester or prodrug thereof:

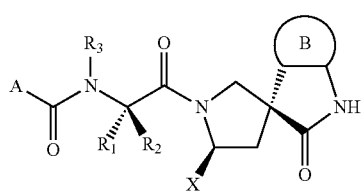
(I-A)

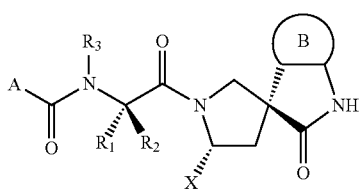

(I-B)

wherein A, B, X, $R_1$, $R_2$, and $R_3$ are as previously defined.

In a preferred embodiment, the compound of Formula (I) has the stereochemistry shown in Formula (I-A).

In certain embodiments of the compounds of Formula (I) or Formula (Ia), $R_1$ is hydrogen or optionally substituted —$C_1$-$C_4$ alkyl; optionally substituted —$C_3$-$C_6$ cycloalkyl; optionally substituted aryl; optionally substituted arylalkyl; optionally substituted heteroarylalkyl.

In certain embodiments of the compounds of Formula (I) or Formula (Ia), $R_2$ is hydrogen or optionally substituted —$C_1$-$C_4$ alkyl; optionally substituted —$C_3$-$C_6$ cycloalkyl; optionally substituted aryl; optionally substituted arylalkyl; optionally substituted heteroarylalkyl.

In certain embodiments of the compounds of Formula (I) or Formula (Ia), $R_3$ is hydrogen or optionally substituted —$C_1$-$C_4$ alkyl; $R_4$ is hydrogen or optionally substituted —$C_1$-$C_4$ alkyl.

In certain embodiments of the compounds of Formula (I) or Formula (Ia), $R_3$ is hydrogen, -Me, -Et, —Pr, -i-Pr, -allyl, —$CF_3$, -$CD_3$ or cyclopropyl.

In certain embodiments of the compounds of Formula (Ia), $R_4$ is hydrogen, -Me, -Et, —Pr, -i-Pr, -allyl, —$CF_3$ or cyclopropyl.

In certain embodiments of the compounds of Formula (I) or Formula (Ia), X is —CN.

In certain embodiments of the compounds of Formula (I) or Formula (Ia), X is —C(O)H.

In certain embodiments of the compounds of Formula (I) or Formula (Ia), X is —C(O)$CH_2$OH, —C(O)$CH_2$Cl or —C(O)$CH_2$F.

In certain embodiments of the compounds of Formula (I) or Formula (Ia), X is —C(O)C(O)N$R_{13}R_{14}$, wherein $R_{13}$ and $R_{14}$ are previously defined.

In certain embodiments of the compounds of Formula (I) or Formula (Ia), A is derived from one of the following by removal of a hydrogen atom and is optionally substituted:

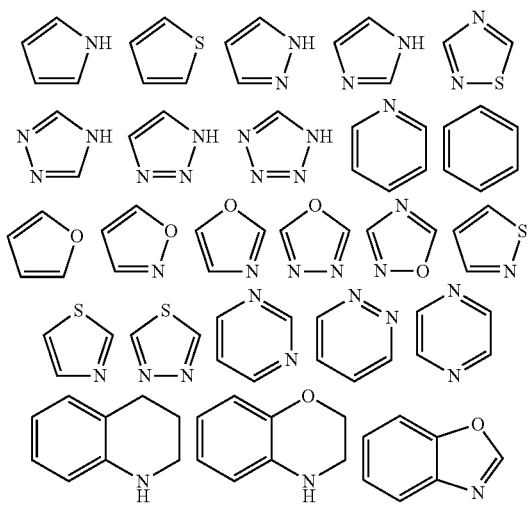

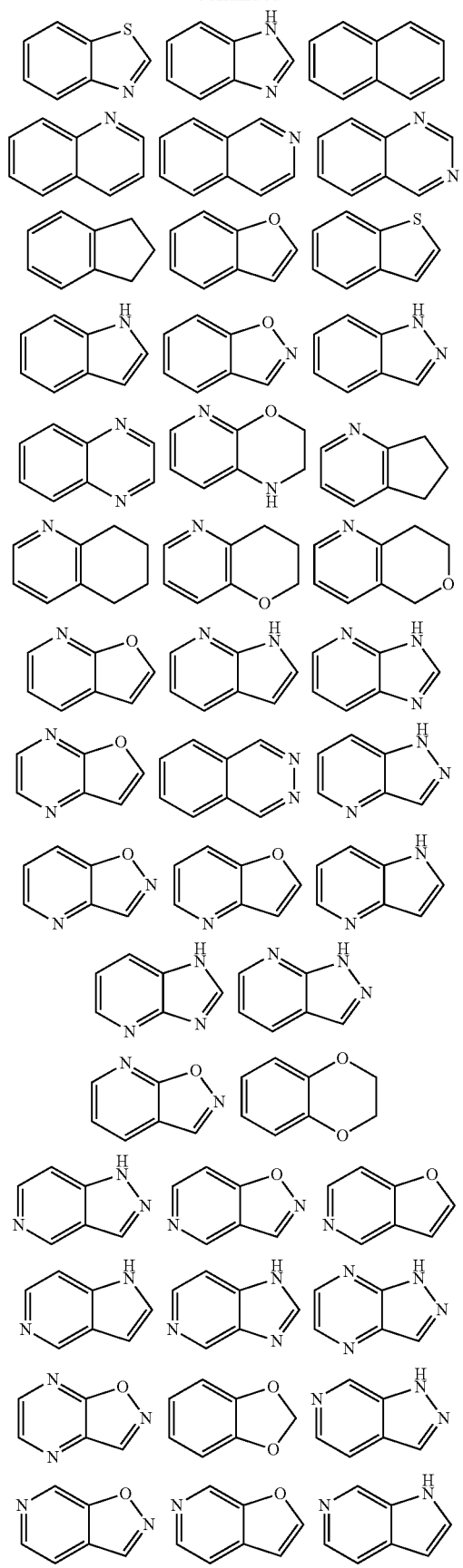

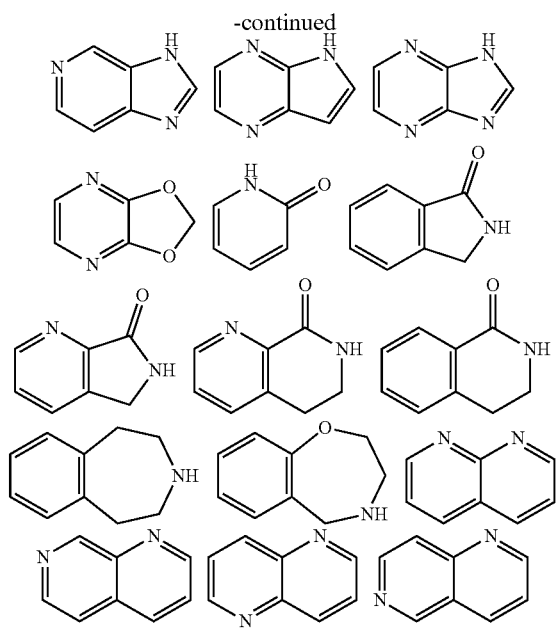

In certain embodiments of the compounds of Formula (I) or Formula (Ia), A is selected from the following groups, and A is optionally substituted:

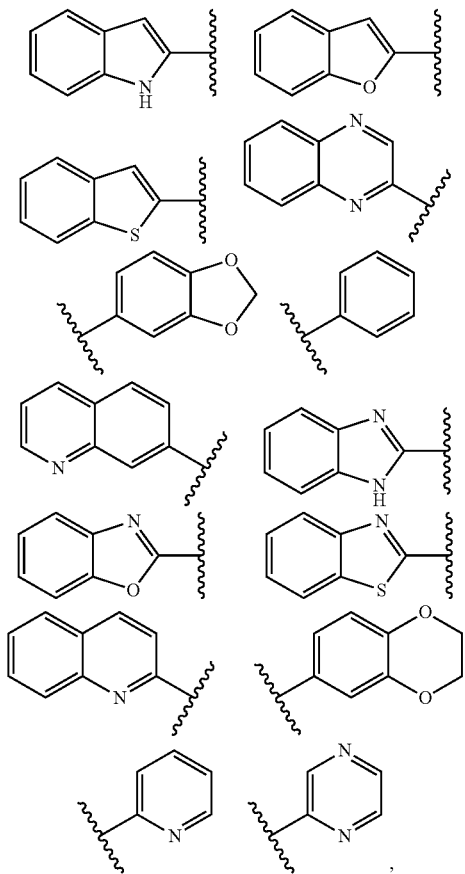

preferably the substituents are independently selected from halogen, CN, $NH_2$, optionally substituted —$C_1$-$C_3$ alkoxy, optionally substituted —$C_1$-$C_3$ alkyl, optionally substituted —$C_3$-$C_6$ cycloalkyl, optionally substituted aryl, and optionally substituted heteroaryl. Preferably the number of substituents is 0 to 3.

In certain embodiments of the compounds of Formula (I) or Formula (Ia), A is selected from the following groups, and A is optionally substituted:

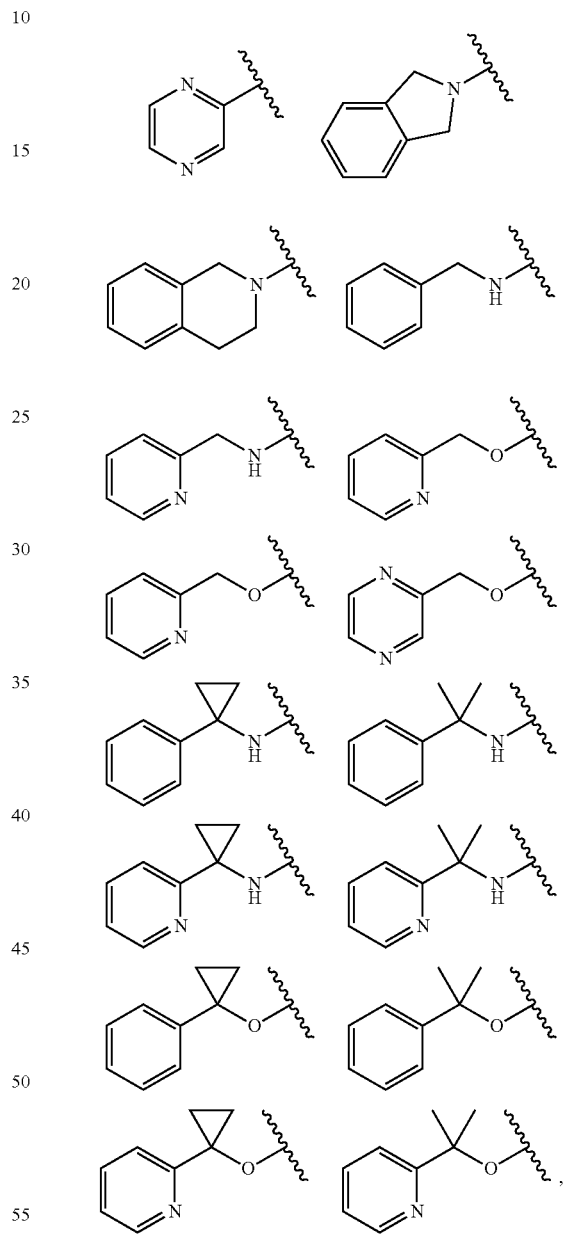

preferably the substituents are independently selected from halogen, CN, $NH_2$, optionally substituted —$C_1$-$C_3$ alkoxy, optionally substituted —$C_1$-$C_3$ alkyl, optionally substituted —$C_3$-$C_6$ cycloalkyl, optionally substituted aryl, and optionally substituted heteroaryl. Preferably the number of substituents is 0 to 3.

In certain embodiments of the compounds of Formula (I) or Formula (Ia), B is selected from the following groups, and B is optionally substituted:

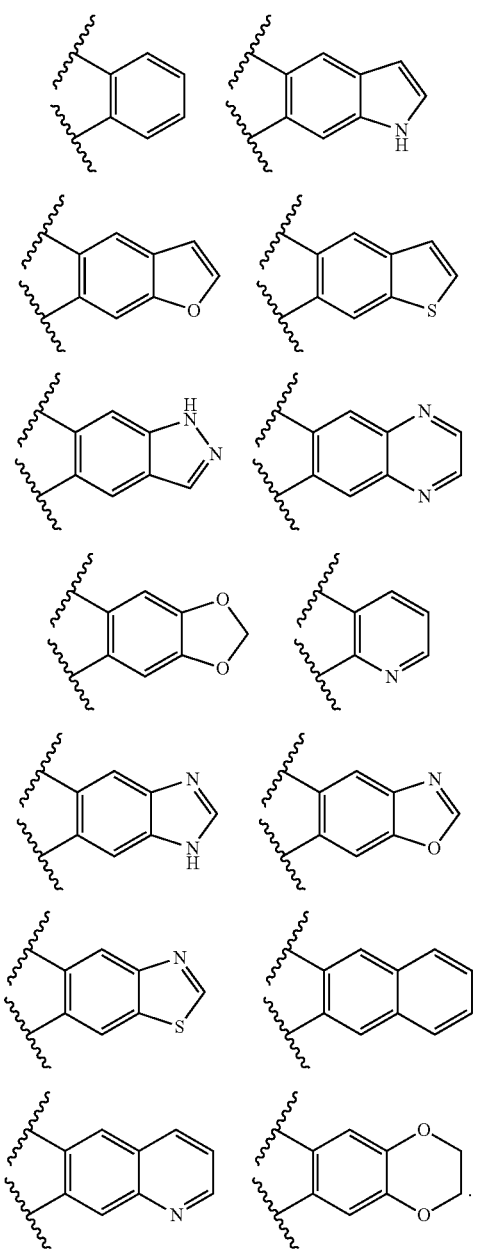

In certain embodiments, the compound of Formula (Ia), is represented by Formula (Ia-1):

(Ia-1)

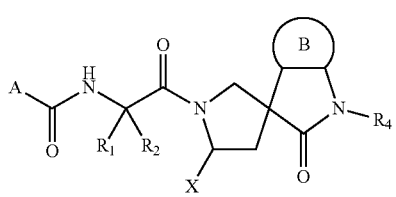

wherein A, B, $R_1$, $R_2$, $R_4$, and X are as previously defined.

In certain embodiments, the compound of Formula (Ia) is represented by Formula (Ia-2):

(Ia-2)

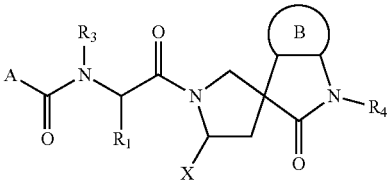

wherein A, B, $R_1$, $R_3$, $R_4$, and X are as previously defined.

In certain embodiments, the compound of Formula (Ia) is represented by Formula (Ia-3):

(Ia-3)

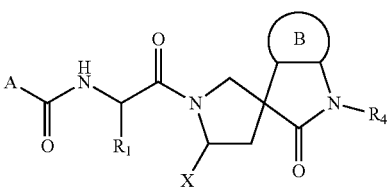

wherein A, B, $R_1$, $R_4$, and X are as previously defined.

In certain embodiments, the compound of Formula (I), is represented by Formula (I-1):

(I-1)

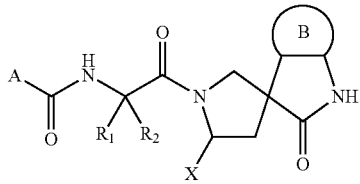

wherein A, B, $R_1$, $R_2$, and X are as previously defined.

In certain embodiments, the compound of Formula (I) is represented by Formula (I-2):

(I-2)

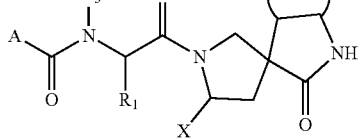

wherein A, B, $R_1$, $R_3$, and X are as previously defined.

In certain embodiments, the compound of Formula (I) is represented by Formula (I-3):

(I-3)

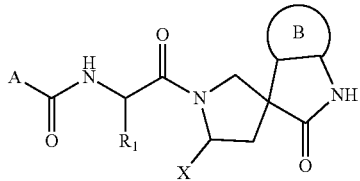

wherein A, B, $R_1$, and X are as previously defined.

In certain embodiments, the compound of Formula (Ia) is represented by Formula (IIa):

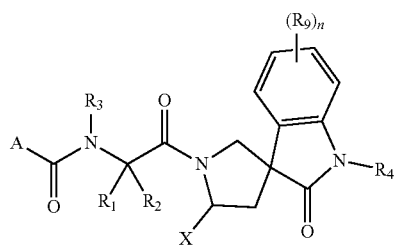

(IIa)

wherein A, $R_1$, $R_2$, $R_3$, $R_4$, and X are as previously defined and
each $R_9$ is independently selected from:
1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl; and
11) Optionally substituted heteroaryl;
and n is 0, 1, 2, 3, or 4.

In certain embodiments, the compound of Formula (I) is represented by Formula (II):

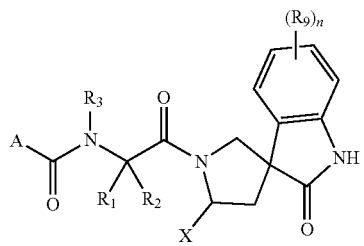

(II)

wherein A, $R_1$, $R_2$, $R_3$, and X are as previously defined and each $R_9$ is independently selected from:
1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl; and
11) Optionally substituted heteroaryl;
and n is 0, 1, 2, 3, or 4.

In certain embodiments, the compound of Formula (Ia) is represented by Formula (IIIa-1):

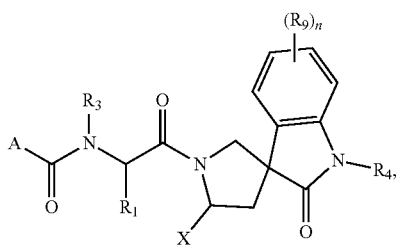

(IIIa-1)

wherein A, $R_1$, $R_3$, $R_4$, $R_9$, n and X are as previously defined.

In certain embodiments, the compound of Formula (Ia) is represented by Formula (IIIa-2):

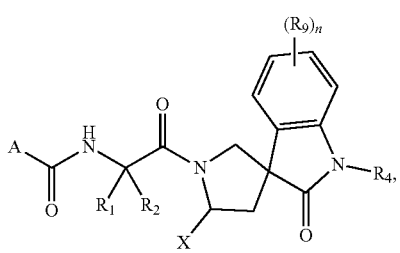

(IIIa-2)

wherein A, $R_1$, $R_2$, $R_4$, $R_9$, n and X are as previously defined.

In certain embodiments, the compound of Formula (I) is represented by Formula (III):

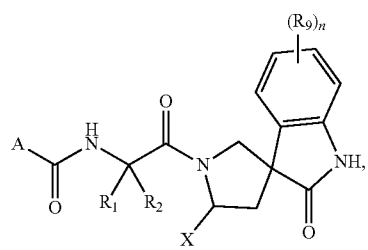

(III)

wherein A, $R_1$, $R_2$, $R_9$, n and X are as previously defined.

In certain embodiments, the compound of Formula (Ia) is represented by one of Formulae (IVa-1) to (IVa-6):

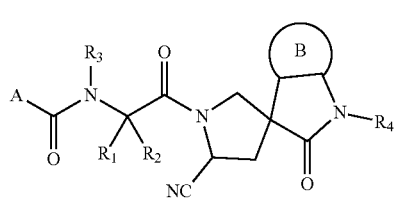

(IVa-1)

-continued
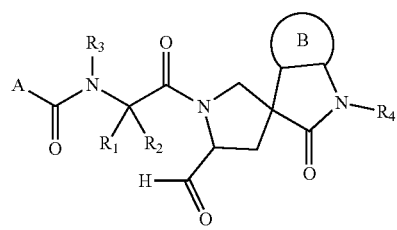
(IVa-2)
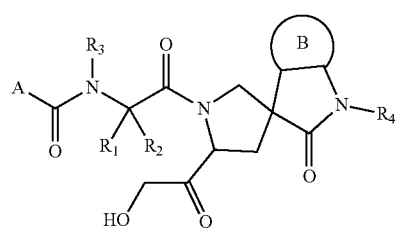
(IVa-3)
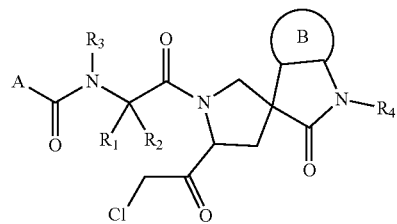
(IVa-4)
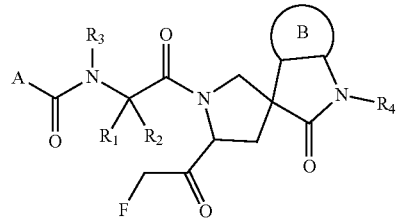
(IVa-5)
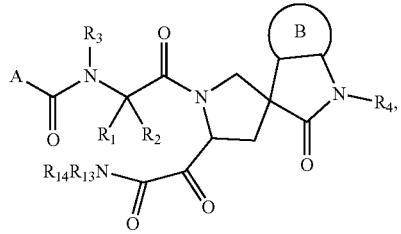
(IVa-6)
wherein A, B, $R_1$, $R_2$, $R_3$, $R_4$, $R_{13}$ and $R_{14}$ are as previously defined.
In certain embodiments, the compound of Formula (I) is represented by one of Formulae (IV-1) to (IV-6):
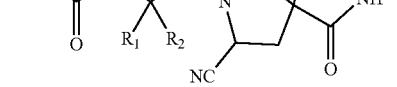
(IV-1)
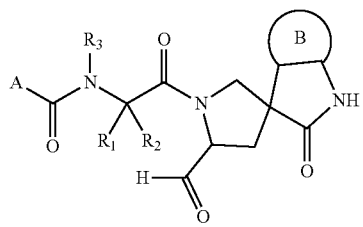
(IV-2)
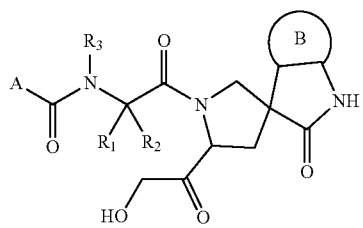
(IV-3)
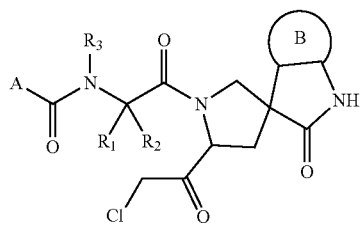
(IV-4)
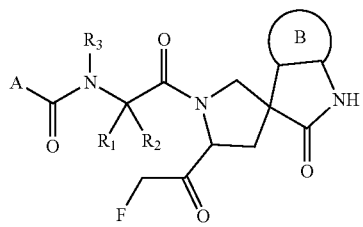
(IV-5)
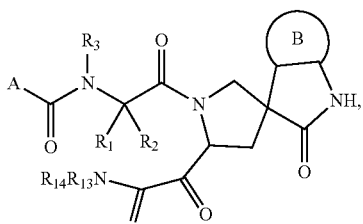
(IV-6)
wherein A, B, $R_1$, $R_2$, $R_3$, $R_{13}$ and $R_{14}$ are as previously defined.
In certain embodiments, the compound of Formula (Ia), is represented by one of Formulae (Va-1) to (Va-6):
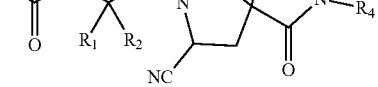
(Va-1)

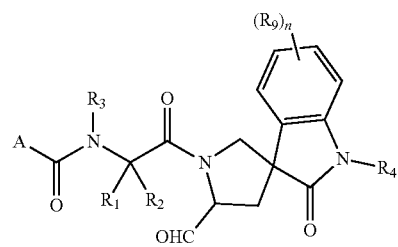
(Va-2)
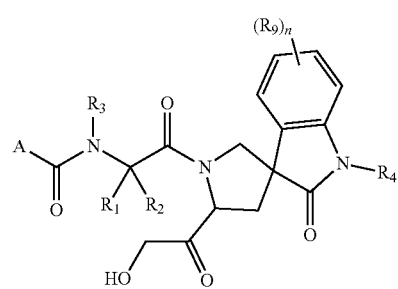
(Va-3)
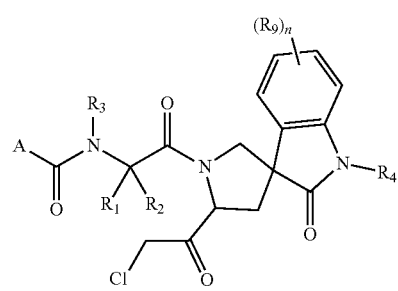
(Va-4)
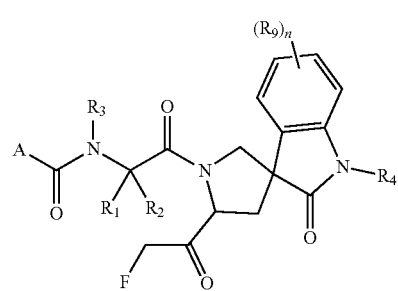
(Va-5)
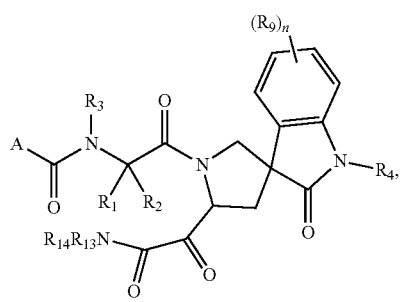
(Va-6)
wherein
A, $R_1$, $R_2$, $R_3$, $R_4$, $R_9$, $R_{13}$, $R_{14}$ and n are as previously defined.
In certain embodiments, the compound of Formula (I) is represented by one of Formulae (V-1) to (V-6):
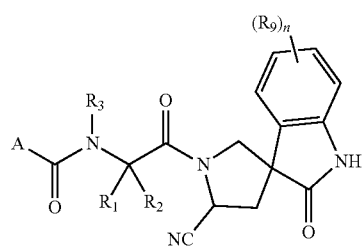
(V-1)
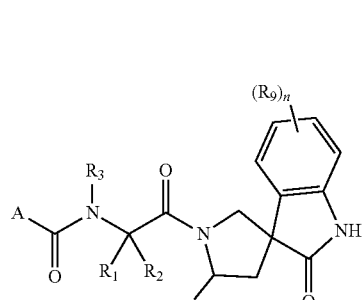
(V-2)
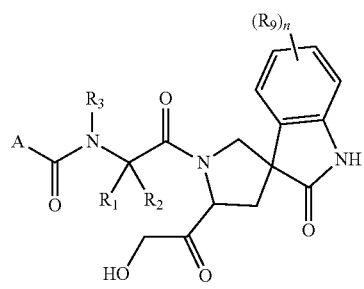
(V-3)
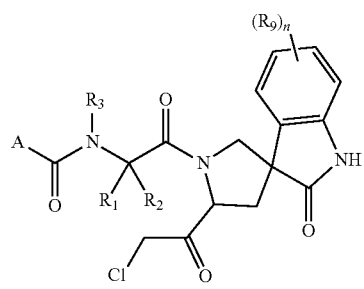
(V-4)
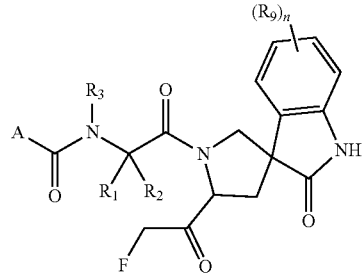
(V-5)

(V-6)
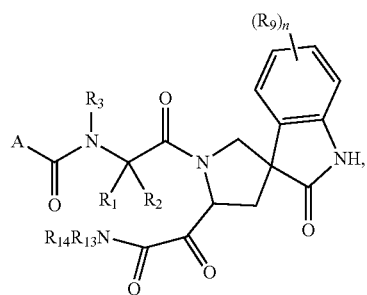
wherein A, $R_1$, $R_2$, $R_3$, $R_9$, $R_{13}$, $R_{14}$ and n are as previously defined.
In certain embodiments, the compound of Formula (Ia) is represented by one of Formulae (VIa-1) to (VIa-6):
(VIa-1)
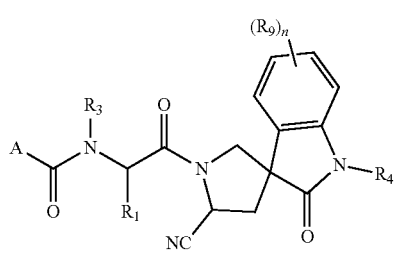
(VIa-2)
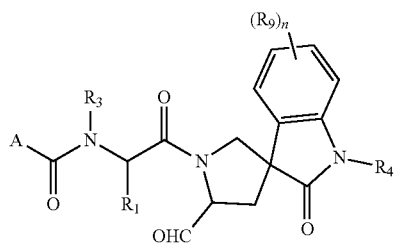
(VIa-3)
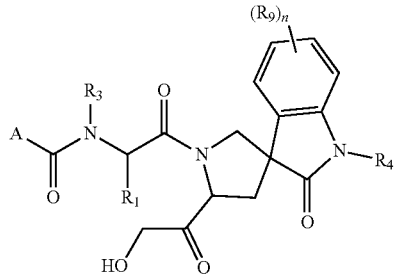
(VIa-4)
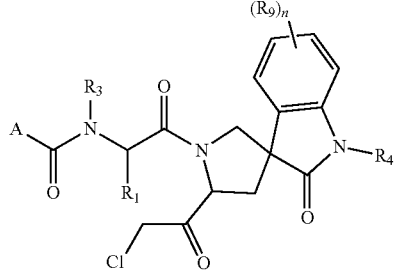
(VIa-5)
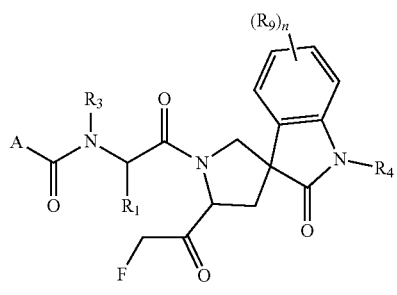
(VIa-6)
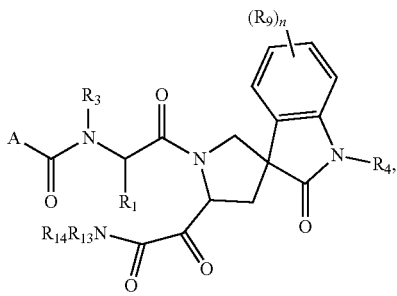
wherein A, $R_1$, $R_3$, $R_4$, $R_9$, $R_{13}$, $R_{14}$ and n are as previously defined.
In certain embodiments, the compound of Formula (I) is represented by one of Formulae (VI-1) to (VI-6):
(VI-1)
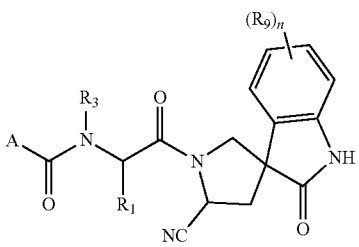
(VI-2)
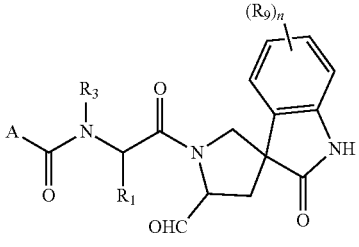
(VI-3)
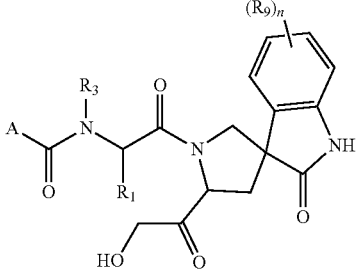

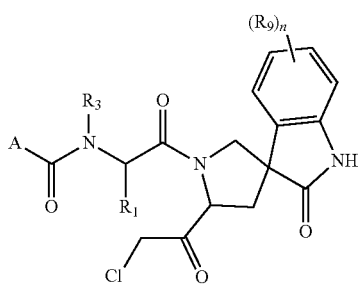
(VI-4)
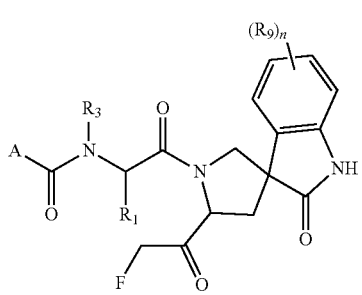
(VI-5)
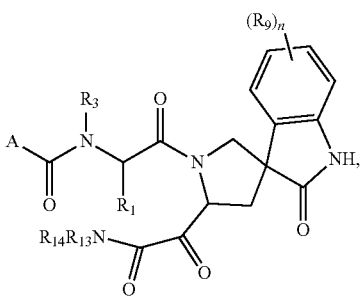
(VI-6)
wherein A, $R_1$, $R_3$, $R_9$, $R_{13}$, $R_{14}$ and n are as previously defined.
In certain embodiments, the compound of Formula (I) is represented by one of Formulae (VII-1) to (VII-5):
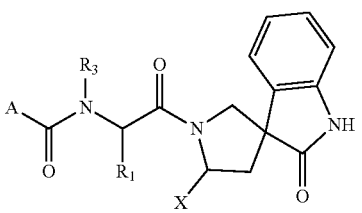
(VII-1)
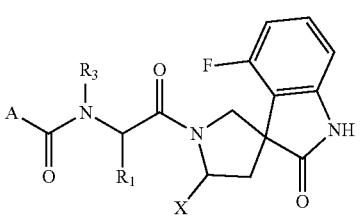
(VII-2)
(VII-3)
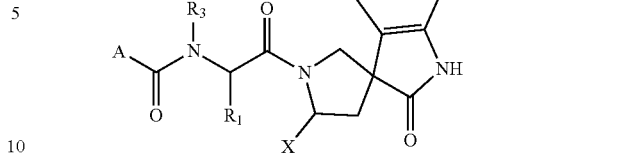
(VII-4)
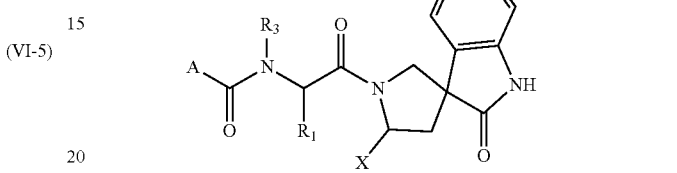
(VII-5)
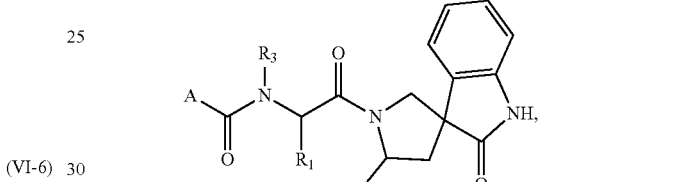
wherein A, $R_1$, $R_3$, and X are as previously defined. Preferably, A is selected from the following:
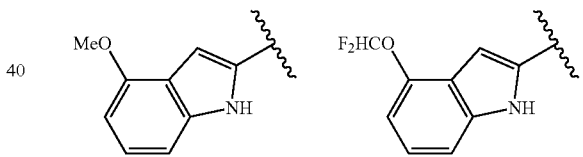
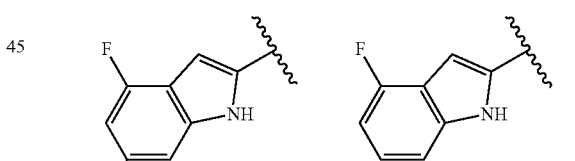
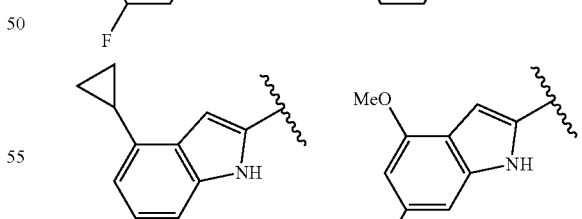
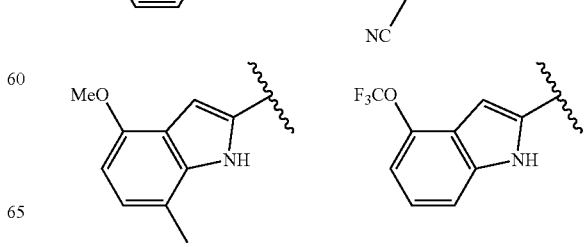

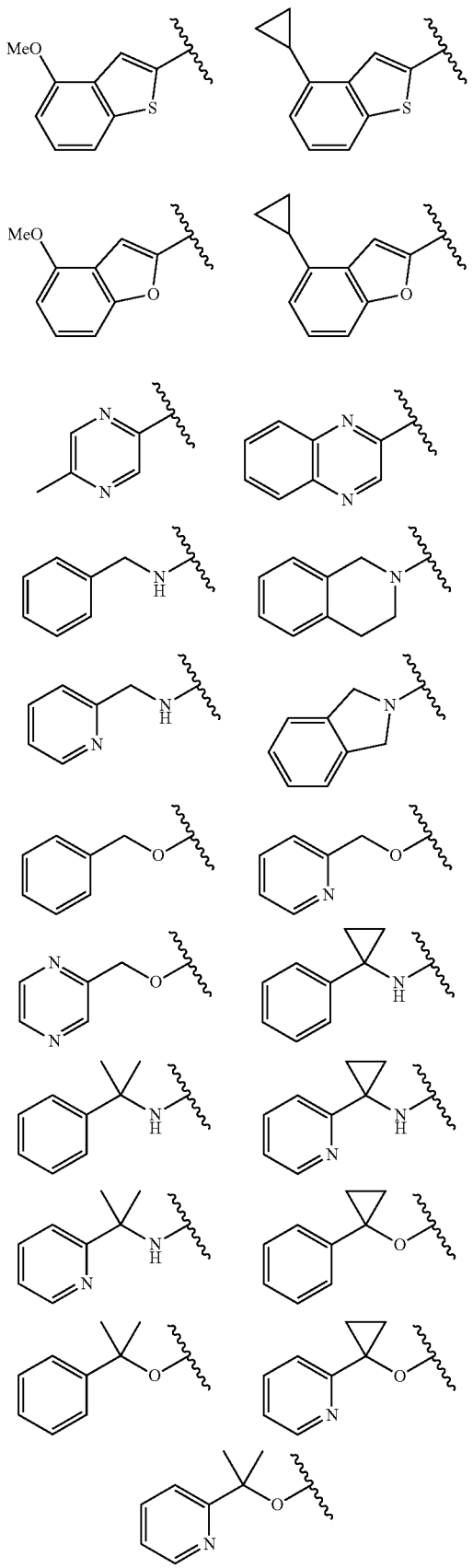
$R_1$ is selected from the following:
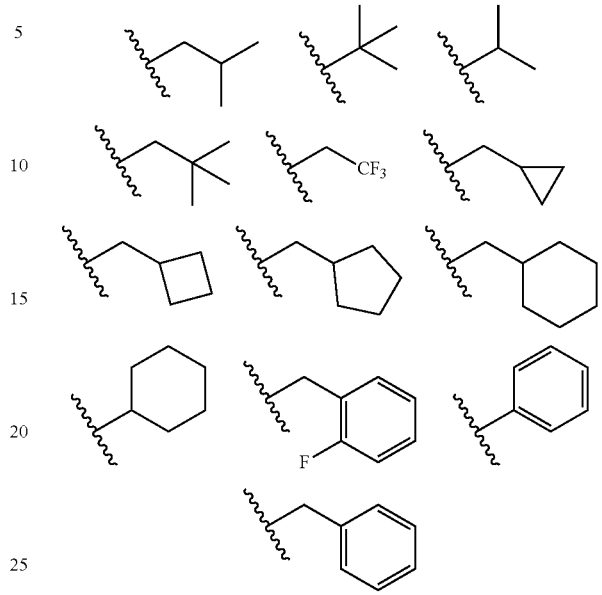
and X is selected from the following:
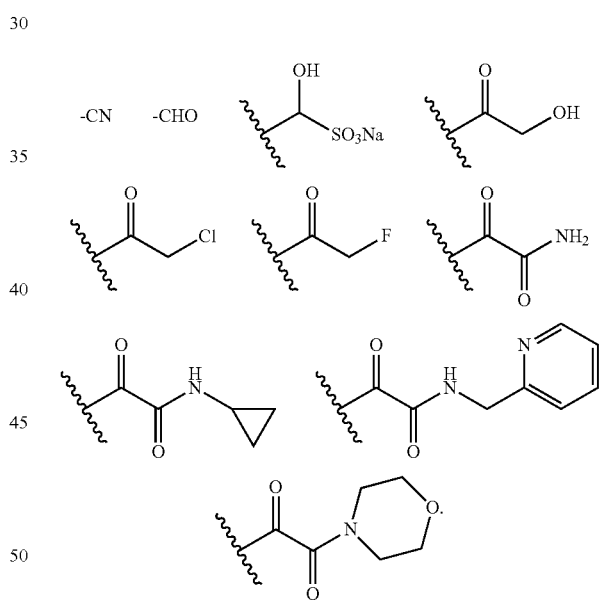
In certain embodiments, the compound of Formula (I) is represented by one of Formulae (VII-1a)~(VII-5a):
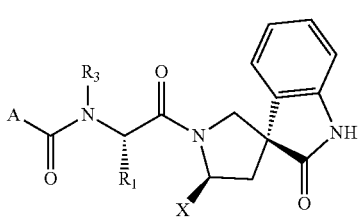
(VII-1a)

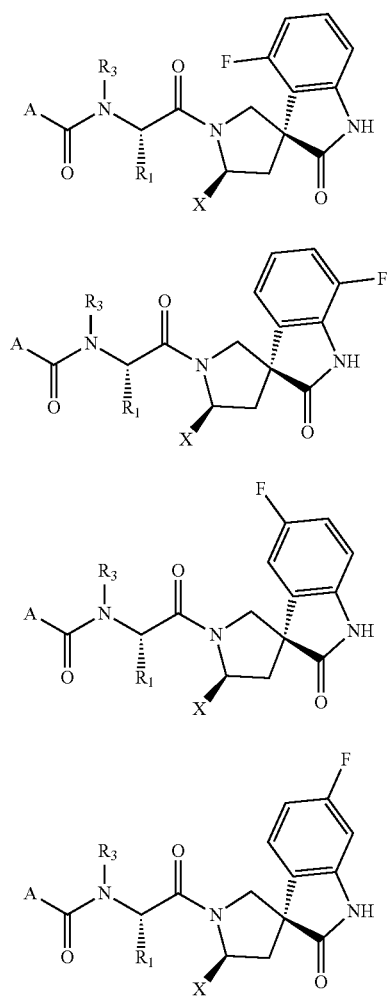
(VII-2a)
(VII-3a)
(VII-4a)
(VII-5a)
wherein A, $R_1$, $R_3$, and X are as previously defined. Preferably, A is selected from the following:
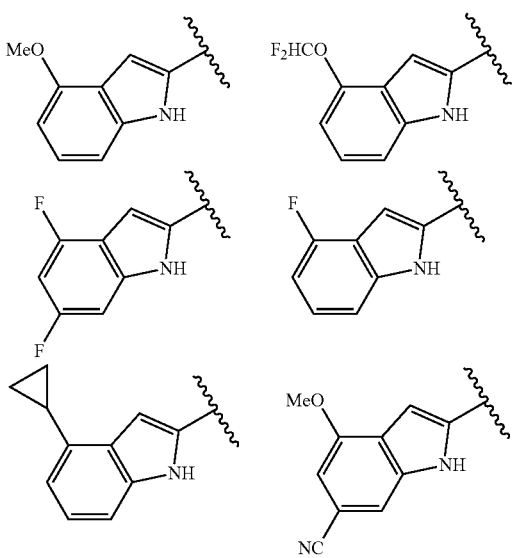
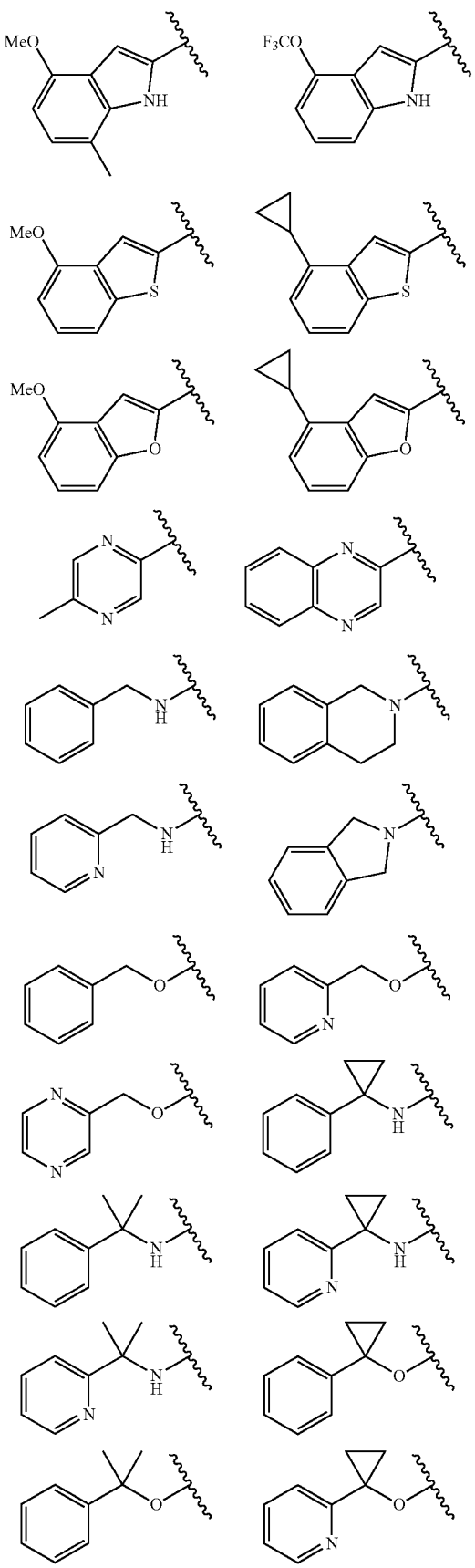

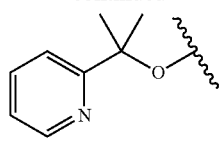
R₁ is selected from the following:
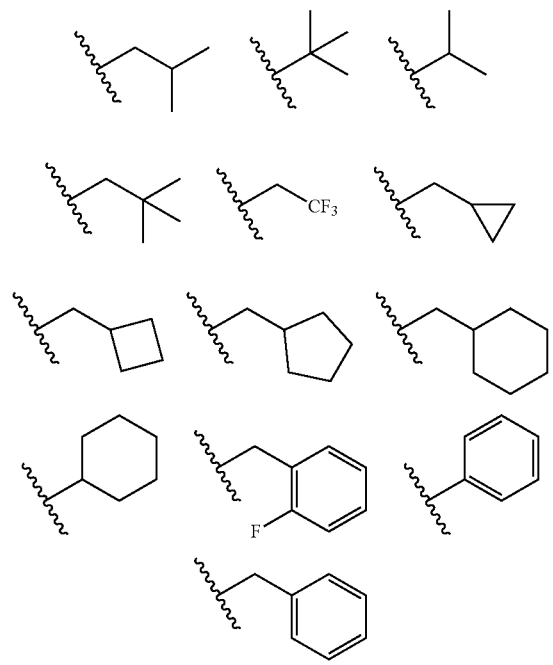
and X is selected from the following:
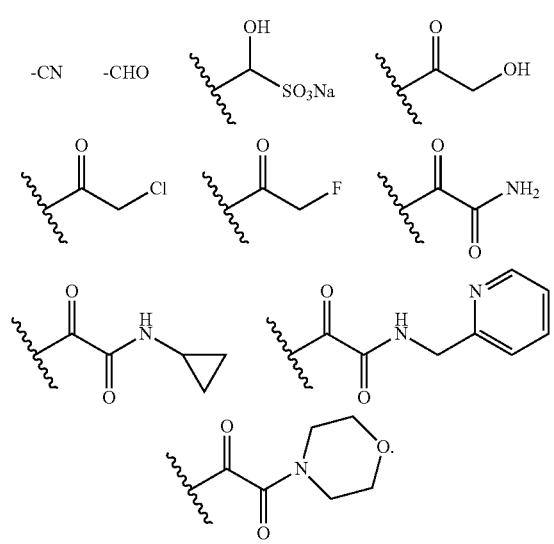
In certain embodiments, the compound of Formula (I) is represented by one of Formulae (VII-1) to (VII-5) and Formulae (VII-1a) to (VII-5a), wherein A is selected from, the following:
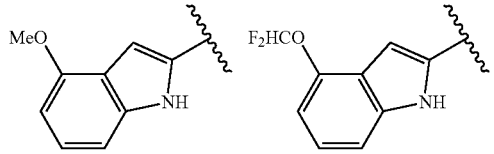
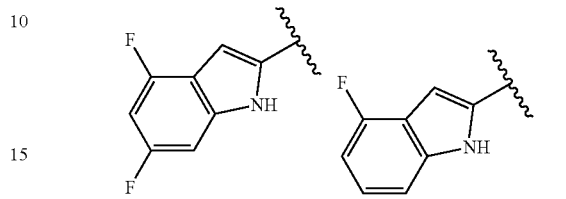
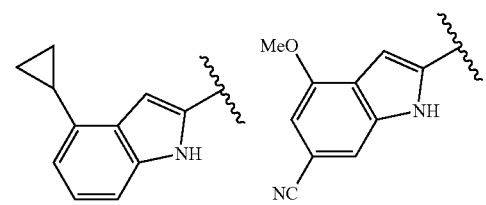
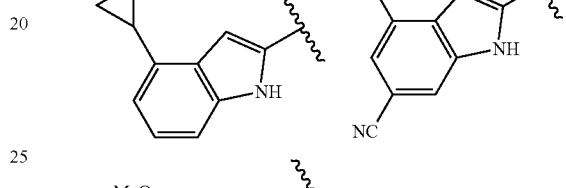
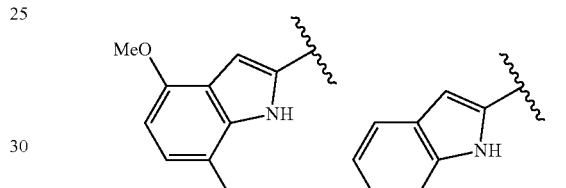
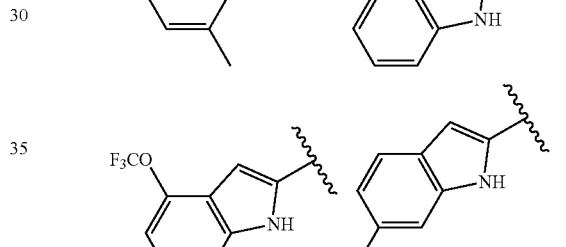
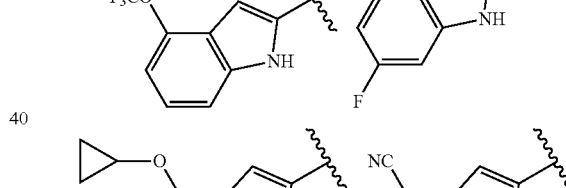
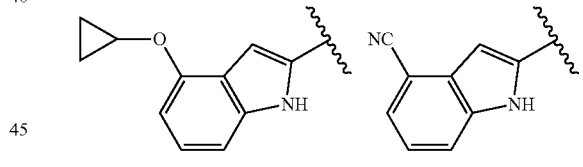
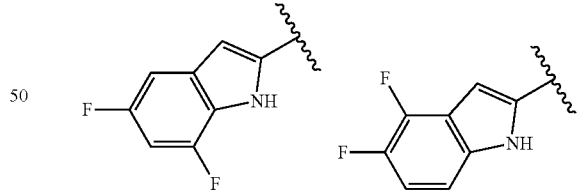
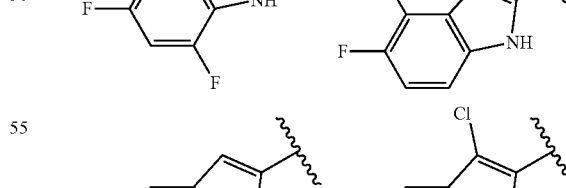
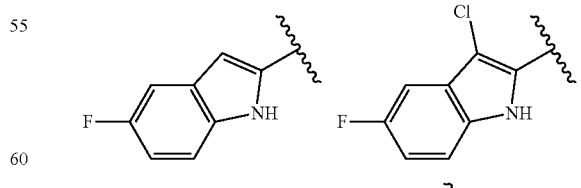
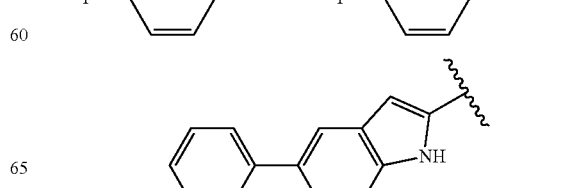

27
-continued
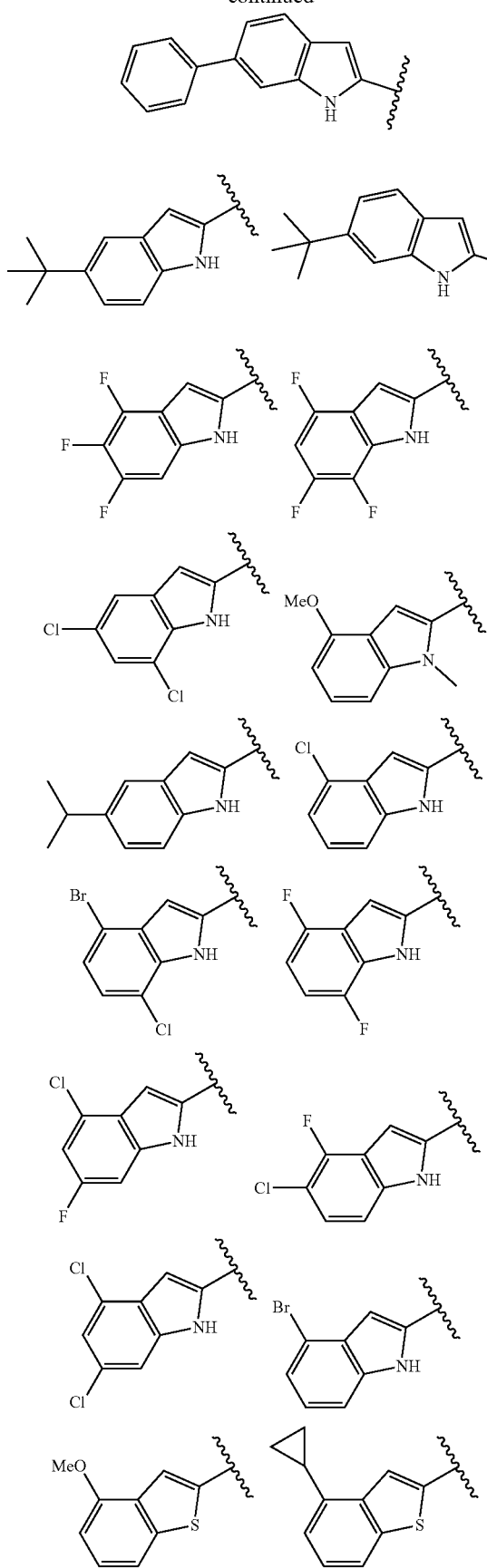
28
-continued
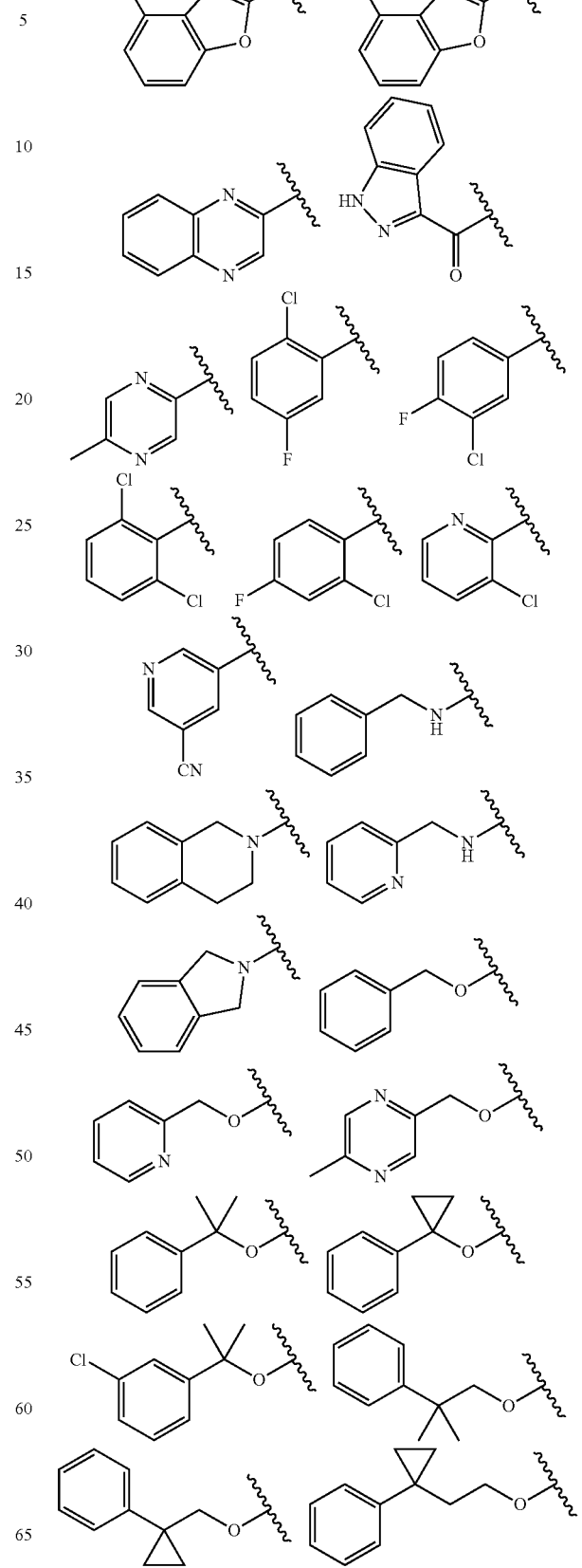

-continued
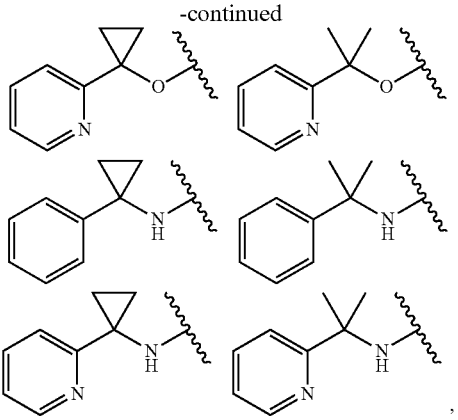
X is selected from the following:
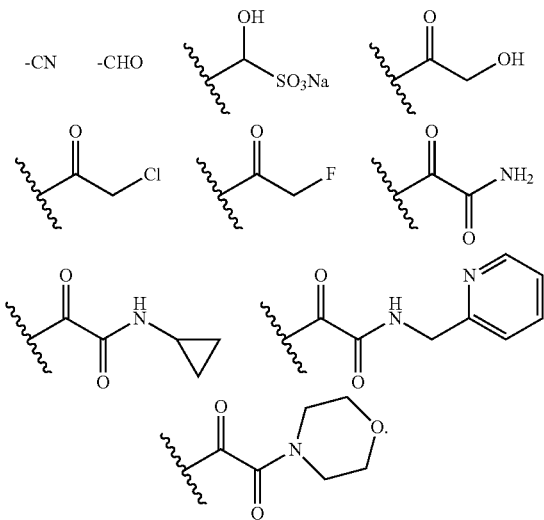
and R₁ is selected from the following:
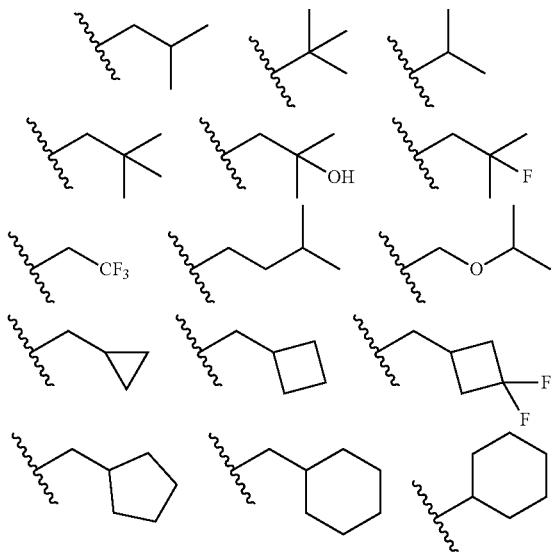
-continued
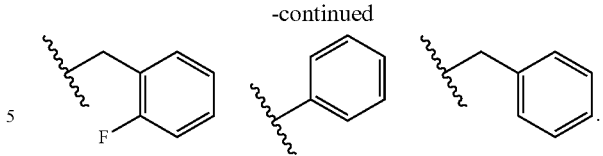
In certain embodiments, the compound of Formula (Ia) is represented by one of Formulae (VIII-1) to (VIII-5):
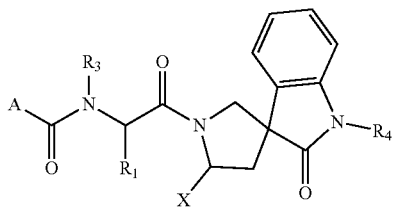
(VIII-1)
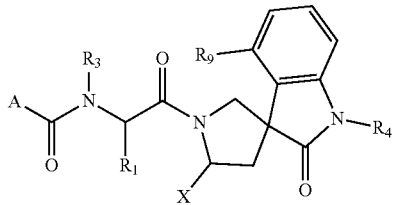
(VIII-2)
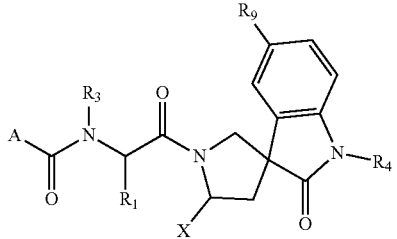
(VIII-3)
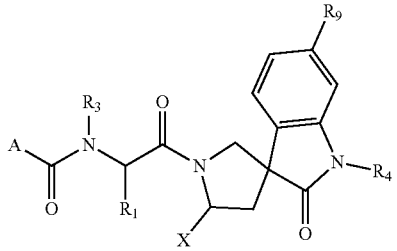
(VIII-4)
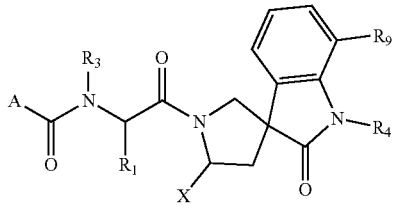
(VIII-5)
wherein A, X, $R_1$, $R_3$, $R_4$, and $R_9$ are as previously defined.
In certain embodiments, the compound of Formula (Ia) is represented by one of Formulae (IX-1) to (IX-5):

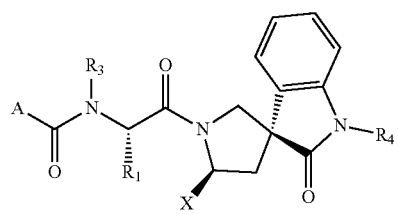
(IX-1)

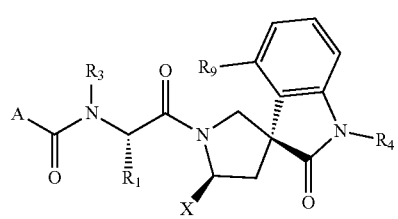
(IX-2)

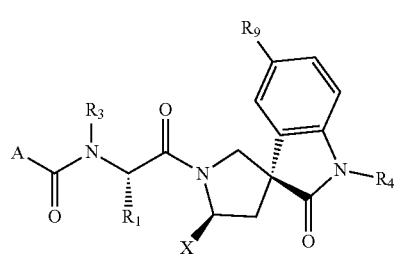
(IX-3)

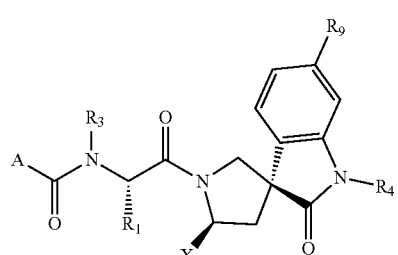
(IX-4)

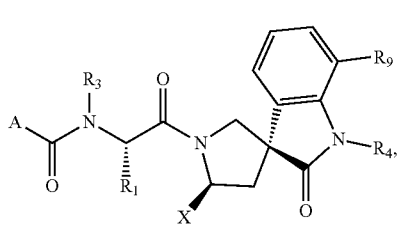
(IX-5)

wherein A, X, R₁, R₃, R₄, and R₉ are as previously defined.

In certain embodiments, the compound of Formula (Ia) is represented by one of Formulae (VIII-1) to (VIII-5) and Formulae (IX-1) to (IX-5), wherein $R_3$ is hydrogen, -Me, -Et, —Pr, -i-Pr, -allyl, —CF$_3$, -CD$_3$, or cyclopropyl; $R_4$ is hydrogen, -Me, -Et, —Pr, -i-Pr, -allyl, —CF$_3$ or cyclopropyl; $R_9$ is halogen, —OCH$_3$, —NH$_2$, —CH$_3$, or —CF$_3$; A is selected from the following

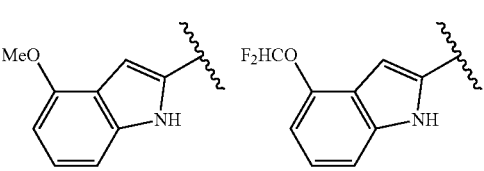

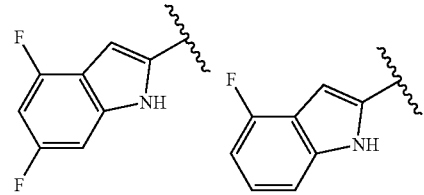

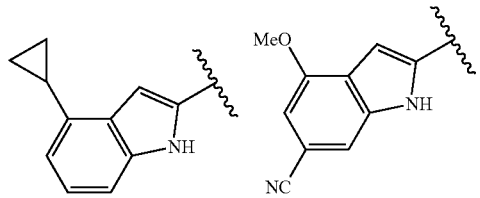

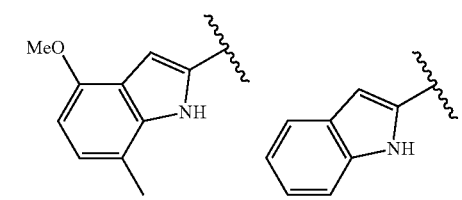

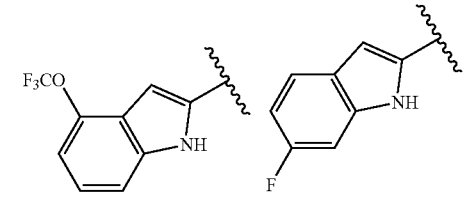

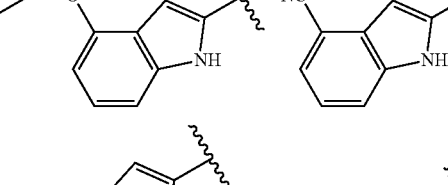

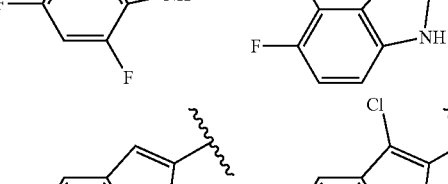

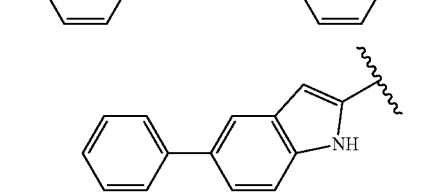

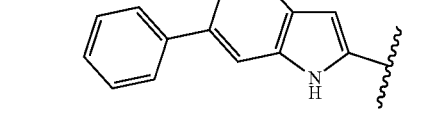

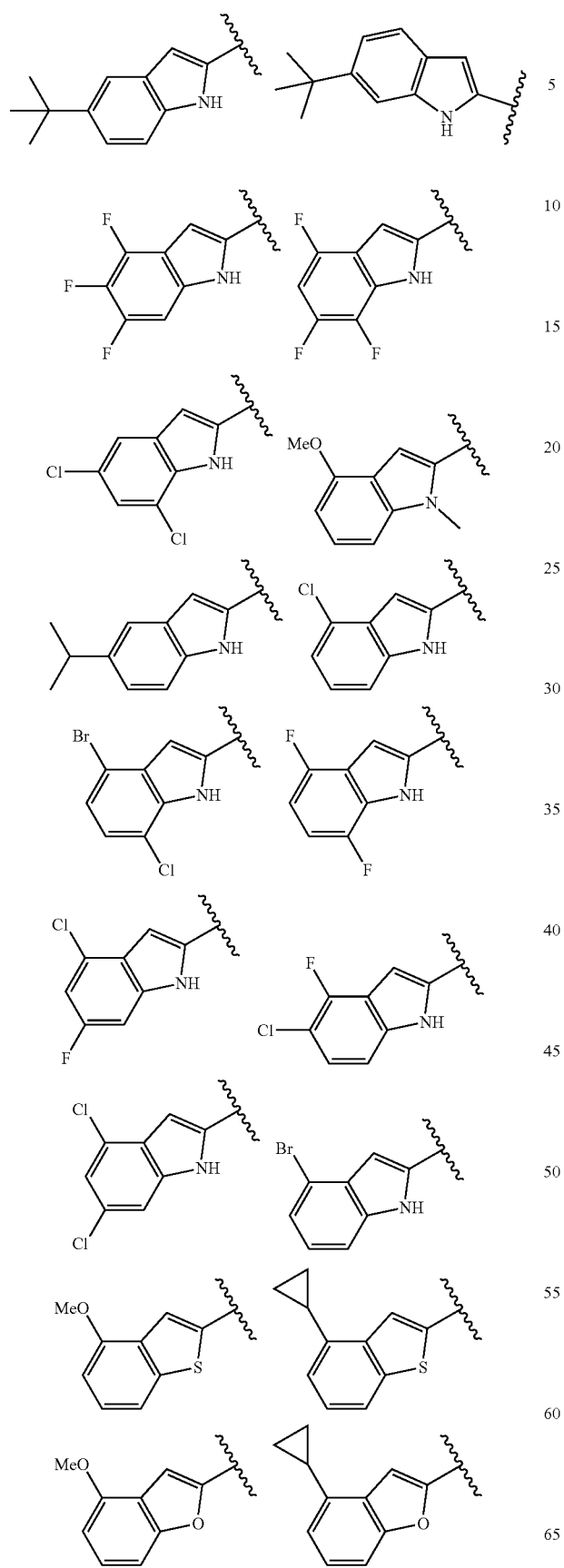
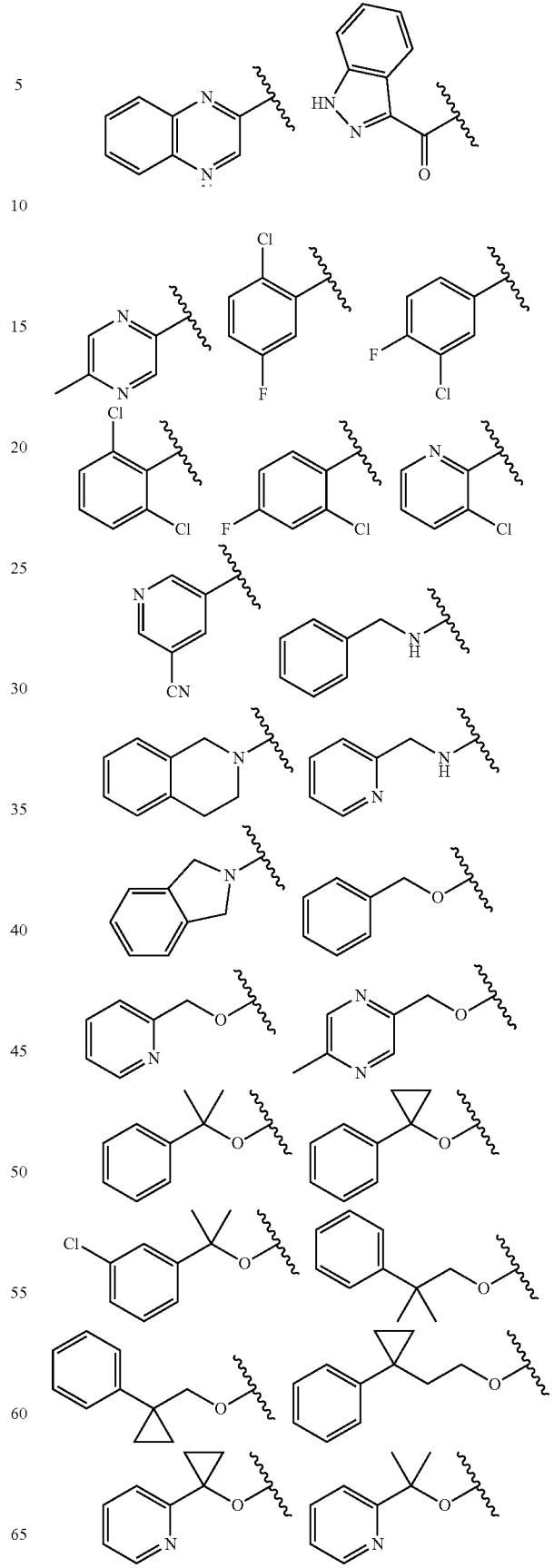

-continued

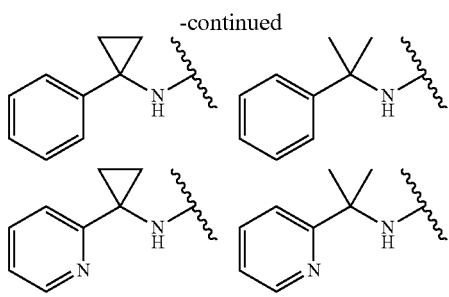

X is selected from the following:

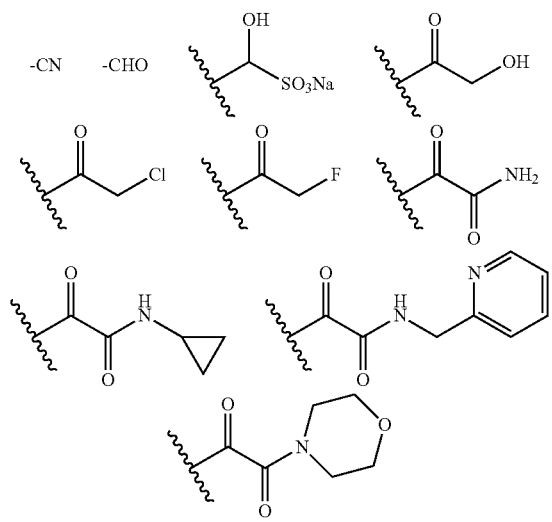

and R₁ is selected from the following:

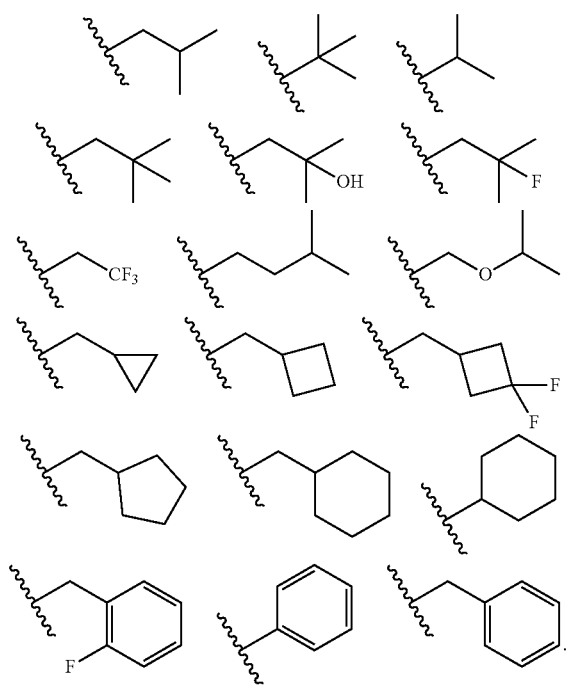

In certain embodiments, the compound of Formula (Ia) is represented by one of Formulae (X-1) to (X-4):

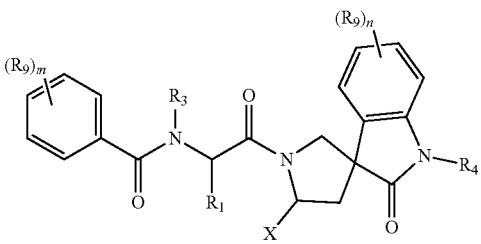

(X-1)

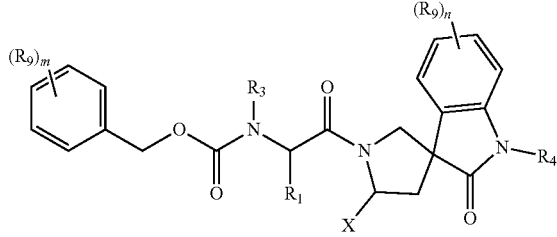

(X-2)

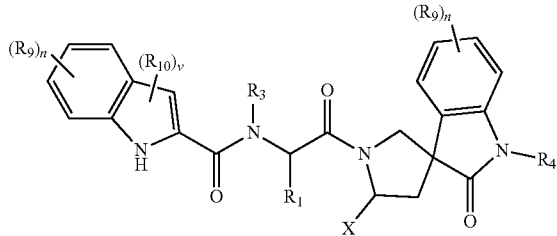

(X-3)

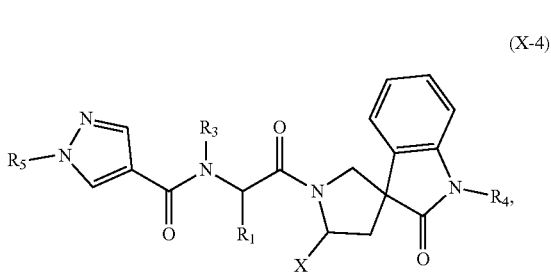

(X-4)

wherein m is 0, 1, 2, 3, 4 or 5; v is 0, 1 or 2; $R_{10}$ is optionally substituted —$C_1$-$C_4$ alkyl or optionally substituted —$C_3$-$C_6$ cycloalkyl; X, $R_1$, $R_3$, $R_4$, $R_9$, and n are as previously defined and $R_5$ is hydrogen, optionally substituted —$C_1$-$C_6$ alkyl; optionally substituted —$C_3$-$C_8$ cycloalkyl; Optionally substituted 3- to 8-membered heterocycloalkyl; optionally substituted aryl; or optionally substituted heteroaryl.

In certain embodiments, the compound of Formula (Ia) is represented by one of Formulae (XI-1) to (XI-3):

(XI-1)
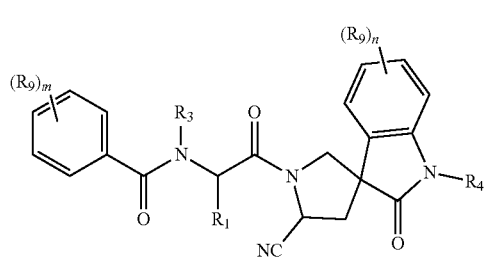
(XI-2)
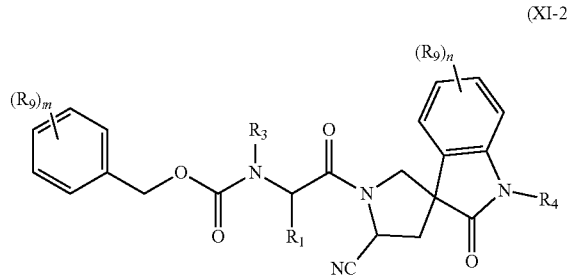
(XI-3)
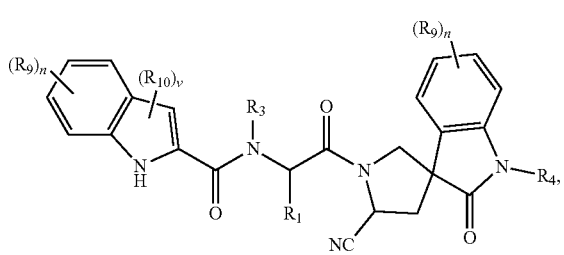
wherein $R_1$, $R_3$, $R_4$, $R_9$, $R_{10}$, m, n, and v are as previously defined.
In certain embodiments, the compound of Formula (Ia) is represented by one of Formulae (XII-1) to (XII-6):
(XII-1)
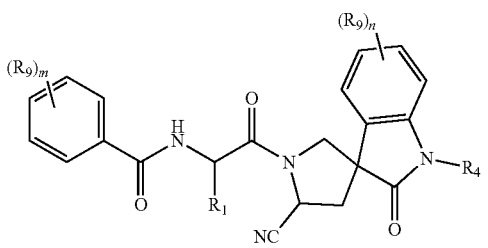
(XII-2)
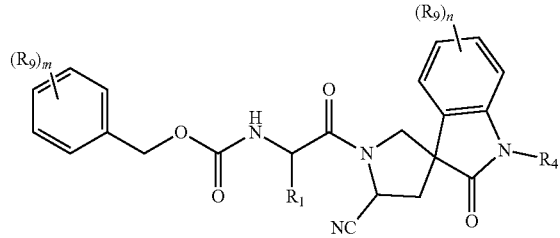
(XII-3)
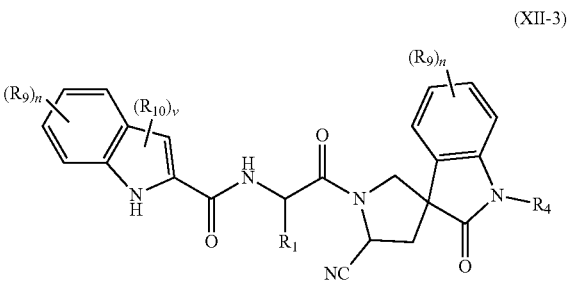
(XII-4)
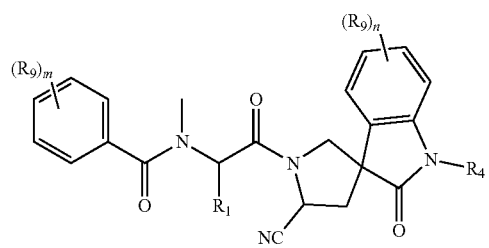
(XII-5)
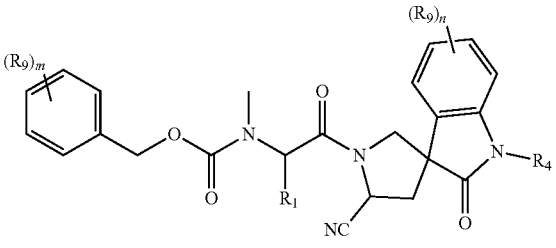
(XII-6)
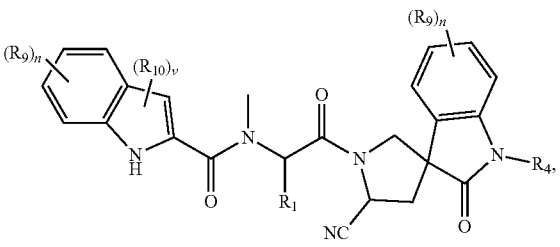
wherein $R_1$, $R_4$, $R_9$, $R_{10}$, m, n, and v are as previously defined.
In certain embodiments, the compound of Formula (Ia) is represented by one of Formulae (XIII-1) to (XIII-6):
(XIII-1)
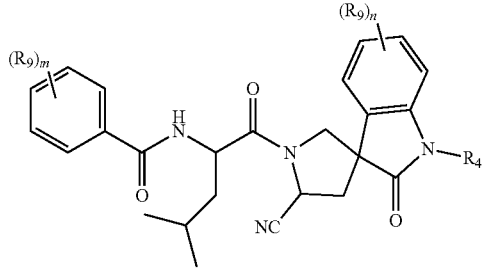

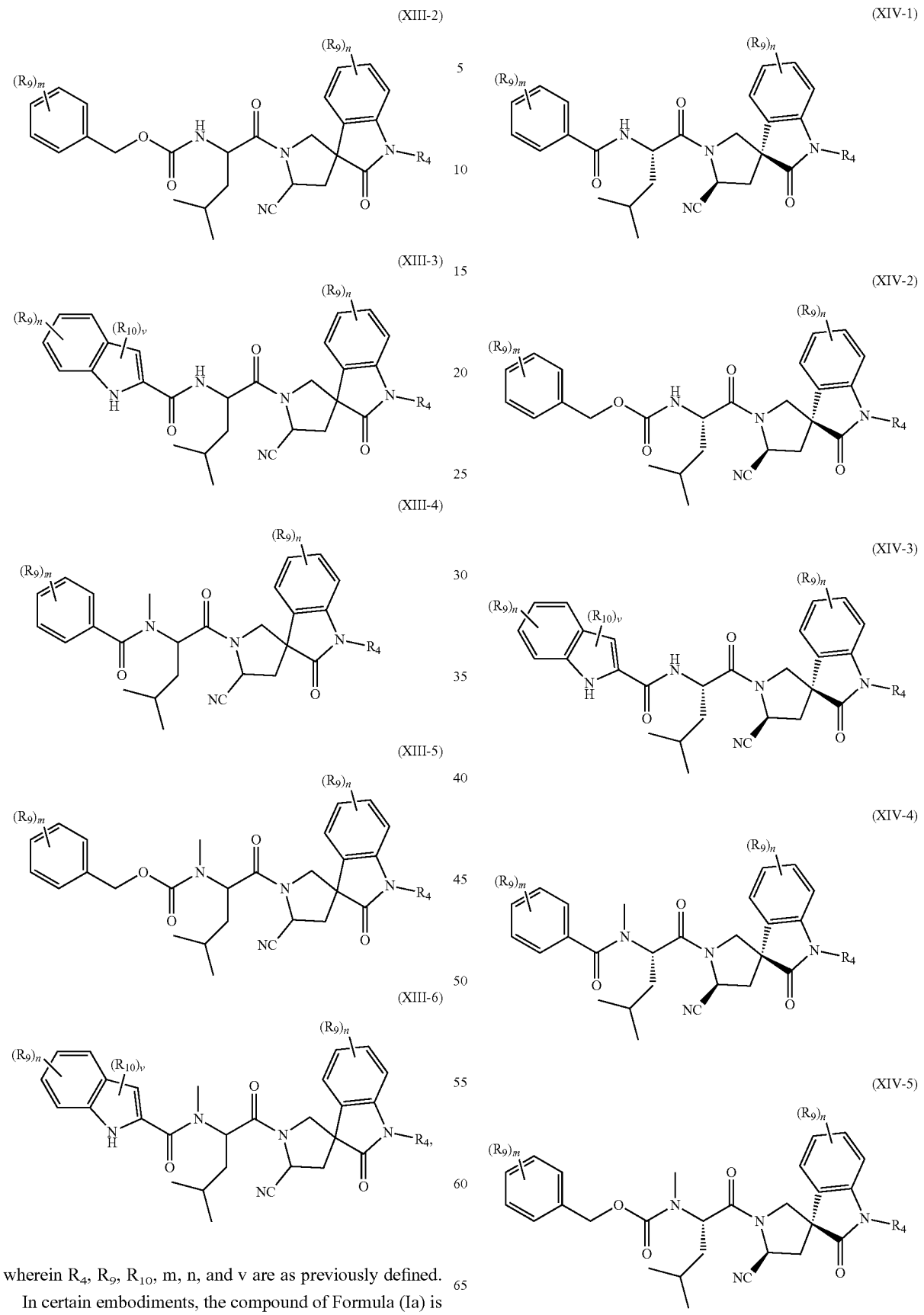
wherein $R_4$, $R_9$, $R_{10}$, m, n, and v are as previously defined.
In certain embodiments, the compound of Formula (Ia) is represented by one of Formulae (XIV-1) to (XIV-6):

-continued (XIV-6)

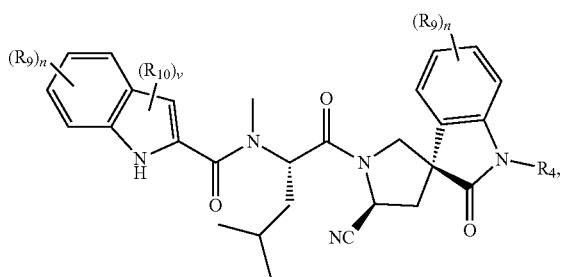

wherein $R_4$, $R_9$, $R_{10}$, m, n, and v are as previously defined.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —CH2CH2-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted. Preferably, as used herein, arylalkyl is aryl-$C_1$-$C_6$ alkyl, and heteroarylalkyl is heteroaryl-$C_1$-$C_6$ alkyl.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocycloalkyl, —$OCONH_2$, —OCONH—$C_1C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH— $C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy; acetyl; —CN; —OH; $NH_2$; $C_1$-$C_4$-alkylamino; di($C_1$-$C_4$-alkyl)amino; and $N_{O2}$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T.H. Greene and P.G.M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T.H. Greene and P.G.M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic*

*Transformations*, 2$^{nd}$ Ed. Wiley-VCH (1999); T. W. Greene and P.G.M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

In certain embodiments, the present invention provides a method of treating or preventing a viral infection in a subject in need thereof, comprising administering to the subject a therapeutically effective amount of a compound of Formula (I) or a pharmaceutically acceptable salt thereof. The viral infection is preferably a coronavirus infection. In certain embodiments, the coronavirus is SARS-CoV-1, SARS-CoV-2, or MERS-CoV. Preferably the coronavirus is SARS-CoV-2.

A viral inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount of the compound described above may range, for example, from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-1gE, anti-TNF, anti-IL-5, anti-IL-6, anti-IL-12, anti-IL-1 and similar agents; cytokine receptor therapies e.g. etanercept and similar agents; antigen non-specific immunotherapies (e.g., interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, antheimintic agents, antimalarial agents, antiprotozoal agents, antitubercuiosis agents, and antiviral agents, including those listed at https://www.drugs.com/drug-class/anti-infectives.html. In general, combination therapy is typically preferred over alternation therapy because it induces multiple simultaneous stresses on the virus.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, combined with a compound of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

Abbreviations

Abbreviations which may be used in the descriptions of the scheme and the examples that follow are: Ac for acetyl; AcOH for acetic acid; Boc$_2$O for di-tert-butyl-dicarbonate; Boc for t-butoxycarbonyl; Bz for benzoyl; Bn for benzyl; t-BuOK for potassium tert-butoxide; Brine for sodium chloride solution in water; CDI for carbonyldiimidazole; DCM or CH$_2$Cl$_2$ for dichloromethane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; DBU for 1,8-diazabicyclo[5.4.0]-undec-7-ene; DEAD for diethylazodicarboxylate; DIAD for diisopropyl azodicarboxylate; DIPEA or (i-Pr)$_2$EtN for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EtOAc for ethyl acetate; EtOH for ethanol; Et20 for diethyl ether; HATU for O-(7-azabenzotriazol-2-yl)-N,N,N',N',-tetramethyluronium Hexafluorophosphate; HCl for hydrogen chloride; K$_2$CO$_3$ for potassium carbonate; n-BuLi for n-butyl lithium; DDQ for 2,3-dichloro-5,6-dicyano-1,4-benzoquinone; LDA for lithium diisopropylamide; LiTMP for lithium 2,2,6,6-tetramethylpiperidinate; MeOH for methanol; Mg for magnesium; MOM for methoxymethyl; Ms for mesyl or —SO$_2$—CH$_3$; NaHMDS for sodium bis(trimethylsilyl)amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$Cl for ammonium chloride; Ni for nickel; OH for hydroxyl; OsO$_4$ for osmium tetroxide; OTf for triflate; PPA for polyphosphoric acid; PTSA for p-toluenesulfonic acid; PPTS for pyridinium p-toluenesulfonate; TBAF for tetrabutylammonium fluoride; TEA or Et$_3$N for triethylamine; TES for triethylsilyl; TESCl for triethylsilyl chloride; TESOTf for triethylsilyl trifluoromethanesulfonate; TFA for trifluoroacetic acid; THE for tetrahydrofuran; TMEDA for N,N,N',N'-tetramethylethylene-diamine; TPP or PPh$_3$ for triphenyl-phosphine; Tos or Ts for tosyl or —SO$_2$—C$_6$H$_4$CH$_3$; Ts$_2$O for tolylsulfonic anhydride or tosyl-anhydride; TsOH for p-tolylsulfonic acid; Pd for palladium; Ph for phenyl; Pd$_2$(dba)$_3$ for tris(diben-zylideneacetone) dipalladium (0); Pd(PPh$_3$)$_4$ for tetrakis(triphenylphosphine)-palladium (0); PdCl$_2$(PPh$_3$)$_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; and TMSCI for trimethylsilyl chloride.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

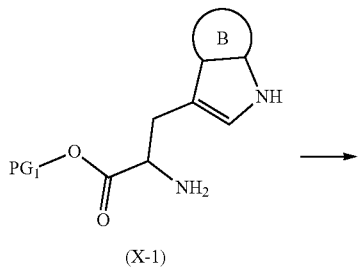

(X-1)

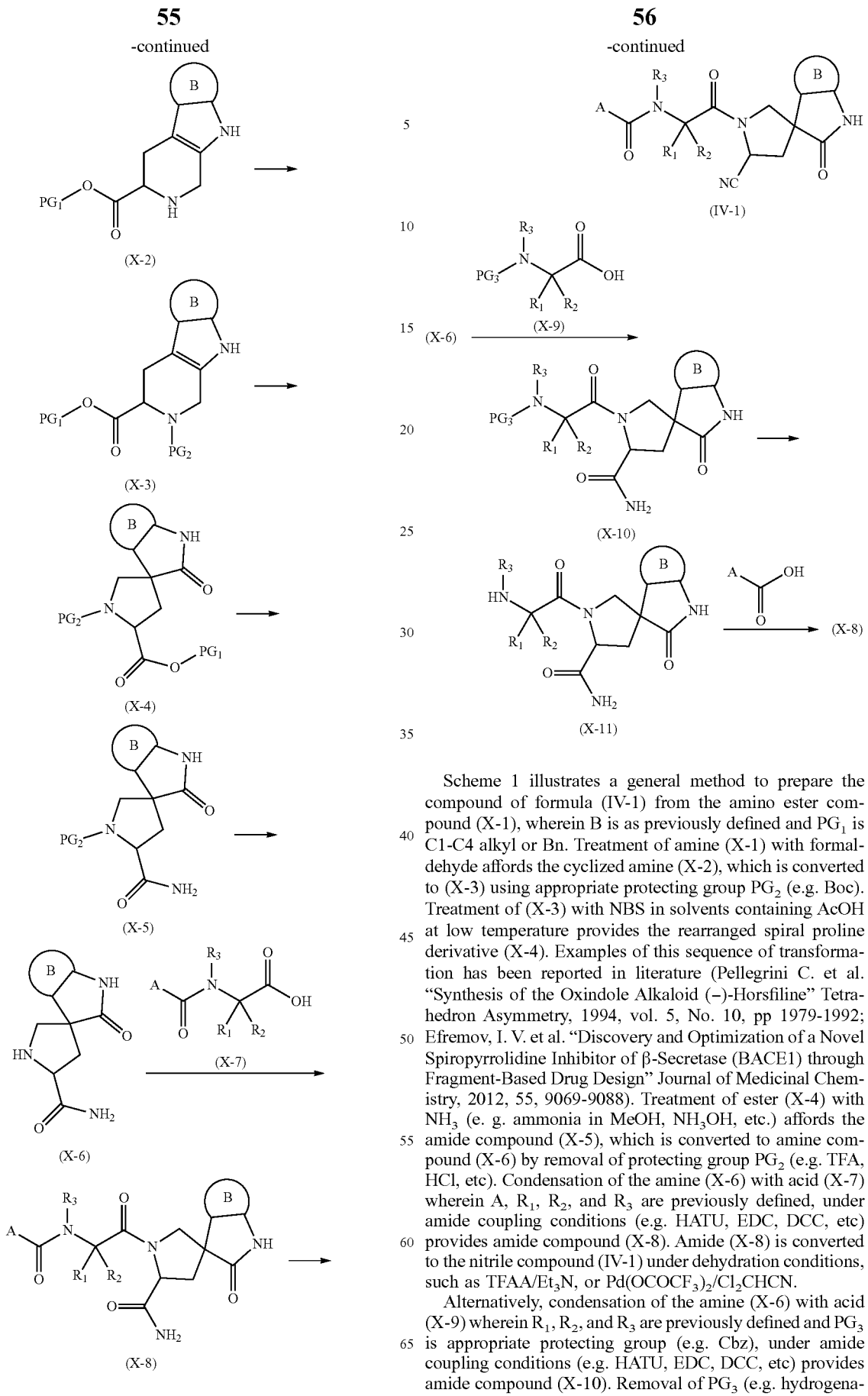

Scheme 1 illustrates a general method to prepare the compound of formula (IV-1) from the amino ester compound (X-1), wherein B is as previously defined and PG$_1$ is C1-C4 alkyl or Bn. Treatment of amine (X-1) with formaldehyde affords the cyclized amine (X-2), which is converted to (X-3) using appropriate protecting group PG$_2$ (e.g. Boc). Treatment of (X-3) with NBS in solvents containing AcOH at low temperature provides the rearranged spiral proline derivative (X-4). Examples of this sequence of transformation has been reported in literature (Pellegrini C. et al. "Synthesis of the Oxindole Alkaloid (−)-Horsfiline" Tetrahedron Asymmetry, 1994, vol. 5, No. 10, pp 1979-1992; Efremov, I. V. et al. "Discovery and Optimization of a Novel Spiropyrrolidine Inhibitor of β-Secretase (BACE1) through Fragment-Based Drug Design" Journal of Medicinal Chemistry, 2012, 55, 9069-9088). Treatment of ester (X-4) with NH$_3$ (e. g. ammonia in MeOH, NH$_3$OH, etc.) affords the amide compound (X-5), which is converted to amine compound (X-6) by removal of protecting group PG$_2$ (e.g. TFA, HCl, etc). Condensation of the amine (X-6) with acid (X-7) wherein A, R$_1$, R$_2$, and R$_3$ are previously defined, under amide coupling conditions (e.g. HATU, EDC, DCC, etc) provides amide compound (X-8). Amide (X-8) is converted to the nitrile compound (IV-1) under dehydration conditions, such as TFAA/Et$_3$N, or Pd(OCOCF$_3$)$_2$/Cl$_2$CHCN.

Alternatively, condensation of the amine (X-6) with acid (X-9) wherein R$_1$, R$_2$, and R$_3$ are previously defined and PG$_3$ is appropriate protecting group (e.g. Cbz), under amide coupling conditions (e.g. HATU, EDC, DCC, etc) provides amide compound (X-10). Removal of PG$_3$ (e.g. hydrogenation) affords amine compound (X-11). Condensation of amine (X-11) with acid (A-COOH) wherein A is previously defined, under amide coupling conditions (e.g. HATU, EDC, DCC, etc) or acylhalide generating conditions (e.g. Ghosez's reagent), provides amide compound (X-8)

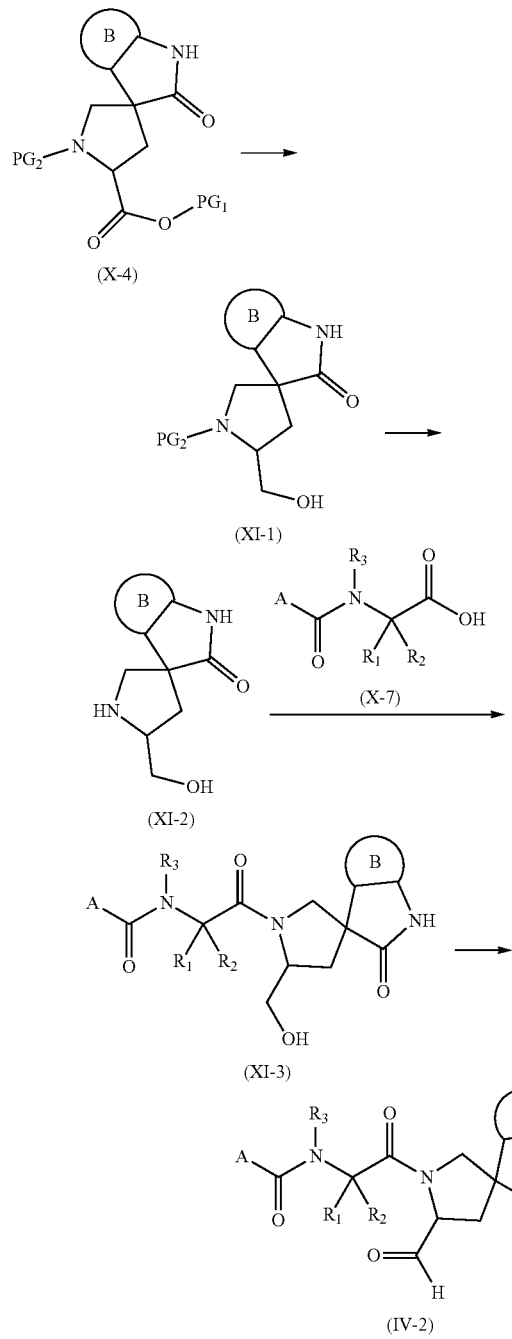

Scheme 2 illustrates a general method to synthesize the aldehyde compound of formula (IV-2), wherein A, $R_1$, $R_2$, $R_3$, and B are previously defined. The ester compound of formula (X-4), wherein B, $PG_1$ and $PG_2$ are previously defined, is reduced to the alcohol compound (XI-1) employing reducing reagents such as, but not limited to, $LiBH_4$, $NaBH_4$, or DIBAL-H. The protecting group $PG_2$ (e.g. Boc)

of (XI-1) is removed under acidic conditions using such as TFA, HCl, formic acid, TMSOTf/lutidine, etc. Coupling of the amine compound (XI-2) with the acid compound (X-7) wherein A, $R_1$, $R_2$, and $R_3$ are previously defined, using coupling reagents such as HATU, EDC, or DCC, provides compound (XI-3). Oxidation of the alcohol of (XI-3) with mild oxidation reagents such as $DMSO/Ac_2O$, Dess-Martin periodinane, IBX, $SO_3$-pyridine/DMSO/$Et_3N$, produces the aldehyde compound (IV-2).

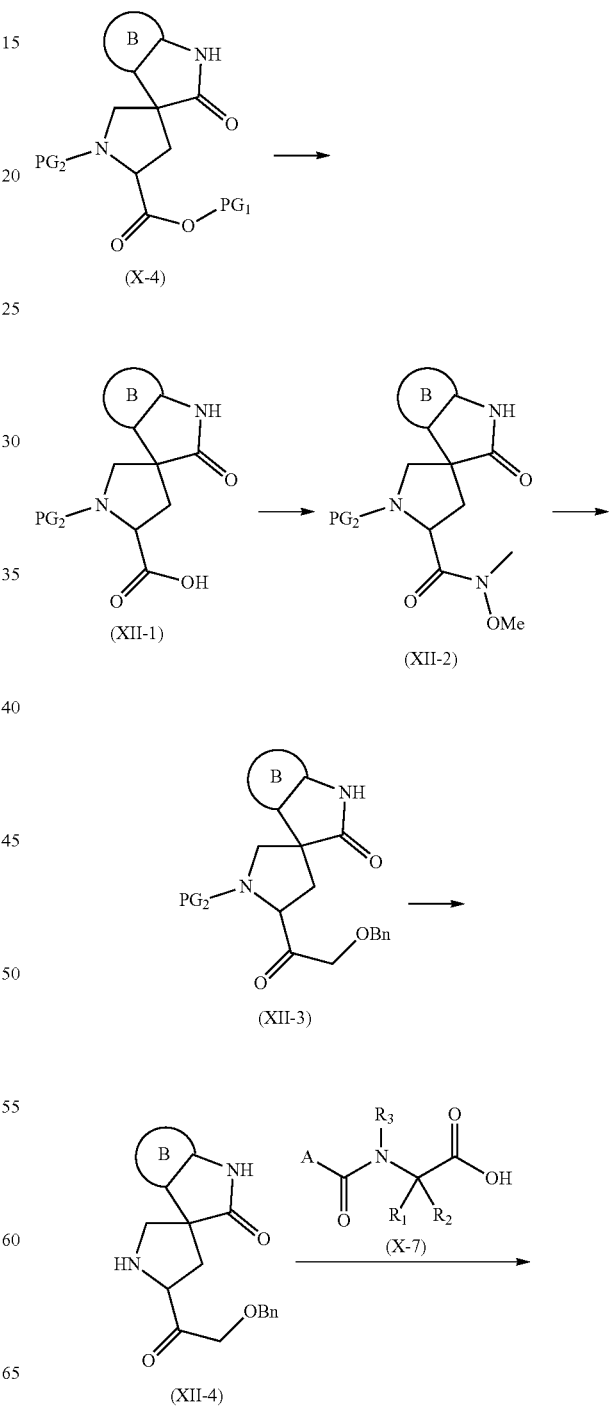

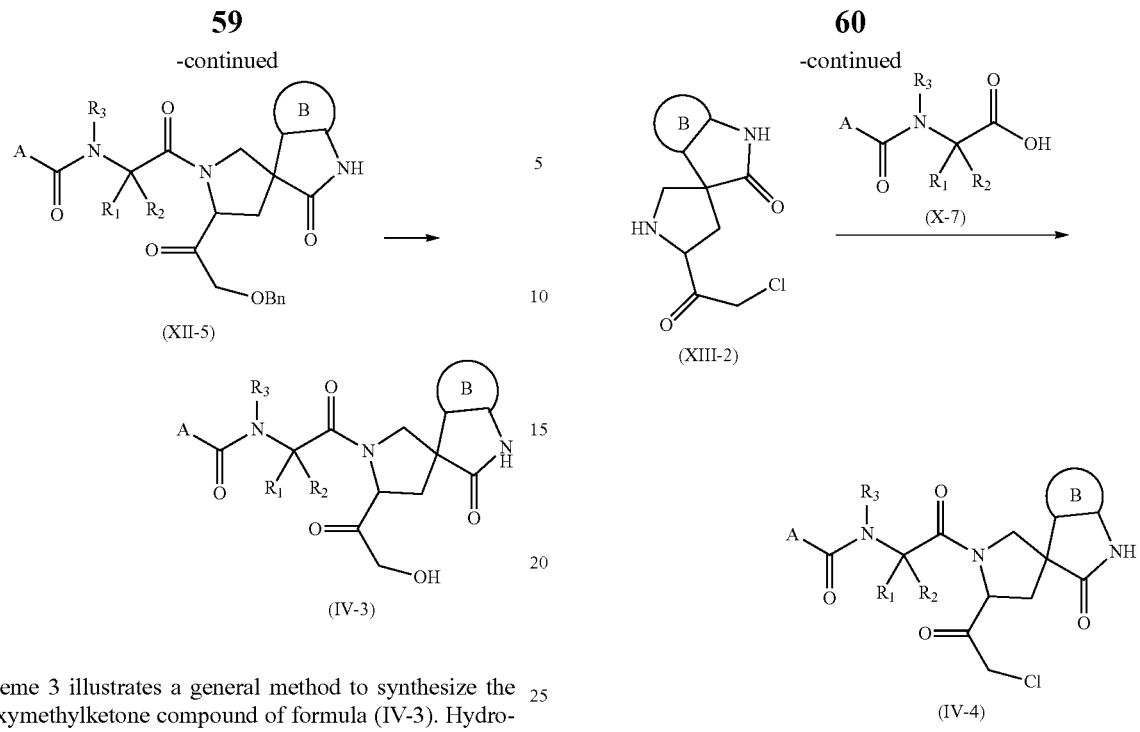

Scheme 3 illustrates a general method to synthesize the hydroxymethylketone compound of formula (IV-3). Hydrolysis of the ester compound (X-4), wherein B, PG₁ and PG₂ are previously defined, provides the acid compound (XII-1). Amide (XII-2) can be obtained from the acid compound (XII-1) by coupling with N,O-dimethylhydroxyamine using reagents such as HATU, EDC, DCC, etc. Treatment of amide (XII-2) at low temperature (e.g. −60° C.) with an organometallic regeat generated by BOM-Cl, Mg, and HgCl₂ affords the ketone compound (XII-3). Removal of PG₂ (e.g. PTSA if PG₂ is BOC) provides amine compound (XII-4). Coupling of amine (XII-4) with acid (X-7), wherein A, R₁, R₂, and R₃ are previously defined, affords compound (XII-5) using amide coupling reagents such as HATU, EDC, DCC, etc. Removal of the benzyl group in (XII-5) under hydrogenation conditions (Pd/C, H₂) provides compound of formula (IV-3).

Scheme 4 illustrates a general method to synthesize the chloromethylketone compound of formula (IV-4). Treatment of the ester compound (X-4) with an organometallic reagent generated by ICH₂Cl and appropriate base, such as LDA, MeLi/LiBr, or BuLi, provides the chloroketone compound (XIII-1). Removal of PG₂ (e.g. PTSA if PG₂ is BOC) provides amine compound (XIII-2). Coupling of amine (XIII-2) with acid (X-7), wherein A, R₁, R₂, and R₃ are previously defined, affords compound (IV-4) using coupling reagents such as HATU, EDC, DCC, etc.

Scheme 5

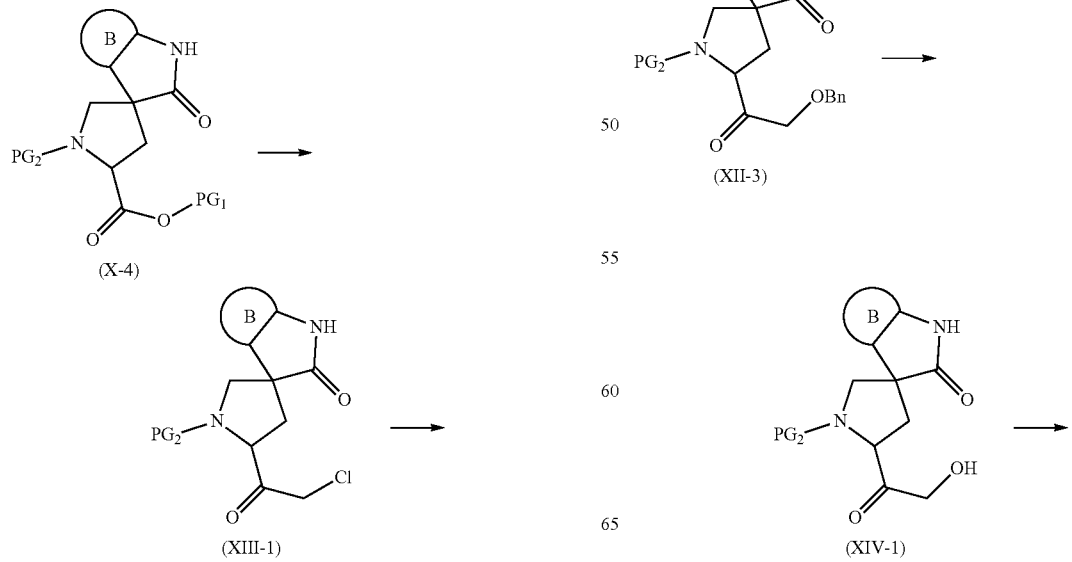

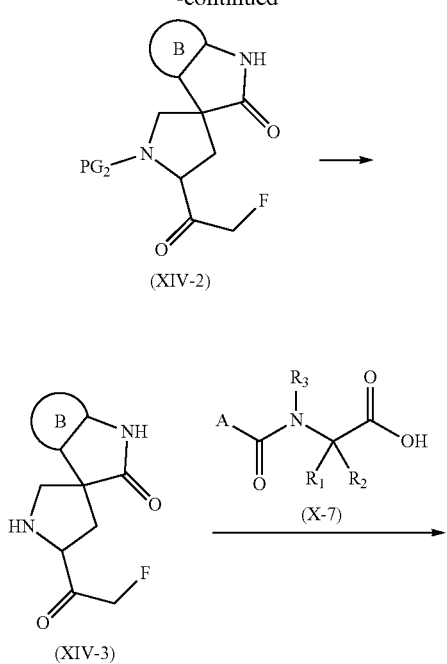

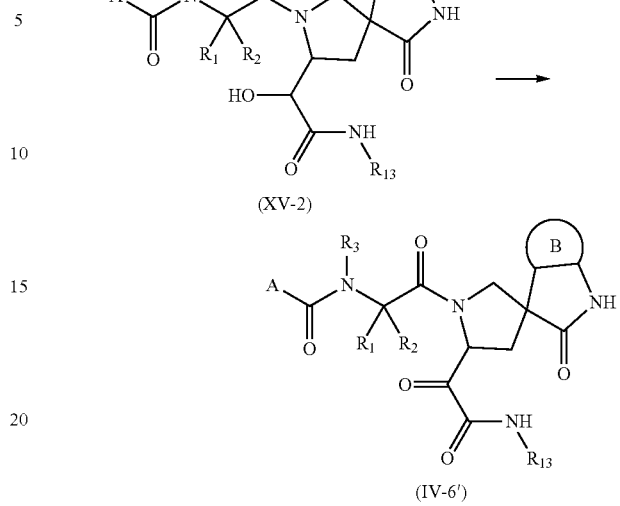

(XV-2)

(IV-6')

Scheme 6 illustrates a general method to synthesize the α-ketoamide compound of formula (IV-6). Treatment of the aldehyde compound of formula (IV-2), wherein A, $R_1$, $R_2$, $R_3$, and B are previously defined, with isonitrile compound (XV-1), wherein $R_{13}$ is previously defined, affords α-hydroxylamide (XV-2). Oxidation of compound (XV-2) with appropriate oxidants such as Dess-Martin periodinane, $(COCl)_2$/DMSO/$Et_3N$, PCC, $SO_3$-pyridine/DMSO/$Et_3N$, affords α-ketoamide of formula (IV-6').

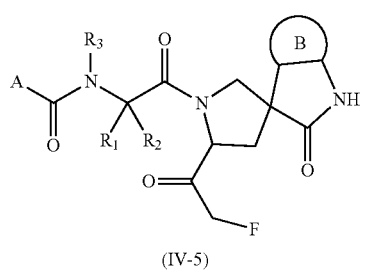

(IV-5)

Scheme 5 illustrates a general method to synthesize the fluoromethylketone compound of formula (IV-5). Removal of the Bn group of compound (XII-3) with Pd-catalyzed hydrogenation provides alcohol compound (XIV-1). Alcohol (XIV-1) is converted to fluoromethylketone compound (XIV-2) under conditions such as $SF_4$, $Tf_2O$/lutidine/TBAF, $C_4F_9SO_2F$/HF-$Et_3N$, etc. Removal of $PG_2$ (e.g. PTSA if $PG_2$ is BOC) provides amine compound (XIV-3). Coupling of amine (XIV-3) with acid (X-7), wherein A, $R_2$, and $R_3$ are previously defined, affords compound (IV-5) using amide coupling reagents such as HATU, EDC, DCC, etc.

Scheme 6

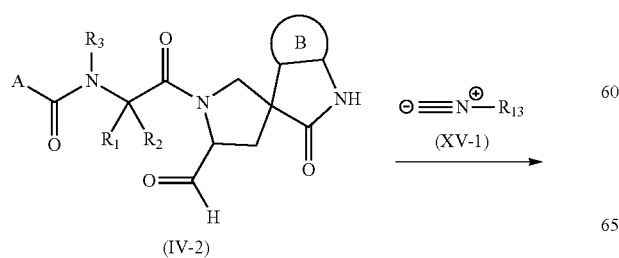

Scheme 7

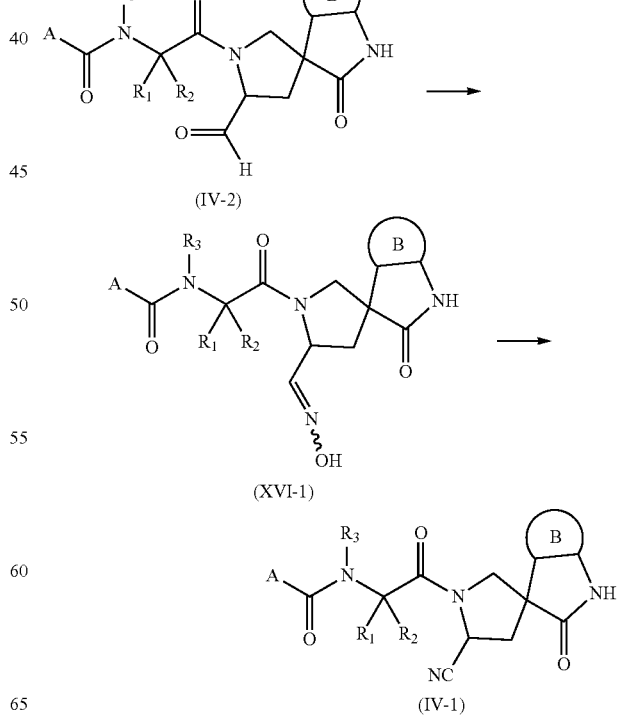

Alternatively, nitrile compound (IV-1) can be synthesized from aldehyde compound (IV-2) using the method shown in Scheme 7. Condensation of aldehyde (IV-2) with hydroxyamine hydrochloride in appropriate solvents such as DMSO, i-PrOH, pyridine, etc. provides oxime compound (XVI-1). Treatment of the oxime compound (XVI-1) under acid-catalyzed dehydration conditions such as (Cu(OAc)$_2$/MeCN, HCl, etc.) affords the nitrile compound (IV-1).

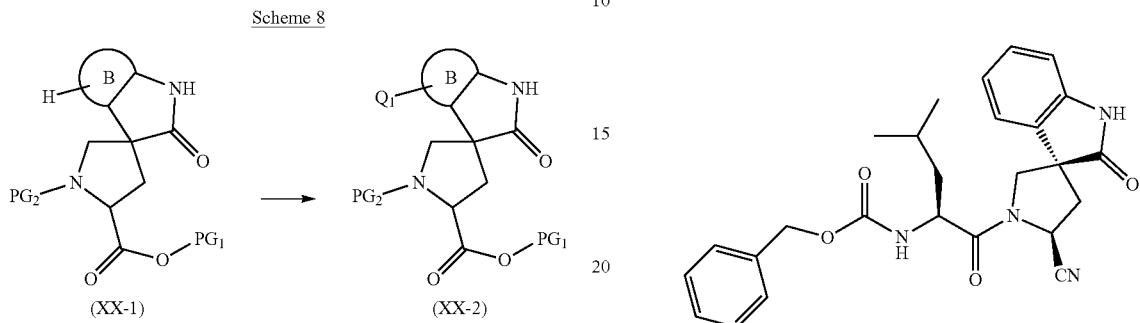

Scheme 8

(XX-1)  (XX-2)

Scheme 8 illustrates a general method to synthesize functionalized spirocycles of formula XX-2 ($Q_1$ defined as halogen or optionally substituted alkyl). Treatment of the spirocyclic compound of formula XX-1, wherein B, $PG_1$, and $PG_2$ are previously defined, with an electrophilic reagent, including, but not limited to: sulfuryl chloride, N-chlorosuccinimide, N-bromosuccinimide, SelectFluor, or NFSI, can provide functionalized spirocycle XX-2.

EXAMPLES

The compounds and processes of the present invention will be better understood in connection with the following examples, which are intended as an illustration only and not limiting of the scope of the invention. Starting materials were either available from a commercial vendor or produced by methods well known to those skilled in the art.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-C18 column (4.6×30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. [M+H]$^+$ refers to mono-isotopic molecular weights.

NMR spectra were run on a Bruker 400 MHz spectrometer. Spectra were measured at 298K and referenced using the solvent peak. Chemical shifts for $^1$H NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO C18 column (250×21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Example 1

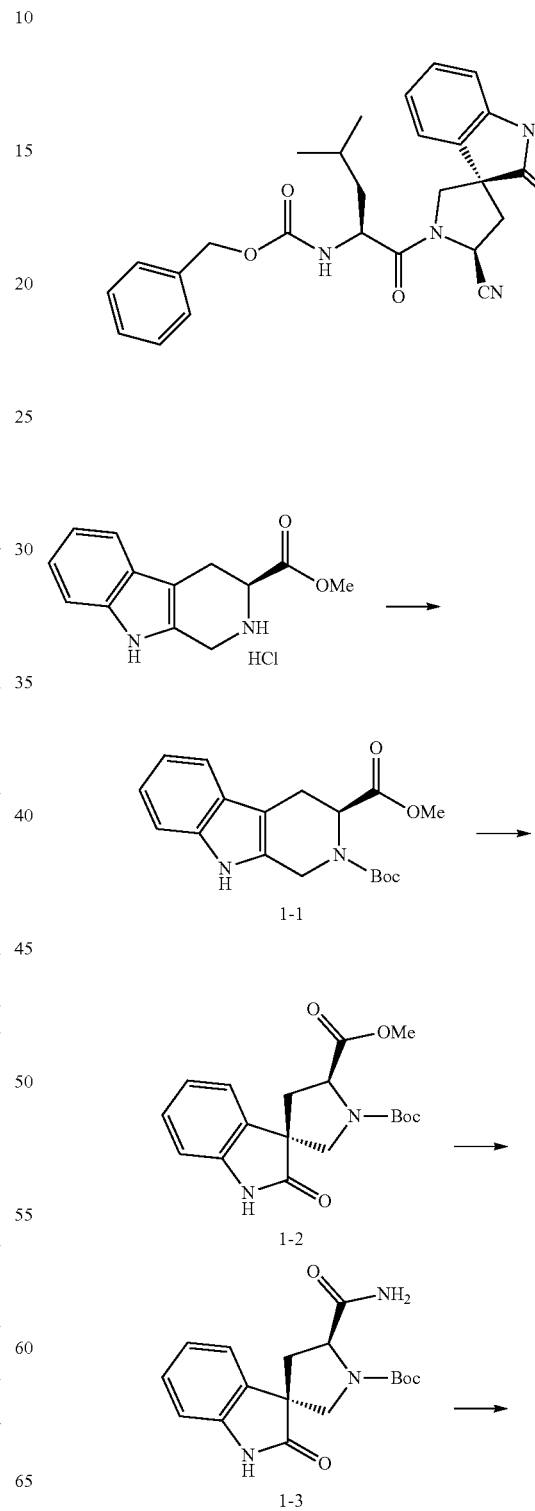

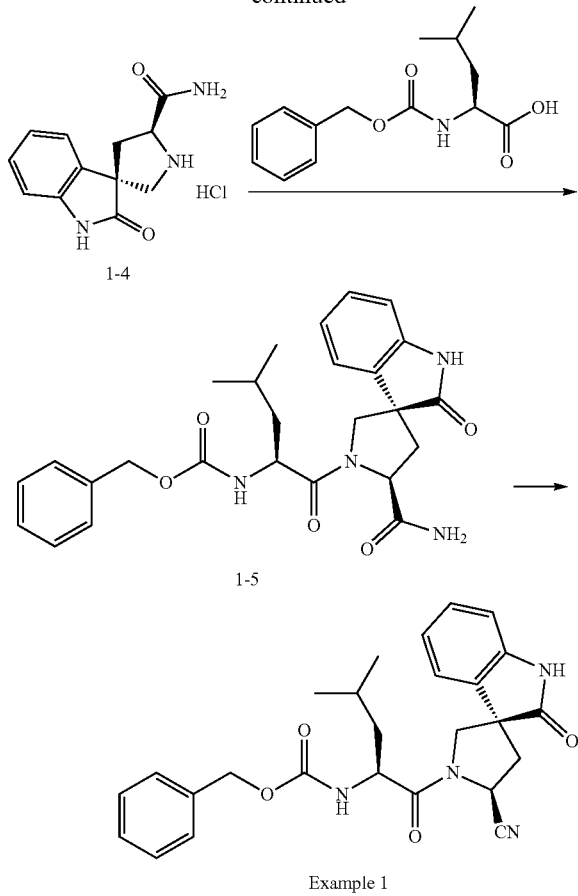

1-4

1-5

Example 1

Step 1-1 methyl (S)-2,3,4,9-tetrahydro-1H-pyrido[3,4-b]indole-3-carboxylate hydrochloride (500 mg, 1.875 mmol) was dissolved in CH$_2$Cl$_2$ (10 ml). Triethylamine (523 µl, 3.75 mmol) and a 2.0 M solution of di-tert-butyl dicarbonate in DCM (1031 µl, 2.062 mmol) was added. The mixture was stirred at rt for 3 h, quenched with sat. NaHCO3, and extracted with DCM. The organic layer was washed with brine, dried over MgS$_4$, and concentrated in vacuo. Purification of the residue on silica gel with 0-30% EtOAc/cyclohexane provided compound (1-1) (578 mg, 1.749 mmol, 93% yield).

Step 1-2

Compound (1-1) was dissolved in THF (15 ml), AcOH (10 ml), and water (10 ml). The solution was cooled to −15° C. A solution of NBS (328 mg, 1.843 mmol) in THF (5 mL) was added dropwise. The mixture was slowly warmed to 5° C. over 1 h. The reaction was quenched with Na$_2$SO$_3$ and sat. NaHCO$_3$, and extracted with DCM (2×). The organic layer was washed with brine, dried with MgSO$_4$, and concentrated in vacuo. Purification of the residue on silica gel with 0-50% EtOAc/cyclohexane provided compound (1-2) (328 mg, 0.947 mmol, 53.900 yield).

Step 1-3

Compound (1-2) (328 mg, 0.947 mmol) was dissolved in MeOH (3 ml). A solution of 7 N ammonia in MeOH (5 mL, 35.0 mmol) was added. The mixture was stirred at rt for 5 days. Solvent was removed in vacuo. Purification of the residue on silica gel with 0-10% MeOH/DCM, and on C18 column with 0-50% MeCN/H$_2$O provided compound (1-3) (101 mg, 0.305 mmol, 32.2% yield).

Step 1-4

Compound (1-3) (100 mg, 0.302 mmol) was dissolved in DCM and trifluoroacetic acid (232 µl, 3.02 mmol) was added. The mixture was stirred at 0° C. for 1 h, and at rt for 2 h. DCM (10 mL) and toluene (10 mL) were added. Solvent was removed in vacuo. The residue was dissolved in MeOH and 1 M HCl (0.6 mL, 2 eq) was added. Solvent was removed. The obtained compound (1-4) (91 mg, 0.340 mmol, quantative yield) was used for next step.

Step 1-5

Compound (1-4) (15 mg, 0.056 mmol) and ((benzyloxy)carbonyl)-L-leucine (14.87 mg, 0.056 mmol) were dissolved in THF (0.5 ml) and DMF (0.1 ml). DIPEA (30.0 µl, 0.168 mmol) and HATU (21.30 mg, 0.056 mmol) were added. The mixture was stirred at rt for 20 min, quenched with water, and extracted with EtOAc (2×). The organic layer was loaded on silica gel and eluted with 0-70% acetone/cyclohexane to afford compound (1-5) (15 mg, 0.031 mmol, 55.9% yield).

Step 1-6

Compound (1-5) (60 mg, 0.125 mmol) was dissolved in DCM (1.254 ml) (not soluble). Triethylamine (140 µl, 1.003 mmol) and TFAA (70.8 µl, 0.502 mmol) was added. The mixture was stirred at rt for 30 min. The reaction was diluted with DCM and quenched with sat. NaHCO$_3$. The organic layer was loaded on silica gel and eluted with 0-50% acetone/cyclohexane, and on prep-HPLC with 20-85% MeCN/H$_2$O with 0.1% formic acid to afford Example 1 (14 mg, 0.056 mmol) as a white powder. $^1$H NMR (400 MHz, Acetone-d$_6$) δ 9.70 (s, 1H), 7.42-7.31 (m, 5H), 7.28 (td, J=7.7, 1.3 Hz, 1H), 7.12 (d, J=7.4 Hz, 1H), 7.04-6.96 (m, 2H), 6.65 (d, J=8.3 Hz, 1H), 5.17 (t, J=8.3 Hz, 1H), 5.06-4.94 (m, 2H), 4.48 (td, J=9.0, 5.0 Hz, 1H), 4.26 (d, J=10.4 Hz, 1H), 3.99 (d, J=10.3 Hz, 1H), 2.78-2.63 (m, 2H), 1.80 (dd, J=13.8, 6.9 Hz, 1H), 1.74-1.56 (m, 2H), 0.96 (dd, J=8.7, 6.6 Hz, 6H). [M+Na] m/e 483.18.

The following examples were prepared employing similar protocol as described above.

| Example # | Structure | MS | NMR |
|---|---|---|---|
| 2 | 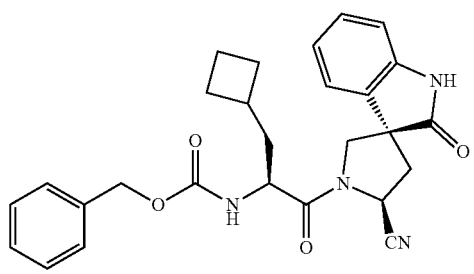 | [M − H]$^-$ 471.16 | $^1$H NMR (400 MHz, Methanol-d$_4$) δ 7.39-7.28 (m, 5H), 7.28 (td, J = 7.7, 1.2 Hz, 1H), 7.11 (d, J = 7.4 Hz, 1H), 7.06-6.93 (m, 2H), 5.14 (t, J = 8.0 Hz, 1H), 5.00 (d, J = 2.4 Hz, 2H), 4.28 (dd, J = 8.2, 6.2 Hz, 1H), 4.18 (d, J = 10.5 Hz, 1H), 3.95 (d, J = 10.5 Hz, 1H), 2.67 (dd, J = 7.9, 1.9 Hz, 2H), 2.44 (p, J = 7.9 Hz, 1H), 2.16-2.05 (m, 3H), 1.97-1.62 (m, 5H). |

-continued

| Example # | Structure | MS | NMR |
|---|---|---|---|
| 3 | 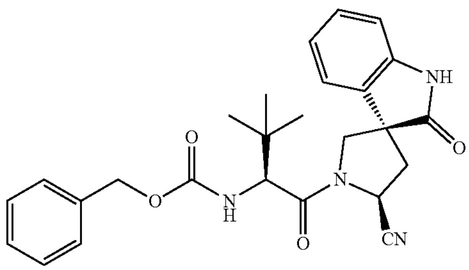 [SMILES: CC(C)(C)[C@H](NC(=O)OCc1ccccc1)C(=O)N1C[C@]2(C[C@H]1C#N)C(=O)Nc1ccccc12] | [M − H]⁻ 459.17 | ¹H NMR (400 MHz, Acetone-d₆) δ 9.55 (s, 1H), 7.28-7.15 (m, 5H), 7.15-7.07 (m, 1H), 6.89 (d, J = 7.5 Hz, 1H), 6.84 (d, J = 7.8 Hz, 1H), 6.80 (t, J = 7.5 Hz, 1H), 6.40 (d, J = 9.0 Hz, 1H), 5.04 (t, J = 8.4 Hz, 1H), 4.84 (s, 2H), 4.16 (dd, J = 17.5, 9.8 Hz, 2H), 3.95-3.84 (m, 1H), 2.64-2.48 (m, 2H), 0.97 (s, 9H). |
| 4 | 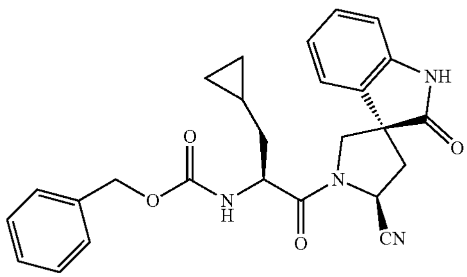 [SMILES: N#C[C@@H]1C[C@@]2(CN1C(=O)[C@H](CC1CC1)NC(=O)OCc1ccccc1)C(=O)Nc1ccccc12] | [M + Na]⁺ 481.16 | ¹H NMR (500 MHz, Chloroform-d) δ 8.17 (s, 1H), 7.32-7.13 (m, 6H), 6.92-6.74 (m, 3H), 5.53 (d, J = 8.3 Hz, 1H), 4.96-4.78 (m, 3H), 4.36 (q, J = 7.2 Hz, 1H), 3.92 (dd, J = 49.8, 10.4 Hz, 2H), 2.71 (dd, J = 13.2, 8.7 Hz, 1H), 2.40 (dd, J = 13.2, 8.3 Hz, 1H), 1.55 (ddt, J = 36.2, 13.7, 6.8 Hz, 2H), 0.60 (ddt, J = 10.2, 7.6, 3.7 Hz, 1H), 0.41 (t, J = 7.9 Hz, 2H), 0.00 (d, J = 4.9 Hz, 2H). |
| 5 | 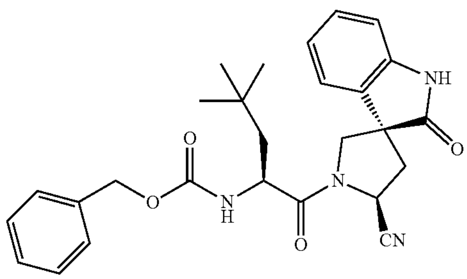 [SMILES: CC(C)(C)C[C@H](NC(=O)OCc1ccccc1)C(=O)N1C[C@]2(C[C@H]1C#N)C(=O)Nc1ccccc12] | [M + Na]⁺ 497.19 | ¹H NMR (400 MHz, Chloroform-d) δ 8.26 (s, 1H), 7.32-7.16 (m, 6H), 6.95-6.82 (m, 3H), 5.35 (d, J = 9.0 Hz, 1H), 5.01-4.73 (m, 3H), 4.41 (td, J = 8.5, 4.7 Hz, 1H), 4.19 (d, J = 10.2 Hz, 1H), 3.90 (d, J = 10.2 Hz, 1H), 2.79 (dd, J = 13.1, 9.0 Hz, 1H), 2.45 (dd, J = 13.1, 8.2 Hz, 1H), 1.72 (dd, J = 14.5, 4.8 Hz, 1H), 1.51 (dd, J = 14.5, 8.2 Hz, 1H), 0.90 (s, 9H). |
| 6 | 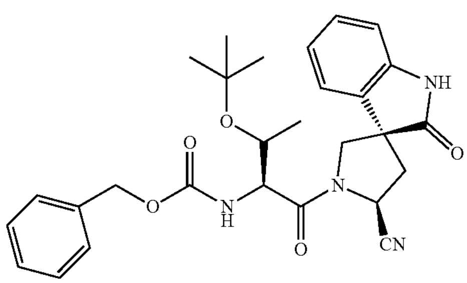 [SMILES: CC(OC(C)(C)C)[C@H](NC(=O)OCc1ccccc1)C(=O)N1C[C@]2(C[C@H]1C#N)C(=O)Nc1ccccc12] | [M + Na]⁺ 527.22 | ¹H NMR (400 MHz, Chloroform-d) δ 8.44 (s, 1H), 7.47-7.28 (m, 6H), 7.05 (t, J = 7.6 Hz, 1H), 6.96 (dd, J = 19.5, 7.7 Hz, 2H), 5.87 (d, J = 7.9 Hz, 1H), 5.09 (s, 2H), 4.36 (dd, J = 8.0, 3.7 Hz, 1H), 4.21-4.07 (m, 1H), 4.07-3.92 (m, 2H), 2.87 (dd, J = 13.1, 9.0 Hz, 1H), 2.54 (dd, J = 13.1, 8.2 Hz, 1H), 1.23 (s, 9H), 1.21 (d, J = 6.3 Hz, 3H). |
| 7 | 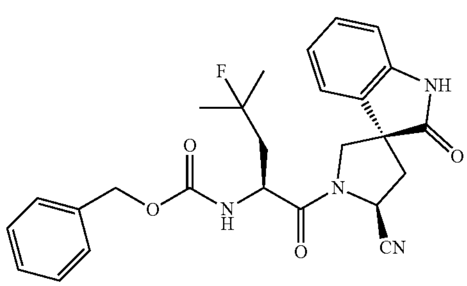 [SMILES: CC(C)(F)C[C@H](NC(=O)OCc1ccccc1)C(=O)N1C[C@]2(C[C@H]1C#N)C(=O)Nc1ccccc12] | [M + Na]⁺ 501.19 | ¹H NMR (400 MHz, Chloroform-d) δ 8.66 (s, 1H), 7.46-7.20 (m, 6H), 7.07-6.86 (m, 3H), 5.71 (d, J = 8.3 Hz, 1H), 5.08-4.88 (m, 3H), 4.63 (td, J = 8.1, 4.7 Hz, 1H), 4.26-4.13 (m, 1H), 4.00 (d, J = 10.3 Hz, 1H), 2.83 (dd, J = 13.2, 8.4 Hz, 1H), 2.52 (dd, J = 13.2, 8.3 Hz, 1H), 2.08-1.86 (m, 1H), 1.41 (dd, J = 21.4, 4.6 Hz, 6H), 1.26 (s, 1H). |

-continued
| Example # | Structure | MS | NMR |
|---|---|---|---|
| 8 | 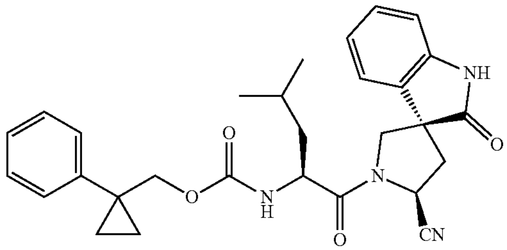 [SMILES: CC(C)C[C@H](NC(=O)OCC1(c2ccccc2)CC1)C(=O)N1C[C@]2(C[C@H]1C#N)C(=O)Nc1ccccc12] | [M + Na]⁺ 523.24 | ¹H NMR (400 MHz, Acetone-d₆) δ 9.69 (s, 1H), 7.38-7.17 (m, 5H), 7.15-7.06 (m, 1H), 7.06-6.92 (m, 2H), 6.56 (d, J = 8.4 Hz, 1H), 5.15 (t, J = 8.3 Hz, 1H), 4.42 (td, J = 9.2, 4.9 Hz, 1H), 4.23 (d, J = 10.3 Hz, 1H), 4.11 (d, J = 11.3 Hz, 1H), 4.10-3.93 (m, 2H), 2.83-2.56 (m, 2H), 1.84-1.53 (m, 3H), 0.94 (m, 8H), 0.92-0.81 (m, 2H). |
| 9 | 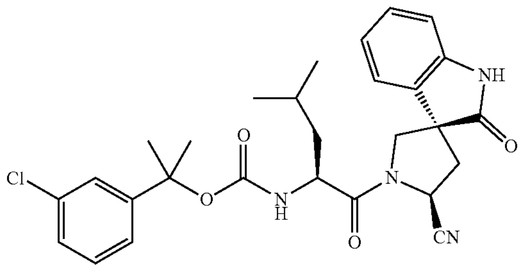 [SMILES: CC(C)C[C@H](NC(=O)OC(C)(C)c1cccc(Cl)c1)C(=O)N1C[C@]2(C[C@H]1C#N)C(=O)Nc1ccccc12] | [M − H]⁻ 521, 523 | ¹H NMR (400 MHz, Acetone-d₆) δ 9.66 (s, 1H), 7.40 (t, J = 1.9 Hz, 1H), 7.38-7.19 (m, 4H), 6.97 (dd, J = 7.5, 1.2 Hz, 2H), 6.93-6.84 (m, 1H), 6.66 (d, J = 8.7 Hz, 1H), 5.11 (t, J = 8.4 Hz, 1H), 4.35 (td, J = 9.5, 4.7 Hz, 1H), 4.14 (d, J = 10.4 Hz, 1H), 3.93 (d, J = 10.3 Hz, 1H), 2.68 (m, 2H), 1.80 (m, 1H), 1.66 (m, 7H), 1.58(m, 1H), 0.98 (d, J = 6.6 Hz, 3H), 0.91 (d, J = 6.5 Hz, 3H). |
| 10 | 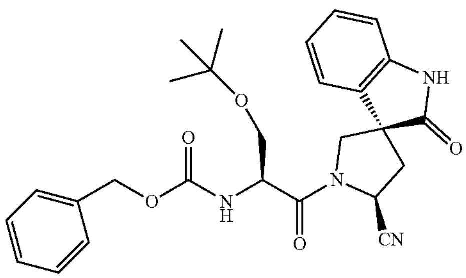 [SMILES: CC(C)(C)OC[C@H](NC(=O)OCc1ccccc1)C(=O)N1C[C@]2(C[C@H]1C#N)C(=O)Nc1ccccc12] | [M + Na]⁺ 513.20 | |
Example 11 & 12
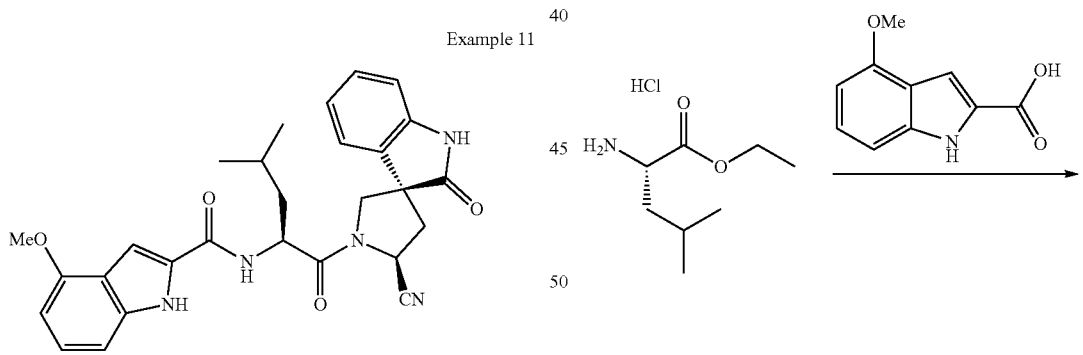
Example 11
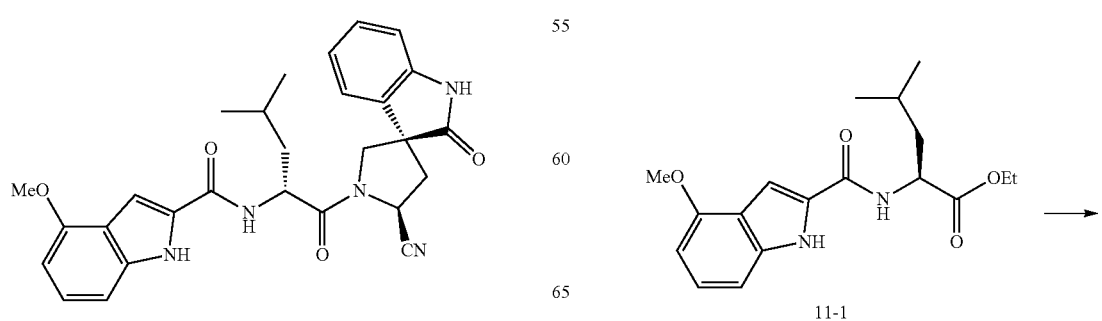
Example 12
11-1

-continued

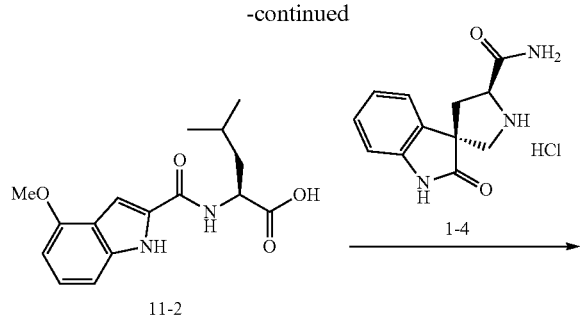

11-2

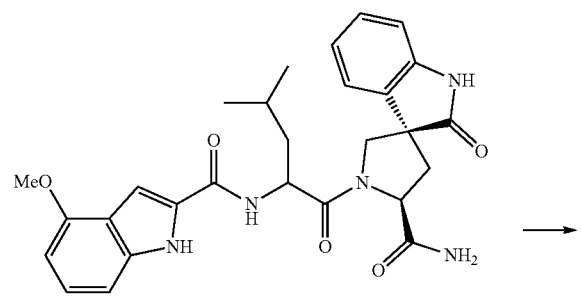

11-3

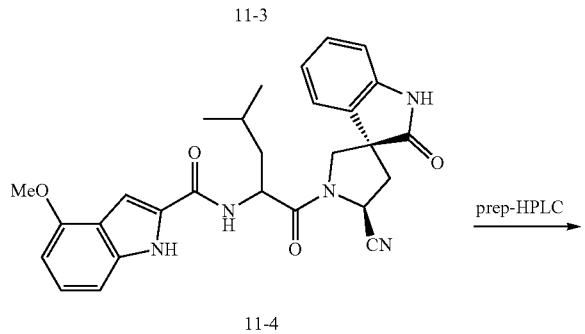

11-4

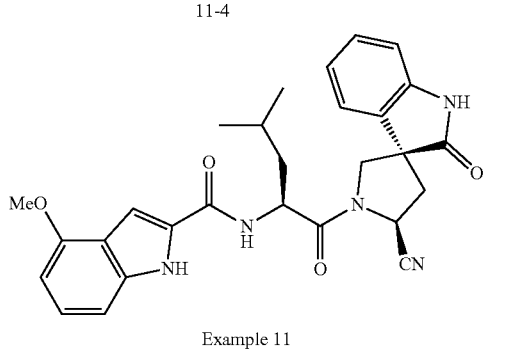

Example 11

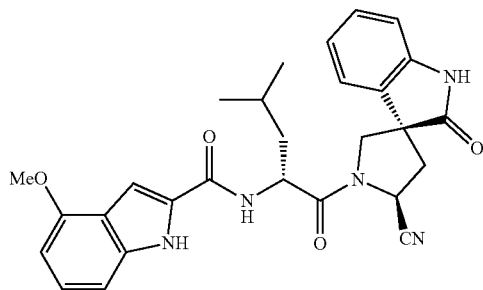

Example 12

Step 1

4-methoxy-1H-indole-2-carboxylic acid (1 g, 5.23 mmol) was dissolved in THF (25 mL). ethyl L-leucinate hydrochloride (1.024 g, 5.23 mmol), hunig's base (2.3 mL, 13.08 mmol), DMAP (0.032 g, 0.262 mmol), and HATU (2.0 g, 5.23 mmol) were added sequentially.

The mixture was stirred at rt for 1.5 h, quenched with water, and extracted with MTBE. The organic layer was washed with brine, dried with MgSO$_4$, and concentrated in vacuo. Purification of the residue on silica gel with 0-50% EtOAc/cyclohexane provided compound (11-1) (1.47 g, 4.42 mmol, 85% yield).

Step 2

Compound (11-1) (1.47 g, 4.42 mmol) was dissolved in THF (29.5 mL) and water (14.74 mL). At 0° C. LiOH—H$_2$O (0.278 g, 6.63 mmol) was added. The mixture was stirred vigorously at 0° C. for 30 min, quenched with 1 M HCl (6.6 mL), and extracted with EtOAc. The organic layer was washed with brine, dried over MgSO$_4$, and concentrated in vacuo. Purification of the residue on silica gel with 0-15% MeOH/DCM provided compound (11-2) (1.32 g).

Step 3

Compound (1-4) (50 mg, 0.187 mmol) and compound (11-2) (56.8 mg, 0.187 mmol) was dissolved in THF (1.6 mL) and DMF (0.3 mL). hunig's base (98 µl, 0.560 mmol) and HATU (56.8 mg, 0.149 mmol) were added. The mixture was stirred at rt for 30 min, quenched with water, and extracted with EtOAc. The organic layer was loaded on silica gel and eluted with 0-50% acetone/cyclohexane to provide compound (11-3) (75 mg, 0.145 mmol, 78% yield) as a mixture of two diastereomers.

Step 4

To a suspension of compound (11-3) (67 mg, 0.129 mmol) in DCM (1.3 mL) was added at 0° C. triethylamine (144 µl, 1.036 mmol) and TFAA (73.1 µl, 0.518 mmol). The mixture was warmed to rt and stirred for 10 min. The reaction mixture was diluted with DCM and quenched with sat. NaHCO$_3$. The organic layer was loaded on silica gel and eluted with 0-50% EtOAc/cyclohexane to afford compound (11-4) (48 mg, 0.096 mmol, 74.2% yield) as a mixture of two diastereomers.

Step 5

Purification of compound (11-4) (5 mg) on prep-HPLC with 20-85% MeCN/H$_2$O with 0.1% formic acid provided Example 11 (1.8 mg) and Example 12 (1.9 mg).

Example 11: $^1$H NMR (400 MHz, Acetone-d$_6$) δ 10.47 (s, 1H), 9.56 (s, 1H), 7.74 (d, J=8.1 Hz, 1H), 7.21 (d, J=2.2 Hz, 1H), 7.10-6.89 (m, 5H), 6.85 (d, J=7.7 Hz, 1H), 6.76 (td, J=7.5, 1.0 Hz, 1H), 6.41 (dd, J=7.3, 1.1 Hz, 1H), 5.03 (t, J=8.2 Hz, 1H), 4.84-4.74 (m, 1H), 4.23 (d, J=10.2 Hz, 1H), 3.91 (d, J=10.3 Hz, 1H), 3.81 (s, 3H), 2.56 (td, J=13.5, 8.2 Hz, 2H), 1.71 (ddd, J=14.5, 9.9, 3.9 Hz, 2H), 1.58 (ddd, J=13.8, 9.7, 4.9 Hz, 1H), 0.86 (dd, J=11.9, 6.4 Hz, 6H). [M+Na] m/e 522.19.

Example 12: $^1$H NMR (400 MHz, Acetone-d$_6$) δ 10.75 (s, 0.33H), 10.59 (s, 0.67H), 9.58 (s, 0.67H), 9.54 (s, 0.33H), 8.10 (d, J=7.8 Hz, 0.33H), 7.90 (d, J=8.7 Hz, 0.67H), 7.34-6.71 (m, 8H), 6.42 (m, 1H), 5.90 (t, J=8.0 Hz, 0.33H), 5.06 (t, J=8.3 Hz, 0.67H), 4.98 (ddd, J=11.3, 7.7, 4.0 Hz, 0.33H), 4.83 (td, J=9.1, 4.7 Hz, 0.67H), 4.00 (dd, J=11.7, 1.4 Hz, 0.39H), 3.97-3.87 (m, 1.41H), 3.81 (m, 3H), 3.51 (d, J=11.7 Hz, 0.39H), 2.65-2.49 (m, 1H), 1.91 (s, 2H), 1.71-1.51 (m, 2H), 0.96-0.90 (m, 2H), 0.75 (dd, J=6.3, 4.1 Hz, 4H). [M+Na] m/e 522.19.

The following examples were prepared employing similar protocol as described above.

| Example # | Structure | MS | NMR |
|---|---|---|---|
| 13 | 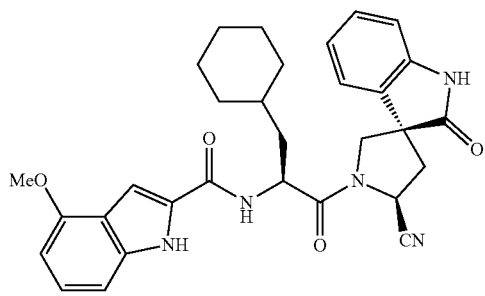 [SMILES: COc1cccc2[nH]c(C(=O)N[C@@H](CC3CCCCC3)C(=O)N3C[C@]4(C[C@H]3C#N)C(=O)Nc3ccccc34)cc12] | [M + H]+ 540.23 | 1H NMR (400 MHz, Chloroform-d) δ 8.92 (s, 1H), 7.86 (s, 1H), 7.18-7.08 (m, 2H), 7.04 (dd, J = 2.2, 0.9 Hz, 1H), 6.95-6.76 (m, 4H), 6.44 (d, J = 7.7 Hz, 1H), 4.99 (t, J = 8.6 Hz, 1H), 4.89-4.79 (m, 1H), 4.17 (t, J = 9.4 Hz, 1H), 3.95 (d, J = 10.3 Hz, 1H), 3.89 (s, 3H), 2.82 (dd, J = 13.1, 8.9 Hz, 1H), 2.48 (dd, J = 13.1, 8.2 Hz, 1H), 1.77 (d, J = 12.8 Hz, 1H), 1.74-1.56 (m, 6H), 1.37 (s, 1H), 1.19 (d, J = 1.6 Hz, 4H), 1.14-1.01 (m, 1H), 0.89-0.76 (m, 1H). |
| 14 | 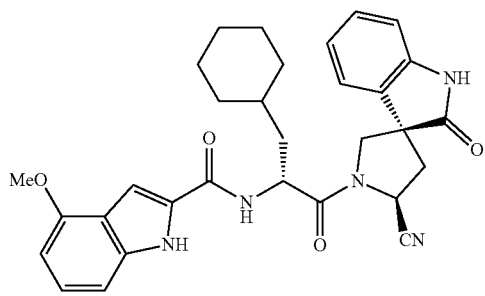 [SMILES: COc1cccc2[nH]c(C(=O)N[C@H](CC3CCCCC3)C(=O)N3C[C@]4(C[C@H]3C#N)C(=O)Nc3ccccc34)cc12] | [M + H]+ 540.26 | |
| 15 | 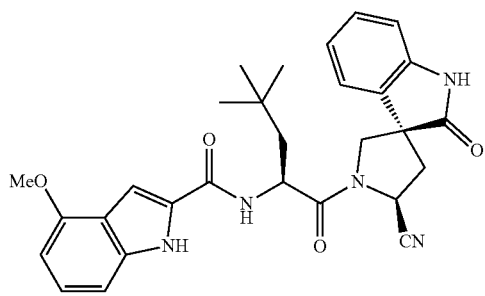 [SMILES: COc1cccc2[nH]c(C(=O)N[C@@H](CC(C)(C)C)C(=O)N3C[C@]4(C[C@H]3C#N)C(=O)Nc3ccccc34)cc12] | [M + H]+ 514.21 | |
| 16 | 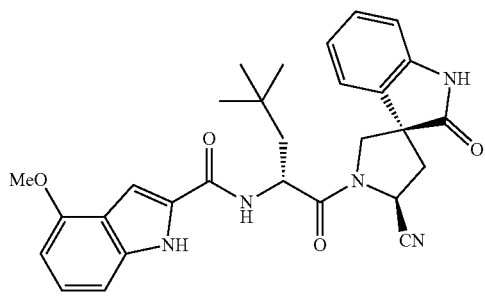 [SMILES: COc1cccc2[nH]c(C(=O)N[C@H](CC(C)(C)C)C(=O)N3C[C@]4(C[C@H]3C#N)C(=O)Nc3ccccc34)cc12] | [M + Na]+ 536.22 | |

Example 17

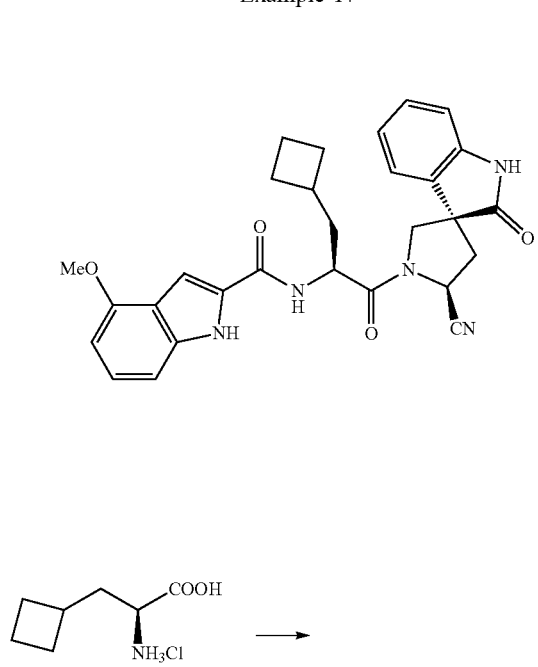

Step 1

To a mixture of (2S)-2-amino-3-cyclobutylpropanoic acid hydrochloride (0.359 g, 2 mmol) and NaOH (240 mg, 6.00 mmol) in toluene/water (4 mL/4 mL) at 0° C. was added Cbz-Cl (0.314 ml, 2.200 mmol). After stirring at rt for 2 h, the two layers were separated and the aqueous layer was washed with MBTE. The aqueous layer was then treated with 1 M HCl solution to PH~2. The resulting mixture was extracted with EtOAc. The collected organic layer was washed with brine, dry over $Na_2SO_4$, filtered, and concentrated to give compound (17-1) (0.46 g, 1.659 mmol, 83% yield).

Step 2

To a mixture of compound (17-1) (104 mg, 0.374 mmol), compound (1-4) (80 mg, 0.299 mmol), and DIPEA (183 µl, 1.046 mmol) in DCM/DMF (1.0/0.5 mL) at rt was added HATU (136 mg, 0.359 mmol). The mixture was stirred at rt for 20 h, quenched with water, and extracted with EtOAc. The collected organic layer was washed with 1 N HCl, sat $NaHCO_3$, brine, and dried over $Na_2SO_4$ and filtered. The filtrate was concentrated in vacuo. Purification of the residue on silica gel column provided compound (17-2) (98 mg, 0.200 mmol, 66.9% yield). [M–H]⁻, 489.16

Step 3

A suspension of (17-2) (25 mg, 0.051 mmol) and Pd—C (5.42 mg, 5.10 µmol) in MeOH (1 mL) was treated with 1 atm $H_2$ for 40 mins. The mixture was diluted with DCM, filtered through celite, washed with DCM, and concentrated in vacuo. The product (17-3) was used in next step directly. [M–H]⁻, 355.15

Step 4

To a suspension of 4-methoxy-1H-indole-2-carboxylic acid (15 mg, 0.077 mmol), compound (17-3) (18 mg, 0.051 mmol) and HATU (0.029 g, 0.077 mmol) in DCM (0.3 mL) was added DIPEA (0.031 ml, 0.179 mmol) in DMF (0.3 ML). The mixture was stirred at rt for 1 h, quenched with water, and extracted with EtOAc. The organic layer was washed with 1 N HCl, sat $NaHCO_3$, brine, dried over $Na_2SO_4$, and concentrated in vacuo. Purification of the residue with silica gel column conc afforded compound (17-4) (19 mg, 0.036 mmol, 70.3% yield). [M−H]⁻, 528.18

Step 5

To a mixture of compound (17-4) (19 mg, 0.036 mmol) and Et3N (60.0 µl, 0.431 mmol) in DCM (0.6 mL) at 0° C. was added TFAA (30.4 µl, 0.215 mmol). The mixture was warmed to rt and stirred for 1 h. The reaction was quenched with cold sat. NaHCO₃ and extracted with EtOAc. The organic layer was washed with 1 N HCl, sat NaHCO3 and brine, dried over Na₂SO₄, and concentrated. Purification of the residue with silica gel column provided Example 17 (12 mg, 0.023 mmol, 65.4% yield). [M−H]⁻ 510.17; ¹H NMR (400 MHz, Methanol-d₄) δ 7.26 (d, J=0.9 Hz, 1H), 7.22-7.10 (m, 3H), 7.02 (d, J=8.3 Hz, 1H), 6.99-6.89 (m, 2H), 6.53 (d, J=7.7 Hz, 1H), 5.17 (t, J=7.9 Hz, 1H), 4.71 (dd, J=8.0, 6.4 Hz, 1H), 4.30 (d, J=10.5 Hz, 1H), 4.08 (d, J=10.5 Hz, 1H), 3.96 (s, 3H), 2.75-2.62 (m, 2H), 2.52 (hept, J=7.7 Hz, 1H), 2.20-2.12 (m, 3H), 2.15-2.02 (m, 1H), 2.05-1.88 (m, 2H), 1.90-1.80 (m, 1H), 1.83-1.70 (m, 1H).

The following examples were prepared employing similar protocol as described above.

| Example # | Structure | MS | NMR |
|---|---|---|---|
| 18 | 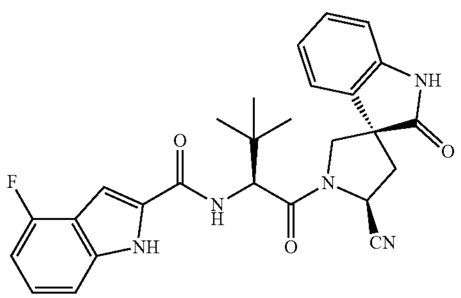 [SMILES: CC(C)(C)[C@H](NC(=O)c1cc2c(F)cccc2[nH]1)C(=O)N1C[C@]2(C[C@H]1C#N)C(=O)Nc1ccccc12] | [M − H]⁻ 486.15 | ¹H NMR (400 MHz, Acetone-d6) δ 10.79 (s, 1H), 9.55 (s, 1H), 7.51 (d, J = 9.0 Hz, 1H), 7.34 (dd, J = 2.2, 0.9 Hz, 1H), 7.21 (dd, J = 8.3, 0.8 Hz, 1H), 7.13-6.96 (m, 2H), 6.94-6.87 (m, 1H), 6.83 (dt, J = 7.8, 0.9 Hz, 1H), 6.72-6.62 (m, 2H), 5.06 (t, J = 8.2 Hz, 1H), 4.71 (d, J = 9.0 Hz, 1H), 4.20 (dd, J = 10.6, 1.0 Hz, 1H), 3.96 (d, J = 10.5 Hz, 1H), 2.69-2.50 (m, 2H), 1.04 (s, 9H). |
| 19 | 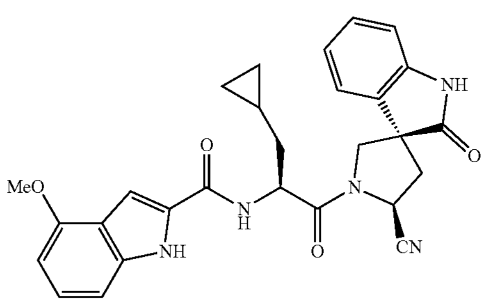 [SMILES: COc1cccc2[nH]c(C(=O)N[C@@H](CC3CC3)C(=O)N3C[C@]4(C[C@H]3C#N)C(=O)Nc3ccccc34)cc12] | [M + Na]⁺ 520.17 | ¹H NMR (500 MHz, Chloroform-d) δ 9.28 (s, 1H), 8.51 (s, 1H), 7.44-7.25 (m, 1H), 7.05-6.92 (m, 3H), 6.82 (d, J = 8.3 Hz, 1H), 6.76-6.60 (m, 3H), 6.31 (d, J = 7.7 Hz, 1H), 4.93 (t, J = 8.4 Hz, 1H), 4.78 (q, J = 7.1 Hz, 1H), 4.05 (d, J = 10.4 Hz, 1H), 3.88 (d, J = 10.4 Hz, 1H), 3.76 (s, 3H), 2.69 (dd, J = 13.2, 8.7 Hz, 1H), 2.35 (dd, J = 13.2, 8.3 Hz, 1H), 1.66 (ddt, J = 46.7, 13.5, 6.9 Hz, 2H), 0.64 (dq, J = 12.7, 7.4, 6.3 Hz, 1H), 0.47-0.30 (m, 2H), 0.00 (d, J = 4.9 Hz, 2H). |
| 20 | 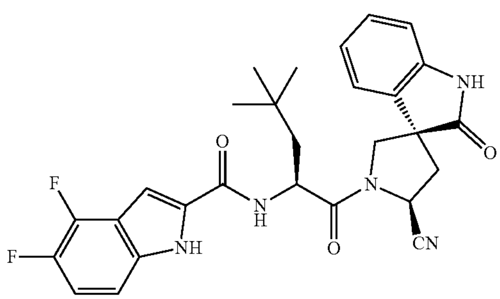 [SMILES: CC(C)(C)C[C@H](NC(=O)c1cc2c(F)c(F)ccc2[nH]1)C(=O)N1C[C@]2(C[C@H]1C#N)C(=O)Nc1ccccc12] | [M + Na]⁺ 542.18 | ¹H NMR (400 MHz, Acetone-d₆) δ 7.39 (d, J = 0.9 Hz, 1H), 7.35-7.25 (m, 1H), 7.25-7.11 (m, 2H), 7.11-7.02 (m, 1H), 6.95 (d, J = 7.8 Hz, 1H), 6.82 (td, J = 7.6, 1.1 Hz, 1H), 5.16 (t, J = 8.3 Hz, 1H), 4.98 (dd, J = 8.6, 4.1 Hz, 1H), 4.38 (d, J = 10.3 Hz, 1H), 4.05 (d, J = 10.3 Hz, 1H), 3.27 (d, J = 2.2 Hz, 1H), 2.77-2.62 (m, 2H), 1.96-1.74 (m, 2H), 1.03 (s, 9H). |
| 21 | 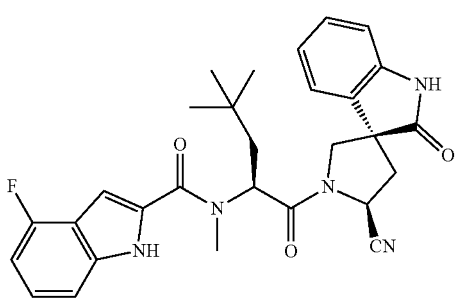 | [M + H]⁺ 502.20 | |

| Example # | Structure | MS | NMR |
|---|---|---|---|
| 22 | 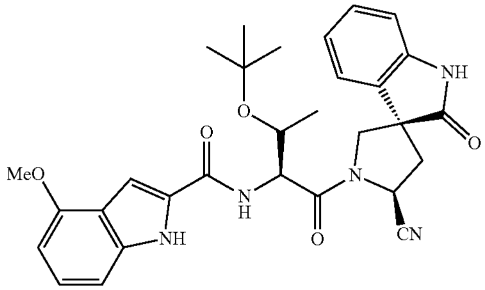 [SMILES: COc1cccc2[nH]c(C(=O)N[C@H](C(=O)N3C[C@]4(C[C@H]3C#N)C(=O)Nc3ccccc34)C(C)OC(C)(C)C)cc12] | [M + H]+ 544.25 | |
Example 23
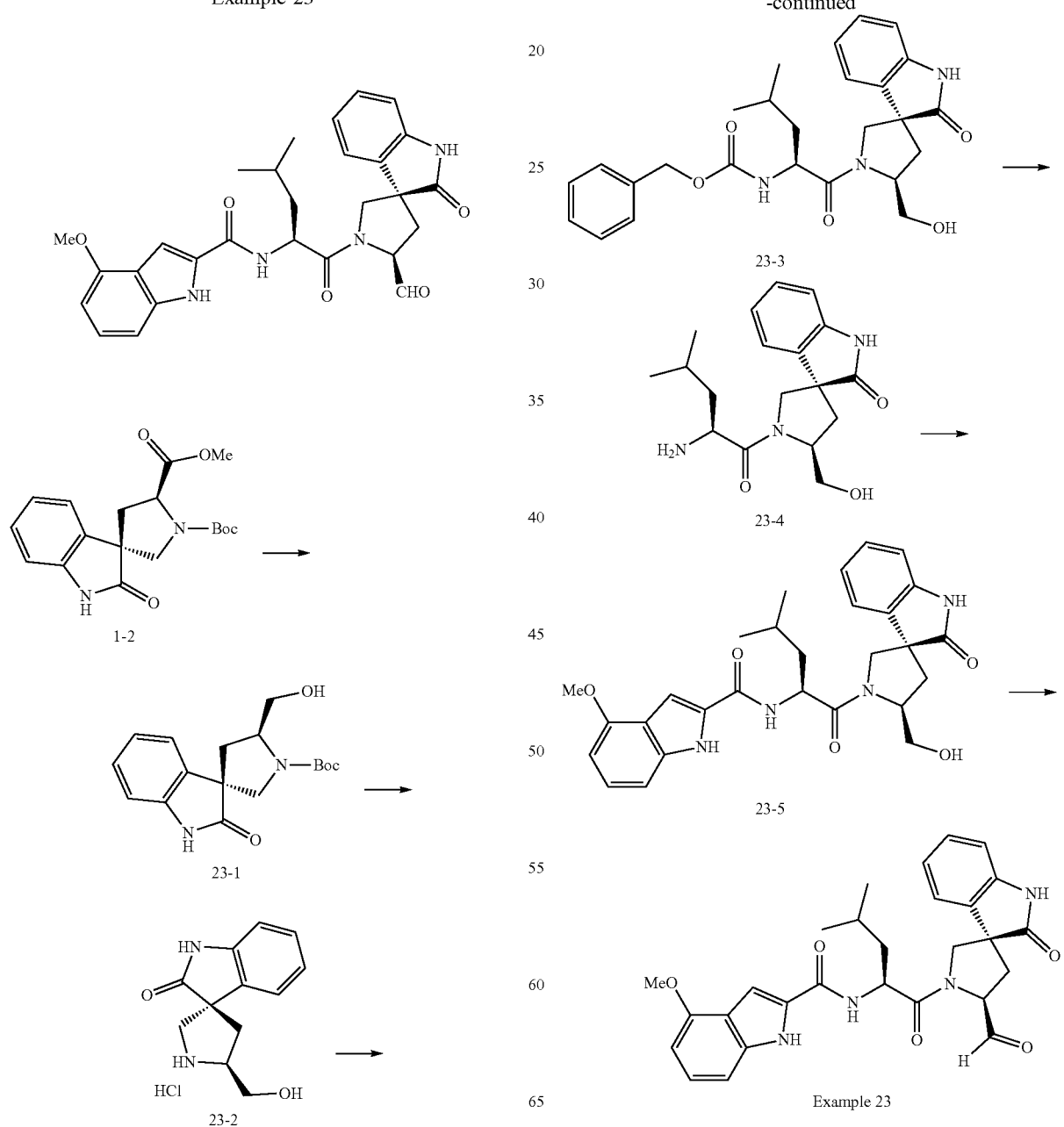

Step 1
To a solution of compound (1-2) (2.5 g, 7.22 mmol) in THF (24.06 mL) was added dropwise a solution of 2M LiBH$_4$ in THF (10.83 mL, 21.65 mmol). The mixture was stirred at rt for 2 hrs and the majority of THF was removed in vacuo. The reaction was quenched carefully with 1N HCl to pH=5-6 (~22 mL) and extracted with EtOAc (3×40 mL). The combined organic layers were washed with sat NaHCO$_3$, brine, dried and concentrated. Purification of the residue on silica gel with 0-50% EtOAc/Cyclohexane provided the desired alcohol (23-1) (1.54 g, 67% yield).

Step 2
Compound (23-1) (0.5 g, 1.570 mmol) was dissolved in a solution of 4M HCl in dioxane (3.93 mL, 15.70 mmol). The mixture was stirred at rt for 1 hrs and concentrated to dryness. Compound (23-2) (492 mg, 80% yield) was obtained as a yellow solid. LC-MS, ES+: 218.85 [M+1].

Step 3
To a solution of compound (23-2) (960 mg, 3.13 mmol) and ((benzyloxy)carbonyl)-L-leucine (913 mg, 3.44 mmol) in dry DMF (15.64 mL) at 0° C. was added HATU (1546 mg, 4.07 mmol) and Hunig's base (1912 µl, 10.95 mmol). The resulting mixture was stirred at 0° C. for 1 h, diluted with EtOAc, and washed with 10% citric acid, water, and brine. The organic layer was dried and concentrated. Purification of the residue on silica gel with 0-40% EtOAc/Cyclohexane provided 1.2 g of compound (23-3). LC-MS, ES+: 466.19 [M+1].

Step 4
Compound (23-3) (800 mg, 1.718 mmol) was dissolved in MeOH (17 mL). 10% Pd on carbon (40 mg, 0.038 mmol) was added. The mixture was stirred under hydrogen for 2.5 h, and filtered through a pad of Celite. Solvent was removed and the crude product (23-4) (543 mg, 1.638 mmol, 95% yield), was used for next step. [M+1] 332.20.

Step 5
Compound (23-4) (195 mg, 0.588 mmol) and 4-methoxy-1H-indole-2-carboxylic acid (118 mg, 0.618 mmol) was dissolved in CH$_2$Cl$_2$ (5.9 mL). At 0° C., hunig's base (308 µl, 1.765 mmol) and HATU (235 mg, 0.618 mmol) were added. The mixture was stirred at 0° C. for 30 min. The reaction was quenched with water and extracted with DCM. The organic layer was loaded on silica gel and eluted with 0-50% acetone/cyclohexane to afford compound (23-5) (213 mg, 0.422 mmol, 71.7% yield).

Step 6
In a flame dried flask, acetic anhydride (422 µl, 4.46 mmol) was added to anhydrous DMSO (3.10 mL) at rt. After stirring for 10 mins, compound (23-5) (150 mg, 0.297 mmol) was added in one portion. The mixture was stirred at rt for 6 h. The reaction was cooled to 0° C. and diluted with water (~8 mL). The white precipitate was collected by filtration, rinsed with water, and dried under vacuum. Purification of the solid on silica gel with 0-45% acetone/cyclohexane provided Example 23 as a colorless solid (112 mg, 75% yield). [M+H]$^+$ 503.16. $^1$H NMR (500 MHz, DMSO-d$_6$) δ 11.52 (d, J=2.3 Hz, 1H), 10.66 (s, 1H), 9.52 (d, J=2.1 Hz, 1H), 8.61 (d, J=7.7 Hz, 1H), 7.40-7.32 (m, 1H), 7.26 (d, J=7.9 Hz, 1H), 7.26-7.18 (m, 1H), 7.17-7.02 (m, 1H), 7.04-6.97 (m, 2H), 6.89 (d, J=8.9 Hz, 1H), 6.52 (t, J=8.4 Hz, 1H), 4.75 (s, 1H), 4.62 (td, J=8.1, 7.1, 3.8 Hz, 1H), 4.11 (d, J=10.5 Hz, 1H), 3.97 (d, J=10.5 Hz, 1H), 3.89 (s, 3H), 3.88 (d, J=7.4 Hz, 1H), 2.41 (dd, J=13.0, 9.0 Hz, 1H), 2.21 (dd, J=13.2, 6.2 Hz, 1H), 1.77 (m, 1H), 1.60 (m, 1H), 0.96 (d, J=7.0 Hz, 3H), 0.89 (d, J=7.0 Hz, 3H).

The following examples were prepared employing similar protocol as described above.

| Example # | Structure | MS | NMR |
|---|---|---|---|
| 24 | 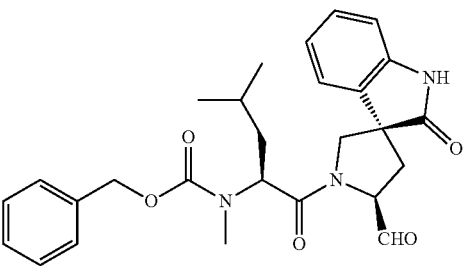 [SMILES: CC(C)C[C@@H](C(=O)N1C[C@]2(C[C@H]1C=O)C(=O)Nc1ccccc12)N(C)C(=O)OCc1ccccc1] | [M + H]$^+$ 476.2 | |
| 25 | 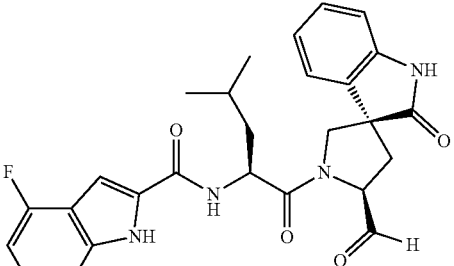 | [M + H]$^+$ 491.19 | 1H NMR (400 MHz, Acetone-d$_6$) δ 10.99 (s, 1H), 9.65 (d, J = 1.9 Hz, 1H), 9.64 (s, 1H), 8.06-7.96 (m, 1H), 7.42-7.32 (m, 3H), 7.32-7.17 (m, 2H), 7.12-6.90 (m, 2H), 6.81 (dd, J = 10.6, 7.8 Hz, 1H), 5.15-4.98 (m, 1H), 4.80-4.65 (m, 1H), 4.28 (d, J = 10.4 Hz, 1H), 4.13 (d, J = 10.4 Hz, 1H), 2.51 (dd, J = 13.1, 9.1 Hz, 1H), 2.37 (dd, J = 13.1, 6.1 Hz, 1H), 1.92-1.70 (m, 2H), 1.44 (s, 1H), 1.00 (dd, J = 6.5, 4.8 Hz, 6H). |

Example 26

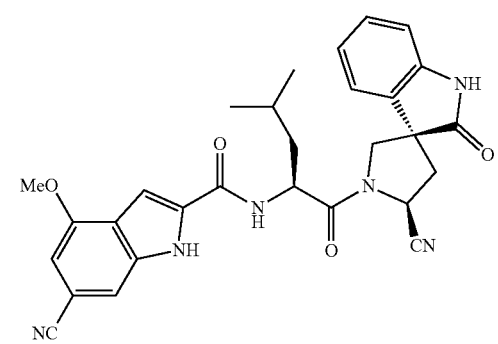 [SMILES: COc1cc(C#N)cc2[nH]c(C(=O)N[C@@H](CC(C)C)C(=O)N3C[C@]4(C[C@H]3C#N)C(=O)Nc3ccccc34)cc12]

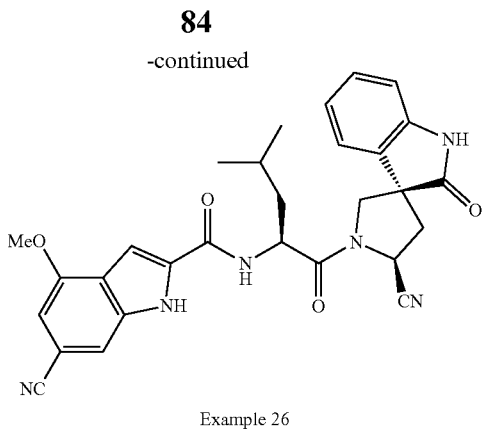

Example 26

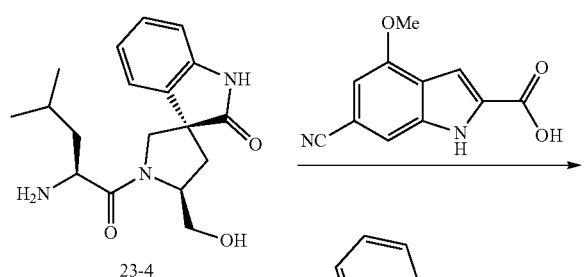

Step 1

Compound 23-4 (45 mg, 0.136 mmol) was dissolved in DCM (1.358 mL). DIPEA (48.5 µl, 0.272 mmol), 6-cyano-4-methoxy-1H-indole-2-carboxylic acid (32.3 mg, 0.149 mmol), and HATU (51.6 mg, 0.136 mmol) were added. The mixture was stirred at rt for 1 h, quenched with water, and extracted with DCM. The organic layer was loaded on silica gel and eluted with 0-50% acetone/cyclohexane to afford Compound 26-1 (22 mg, 0.042 mmol, 30.6% yield). [M-OH]$^+$, 512.20.

Step 2

Acetic anhydride (78 µl, 0.831 mmol) was added to DMSO (0.415 mL) at rt. The mixture was stirred at rt for 5 min, and transferred to a vial containing compound 26-1 (22 mg, 0.042 mmol). The reaction mixture was stirred at rt for 6 h, quenched with water at 0° C., and extracted with EtOAc. The organic layer was washed with water, brine, and concentrated. Purification of the residue on silica gel with 0-50% acetone/cyclohexane provided compound 26-2 (15 mg, 0.028 mmol, 68.4% yield). [M+H]$^+$, 528.21.

Step 3

Compound 26-2 (15 mg, 0.028 mmol) was dissolved in 2-propanol. A 1 M solution of hydroxylamine hydrochloride (56.9 µl, 0.057 mmol) in t-BuOH/H2O (1:1) was added. The mixture was stirred at rt for 30 min, quenched with aq NaHCO$_3$, and extracted with EtOAc. The organic layer was dried over Na$_2$SO$_4$, and concentrated in vacuo. The crude product, compound 26-3 (14 mg, 0.026 mmol, 91% yield) was used in the next step. [M+H]$^+$, 543.22

Step 4

To a vial containing compound 26-3 (14 mg, 0.026 mmol) was added MeCN (0.516 mL) and copper (II) acetate (1.406 mg, 7.74 µmol). The resulting mixture was stirred at 70° C. for 2 h, and concentrated in vacuo. Purification of the residue on silica gel with 0-50% EtOAc/cyclohexane, followed by prep-HPLC, provided Example 26 (2.8 mg, 5.34 µmol, 20.69% yield). [M+H]$^+$, 525.22; $^1$H NMR (400 MHz, Acetone-d$_6$) δ 11.06 (s, 1H), 9.57 (s, 1H), 7.96 (d, J=8.3 Hz, 1H), 7.45 (s, 1H), 7.32 (d, J=1.9 Hz, 1H), 7.08-6.92 (m, 2H), 6.84 (d, J=7.8 Hz, 1H), 6.77-6.68 (m, 2H), 5.03 (t, J=8.3 Hz, 1H), 4.84-4.75 (m, 1H), 4.23 (d, J=10.4 Hz, 1H), 3.91 (m, 5H), 2.58 (qd, J=13.3, 8.4 Hz, 2H), 1.72 (m, 2H), 1.61 (m, 1H), 0.85 (m, 6H).

The following examples were prepared employing similar protocol as described above.

| Example # | Structure | MS | NMR |
|---|---|---|---|
| 27 | 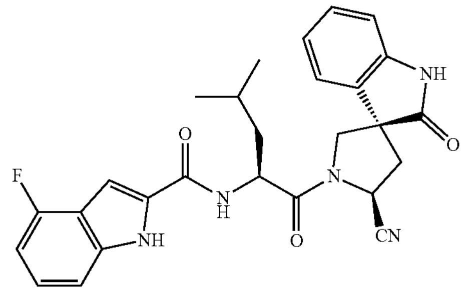 | [M + H]+ 488.19 | 1H NMR (400 MHz, Acetone-d6) δ 10.78 (s, 1H), 9.56 (s, 1H), 7.90 (d, J = 8.2 Hz, 1H), 7.29-7.19 (m, 2H), 7.12-6.93 (m, 3H), 6.83 (dt, J = 7.8, 0.8 Hz, 1H), 6.73 (td, J = 7.6, 1.1 Hz, 1H), 6.70-6.62 (m, 1H), 5.03 (t, J = 8.3 Hz, 1H), 4.81 (ddd, J = 9.6, 8.2, 4.7 Hz, 1H), 4.21 (dd, J = 10.5, 1.0 Hz, 1H), 3.97-3.87 (m, 1H), 2.66-2.49 (m, 2H), 1.78-1.64 (m, 2H), 1.58 (ddd, J = 13.8, 9.6, 5.0 Hz, 1H), 0.85 (m, 6H). |
| 28 | 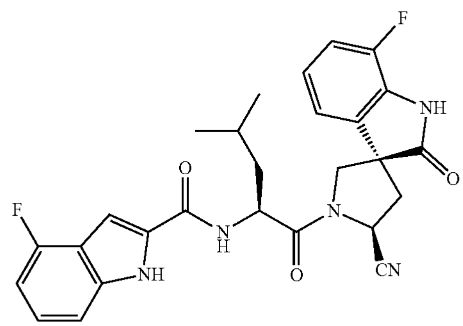 [SMILES: CC(C)C[C@H](NC(=O)c1cc2c(F)cccc2[nH]1)C(=O)N1C[C@]2(C[C@H]1C#N)C(=O)Nc1c(F)cccc12] | [M + H]+ 505.93 | 1H NMR (500 MHz, Acetone-d6) δ 10.90 (s, 1H), 10.10 (s, 1H), 8.01 (d, J = 8.2 Hz, 1H), 7.37-7.34 (m, 1H), 7.21 (m, 1H), 7.03-6.97 (m, 1H), 6.95 (d, J = 7.4 Hz, 1H), 6.85 (ddd, J = 8.4, 7.5, 4.8 Hz, 1H), 6.82-6.77 (m, 1H), 5.17 (t, J = 8.3 Hz, 1H), 4.93 (ddd, J = 9.6, 8.3, 4.7 Hz, 1H), 4.42 (dd, J = 10.6, 1.2 Hz, 1H), 4.06 (d, J = 10.5 Hz, 1H), 2.80-2.76 (m, 1H), 2.70 (dd, J = 13.3, 8.1 Hz, 1H), 1.86-1.78 (m, 2H), 1.71 (m, 1H), 0.97 (m, 6H). |

Example 29

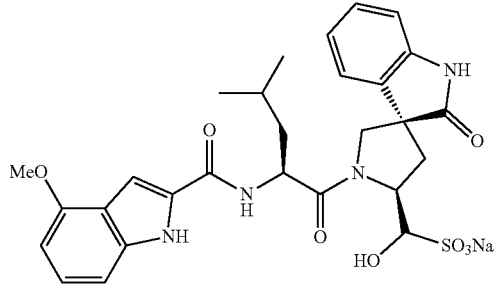

→

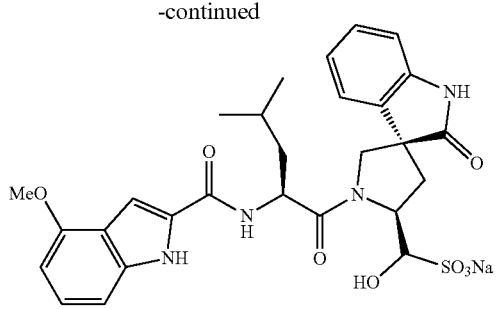

To a solution of Example 23 (45 mg, 0.090 mmol) in EtOH (2 mL) and water (0.2 mL) was added sodium bisulfite (9.32 mg, 0.090 mmol). The mixture was stirred at rt for 4 h and then concentrated. DCM was added to the residue and white solid precipitated. The collected solid was washed with acetone and dried to afford Example 29 as a white solid. [M-Na]− 583.0. 1H NMR (500 MHz, DMSO-d6) δ 11.42 (s, 1H), 10.57 (d, J=7.9 Hz, 1H), 9.88 (s, 1H), 8.47 (d, J=8.2 Hz, 1H), 7.35-7.31 (m, 1H), 7.14-7.05 (m, 2H), 7.02-6.96 (m, 1H), 6.86 (ddt, J=24.0, 15.0, 8.1 Hz, 3H), 6.50 (d, J=7.7 Hz, 1H), 5.65 (d, J=5.5 Hz, 1H), 4.83-4.78 (m, 1H), 4.70 (t, J=9.3 Hz, 2H), 3.96 (d, J=9.3 Hz, 1H), 3.90 (s, 3H), 3.61 (d, J=9.8 Hz, 1H), 2.79 (dd, J=13.1, 9.8 Hz, 1H), 1.81-1.67 (m, 3H), 0.99 (td, J=15.4, 7.0 Hz, 1H), 0.90 (d, J=6.4 Hz, 3H), 0.85 (d, J=6.1 Hz, 3H).

The following example was prepared employing similar protocol as described above.

| Example | Structure | MS |
|---|---|---|
| 30 | 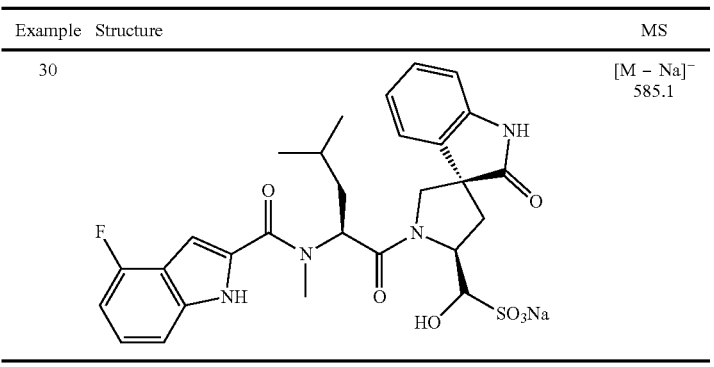 | [M − Na]⁻ 585.1 |

Example 31

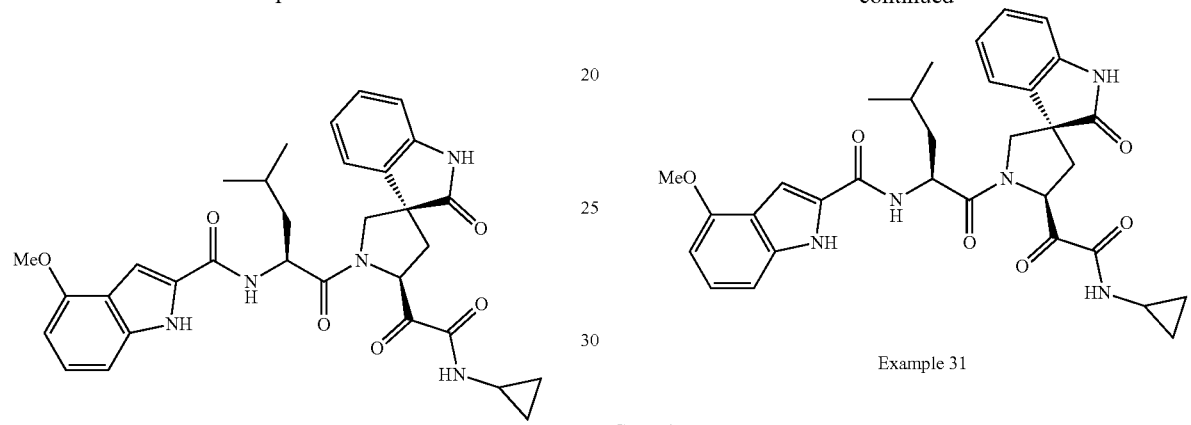

Example 31

Step 1

To Example 23 (18 mg, 0.036 mmol) at 0° C. was added acetic acid (2.4 µl, 0.041 mmol) and a solution of isocyanocyclopropane (2.64 mg, 0.039 mmol) in DCM (0.20 mL). The mixture was stirred at 0° C. to rt for 5 h. The reaction mixture was concentrated to dryness and redissolved in MeOH (0.35 mL). A 0.5 M solution of $K_2CO_3$ in water (179 µl, 0.090 mmol) was added. The mixture was stirred at rt for 2 h. MeOH was removed in vacuo and the aqueous layer was extracted with EtOAc (3×). The combined organic layer was washed with water and brine, dried, and concentrated. The crude product (31-1) was directly used in the next step. [M+1], 588.2.

Step 2

To a solution of compound (31-1) in DCM (0.360 mL) at 0° C. was added Dess-Martin Periodinane (0.023 g, 0.054 mmol). The mixture was stirred at 0° C. for 2.5 h. At 0° C., the reaction mixture was diluted with DCM, quenched with 10% $Na_2S_2O_3$, and washed with 5% $NaHCO_3$. The collected organic layer was washed with water and brine, dried, and concentrated. Purification of the residue on silica gel with 0-60% acetone/cyclohexane provided Example 31 (6.5 mg). [M−1]⁻ 584.07. ¹H NMR (400 MHz, Acetone-$d_6$) δ 10.62 (s, 1H), 9.67 (s, 1H), 7.90 (d, J=4.9 Hz, 1H), 7.78 (d, J=8.2 Hz, 1H), 7.31 (dd, J=2.3, 0.8 Hz, 1H), 7.29-7.10 (m, 4H), 7.14-6.95 (m, 2H), 6.92 (td, J=7.6, 1.1 Hz, 1H), 6.53 (dd, J=7.2, 1.2 Hz, 1H), 5.69-5.54 (m, 1H), 4.93 (td, J=8.4, 6.0 Hz, 1H), 4.34 (d, J=9.9 Hz, 1H), 4.02 (d, J=9.9 Hz, 1H), 3.94 (s, 3H), 4.00-3.86 (m, 1H), 2.92-2.78 (m, 1H), 2.52-2.38 (m, 2H), 1.89 (dt, J=12.9, 6.5 Hz, 1H), 1.72 (ddd, J=8.1, 5.7, 2.3 Hz, 2H), 1.13-0.93 (m, 6H), 0.83-0.65 (m, 4H).

The following examples were prepared employing similar protocol as described above.

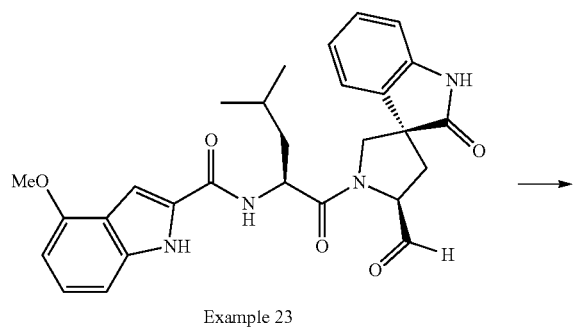

Example 23

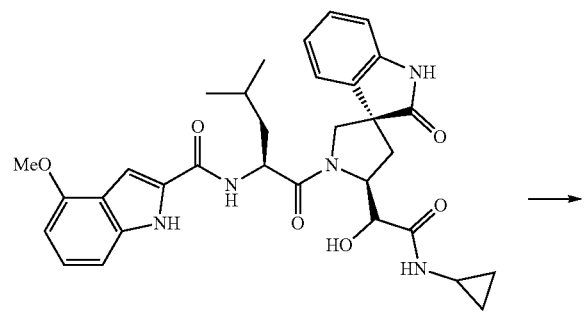

31-1

| Example # | Structure | MS | NMR |
|---|---|---|---|
| 32 | 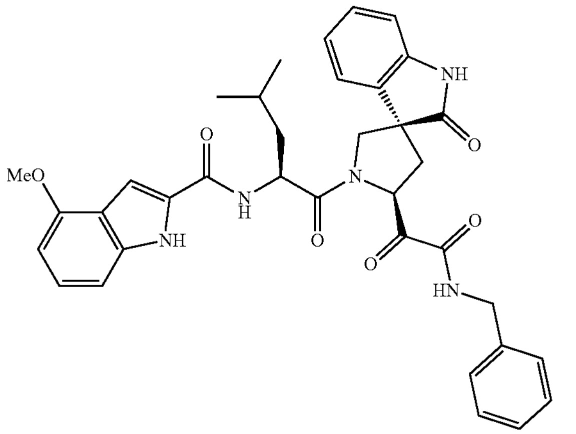 [SMILES: COc1cccc2[nH]c(C(=O)N[C@@H](CC(C)C)C(=O)N3C[C@]4(C[C@H]3C(=O)C(=O)NCc3ccccc3)C(=O)Nc3ccccc34)cc12] | [M − H]⁻ 634.0 | ¹H NMR (500 MHz, DMSO-d₆) δ 11.49 (d, J = 2.4 Hz, 1H), 10.74(s, 1H), 9.37 (t, J = 6.4 Hz, 1H), 8.53 (d, J = 7.5 Hz, 1H), 7.40 ? 7.26 (m, 4H), 7.28-7.20 (m, 3H), 7.15 (d, J = 7.3 Hz, 1H), 7.10 (t, J = 8.0 Hz, 1H), 7.06-6.88 (m, 3H), 6.51 (d, J = 7.7 Hz, 1H), 5.44 (dd, J = 10.5, 7.7 Hz, 1H), 4.71-4.63 (m, 1H), 4.39-4.28 (m, 2H), 4.19 (d, J = 10.2 Hz, 1H), 3.89 (s, 3H), 3.88-3.80 (m, 1H), 2.35-2.27 (m, 1H), 2.25 (dd, J = 12.6, 10.4 Hz, 1H), 1.80-1.64 (m, 2H), 1.50 (ddd, J = 13.5, 8.8, 4.3 Hz, 1H), 0.94 (d, J = 6.5 Hz, 3H), 0.88 (d, J = 6.5 Hz, 3H). |
| 33 | 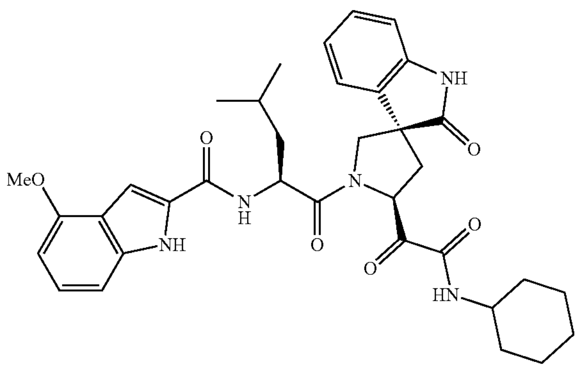 [SMILES: COc1cccc2[nH]c(C(=O)N[C@@H](CC(C)C)C(=O)N3C[C@]4(C[C@H]3C(=O)C(=O)NC3CCCCC3)C(=O)Nc3ccccc34)cc12] | [M − H]⁻ 626.1 | ¹H NMR (500 MHz, DMSO-d₆) δ 11.48 (d, J = 2.3 Hz, 1H), 10.73 (s, 1H), 8.64 (d, J = 8.4 Hz, 1H), 8.52 (d, J = 7.4 Hz, 1H), 7.35 (dd, J = 2.4, 0.9 Hz, 1H), 7.22 (qd, J = 7.5, 1.2 Hz, 1H), 7.13 (d, J = 7.5 Hz, 1H), 7.09 (t, J = 7.9 Hz, 1H), 7.03-6.90 (m, 3H), 6.50 (d, J = 7.7 Hz, 1H), 5.37 (dd, J = 10.3, 7.8 Hz, 1H), 4.66 (ddd, J = 10.6, 7.3, 4.1 Hz, 1H), 4.17 (d, J = 10.1 Hz, 1H), 3.89 (s, 3H), 3.87-3.79 (m, 1H), 3.56 (s, 1H), 2.34-2.21 (m, 2H), 1.77 (s, 1H), 1.70 (d, J = 12.1 Hz, 6H), 1.61-1.46 (m, 2H), 1.33 (q, J = 11.3 Hz, 2H), 1.26 (s, 3H), 0.94 (d, J = 6.6 Hz, 3H), 0.88 (d, J = 6.5 Hz, 3H). |
| 34 | 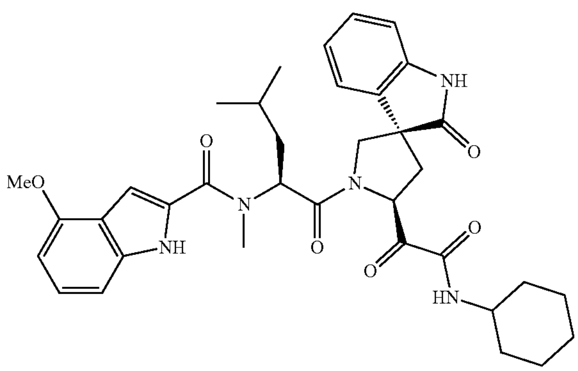 [SMILES: COc1cccc2[nH]c(C(=O)N(C)[C@@H](CC(C)C)C(=O)N3C[C@]4(C[C@H]3C(=O)C(=O)NC3CCCCC3)C(=O)Nc3ccccc34)cc12] | [M − H]⁻ 640.2 | ¹H NMR (500 MHz, DMSO-d₆) δ 11.44 (s, 1H), 10.70 (s, 1H), 8.69 (d, J = 8.4 Hz, 1H), 7.12 (dt, J = 24.9, 8.1 Hz, 3H), 6.93 (q, J = 7.6, 6.8 Hz, 2H), 6.85 (d, J = 7.8 Hz, 1H), 6.70 (s, 1H), 6.50 (d, J = 7.6 Hz, 1H), 5.40 (dd, J = 10.2, 8.0 Hz, 1H), 5.33 (s, 1H), 3.93 (s, 1H), 3.89 (s, 3H), 3.84 (d, J = 10.0 Hz, 1H), 3.57 (d, J = 10.5 Hz, 2H), 3.25 (s, 3H), 2.34 (dd, J = 12.9, 8.2 Hz, 1H), 1.71 (s, 6H), 1.57 (s, 3H), 1.35-1.22 (m, 5H), 0.96 (d, J = 6.3 Hz, 3H), 0.90 (d, J = 6.1 Hz, 3H). |
| 35 | 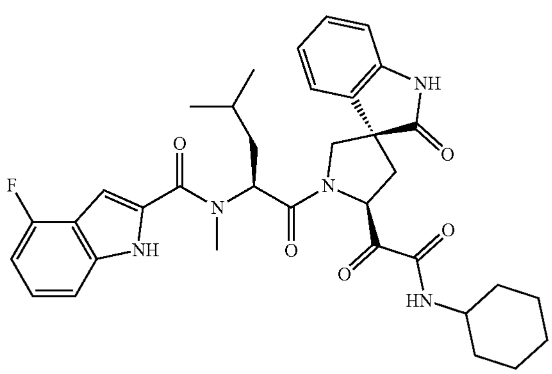 [SMILES: CC(C)C[C@@H](C(=O)N1C[C@]2(C[C@H]1C(=O)C(=O)NC1CCCCC1)C(=O)Nc1ccccc12)N(C)C(=O)c1cc2c(F)cccc2[nH]1] | [M − H]⁻ 628.02 | |

| Example # | Structure | MS | NMR |
|---|---|---|---|
| 36 | 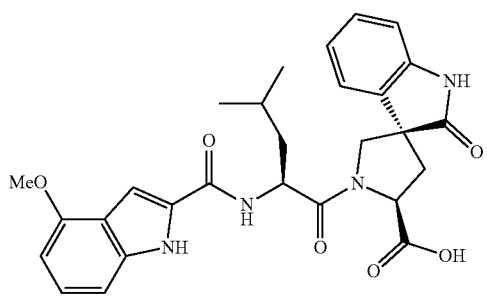 [SMILES: COc1cccc2[nH]c(C(=O)N[C@@H](CC(C)C)C(=O)N3C[C@]4(C[C@H]3C(=O)O)C(=O)Nc3ccccc34)cc12] | [M − H]⁻ 586.12 | $^1$H NMR (500 MHz, Acetone-$d_6$) δ 10.72 (s, 1H), 9.64 (s, 1H), 7.95 (d, J = 4.9 Hz, 1H), 7.32 (d, J = 8.3 Hz, 1H), 7.23-7.15 (m, 2H), 7.11 (t, J = 7.7 Hz, 1H), 6.96-6.86 (m, 3H), 6.79 (dd, J = 10.5, 7.7 Hz, 1H), 5.60 (dd, J = 10.3, 8.1 Hz, 1H), 5.53 (t, J = 7.5 Hz, 1H), 4.21 (d, J = 9.5 Hz, 1H), 3.96 (d, J = 10.1 Hz, 1H), 3.44 (s, 3H), 2.93-2.87 (m, 1H), 2.44 (dd, J = 8.1, 1.4 Hz, 1H), 2.38 (dd, J = 12.7, 10.3 Hz, 1H), 1.82 (dt, J = 14.0, 7.2 Hz, 1H), 1.79-1.67 (m, 2H), 1.67-1.58 (m, 1H), 0.99 (dd, J = 27.9, 6.6 Hz, 6H), 0.84-0.69 (m, 4H). |

Example 37

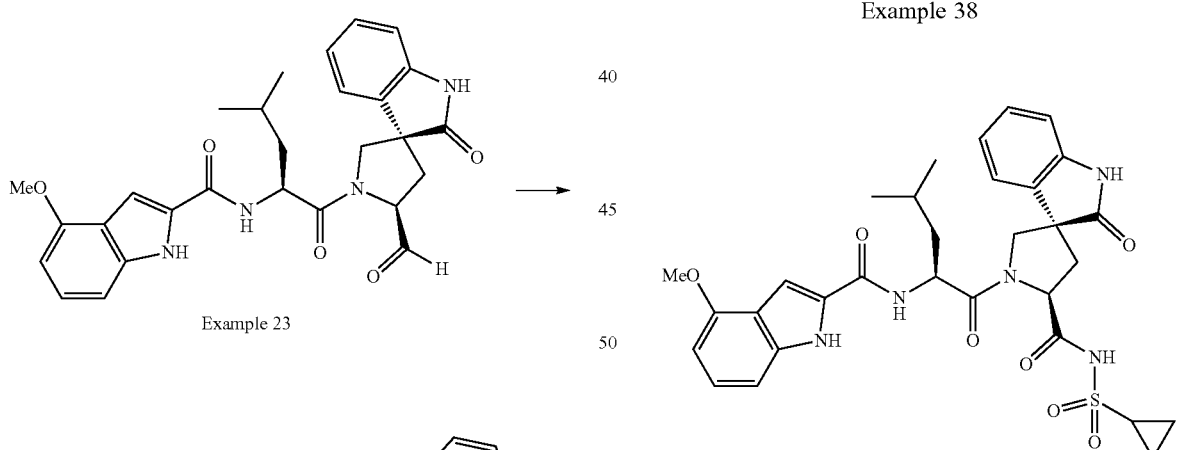

Example 23

Example 37

To a mixture of Example 23 (105 mg, 0.209 mmol) in tert-butanol (2.79 mL) at rt was added 2-methyl-2-butene, 2M in THF (2.09 mL, 4.18 mmol) to achieve a clear solution. A solution of sodium chlorite (236 mg, 2.089 mmol) and sodium phosphate monobasic (251 mg, 2.089 mmol) in water (1.39 mL) was added dropwise over 10 minutes. After stirring at rt for 1 h, the reaction mixture was concentrated to remove most of the volatiles. The resulting mixture was diluted with EtOAc, washed with water, brine, dried and concentrated. Purification of the residue on silica gel chromatography with 0-10% MeOH/DCM provided Example 37 (40 mg, 36% yield). LC-MS, ES⁻: 516.94 [M−H]⁻.

Example 38

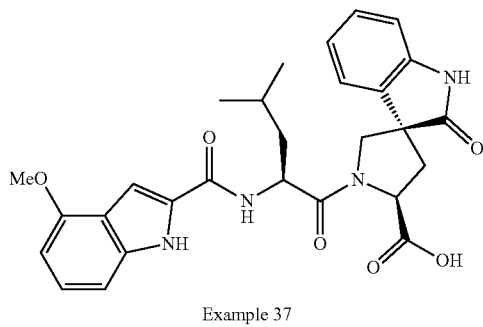

A solution of Example 37 (18 mg, 0.035 mmol), cyclopropanesulfonamide (8.41 mg, 0.069 mmol), EDCI (7.2 mg, 0.038 mmol) and DMAP (4.59 mg, 0.038 mmol) in dry DCM was stirred at rt for 4 hrs. The reaction mixture was diluted with DCM, washed with brine, dried, and concentrated. The residue was purified by chromatography on silica gel using 0 to 50% acetone/cyclohexane to give Example 38 (3.5 mg, 16% yield) as a white solid. LC-MS, ES−: 619.80 [M−H]⁻.

Example 39

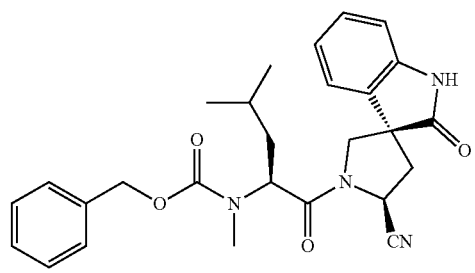 [SMILES: CC(C)C[C@@H](C(=O)N1C[C@]2(C[C@H]1C#N)C(=O)Nc1ccccc12)N(C)C(=O)OCc1ccccc1]

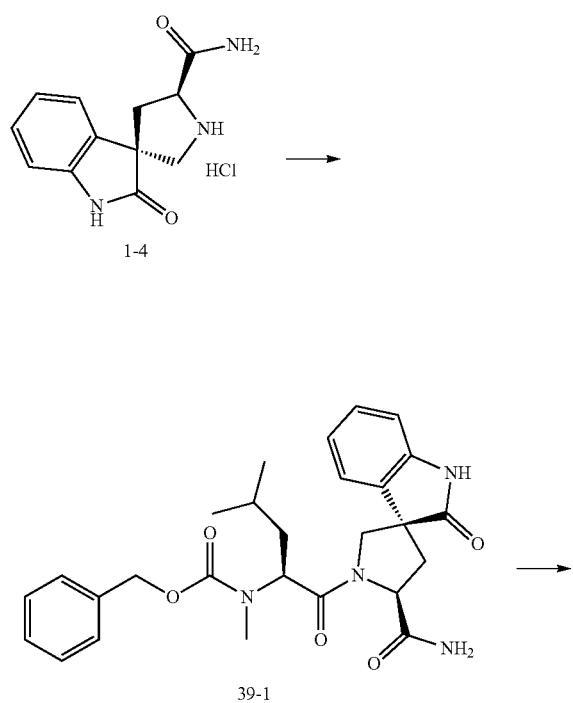

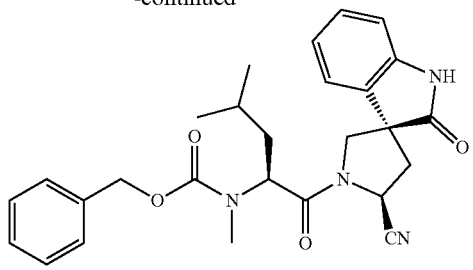

Example 39

Step 1

Compound (1-4) (300 mg, 1.121 mmol) and N-((benzyloxy)carbonyl)-N-methyl-L-leucine (344 mg, 1.233 mmol) was taken up in $CH_2Cl^2$ (5 ml) and DMF (1 ml). 4-methylmorpholine (246 µl, 2.241 mmol) and HATU (469 mg, 1.233 mmol) were added. The mixture was stirred at rt for 1 h, diluted with DCM (30 mL), and washed with sat. NaHCO3. The collected organic layer was washed with 1 M HCl and brine, filtered through $Na_2SO_4$, and concentrated in vacuo. Purification of the residue on silica gel with 0-100% acetone/cyclohexane provided compound (39-1) (417 mg, 0.847 mmol, 76% yield). [M−1]⁻, 491.02.

Step 2

To a suspension of (39-1) (28 mg, 0.057 mmol) in DCM (0.6 mL) at 0° C. was added $Et_3N$ (79 µl, 0.568 mmol) and TFAA (40.1 µl, 0.284 mmol). The mixture was warmed to rt and stirred for 1 h. The reaction was quenched with cold $NaHCO_3$ solution and extracted with EtOAc. The organic layer was washed with water, 1N HCl, sat $NaHCO_3$ and brine, dried over $Na_2SO_4$, filtered, and concentrated. Purification of the residue on silica gel column provided Example 39 (24 mg, 0.051 mmol, 89% yield). [M−H]⁻ 473.17. ¹H NMR (400 MHz, Methanol-$d_4$) δ 7.35-7.15 (m, 5H), 7.07-6.88 (m, 4H), 5.21-4.88 (m, 2H), 4.77 (dd, J=12.1, 3.8 Hz, 1H), 4.19-4.07 (m, 1H), 3.92 (d, J=10.7 Hz, 1H), 3.71 (p, J=10.8 Hz, 1H), 2.93 (d, J=4.8 Hz, 3H), 2.75-2.57 (m, 2H), 1.79 (ddt, J=14.4, 9.2, 5.0 Hz, 1H), 1.67 (dq, J=14.8, 7.2, 6.6 Hz, 1H), 1.56-1.47 (m, 1H), 1.05-0.88 (m, 6H).

The following examples were prepared employing similar protocol as described above.

| Example | Structure | MS |
|---|---|---|
| 40 | 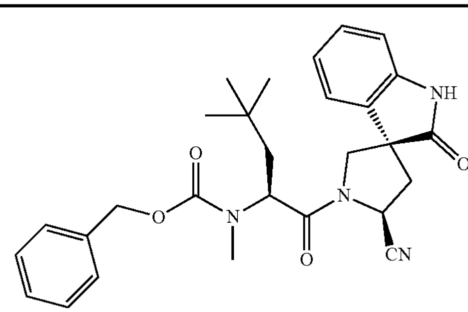 | [M + Na]⁺ 511.21 |

| Example | Structure | MS |
|---|---|---|
| 41 | 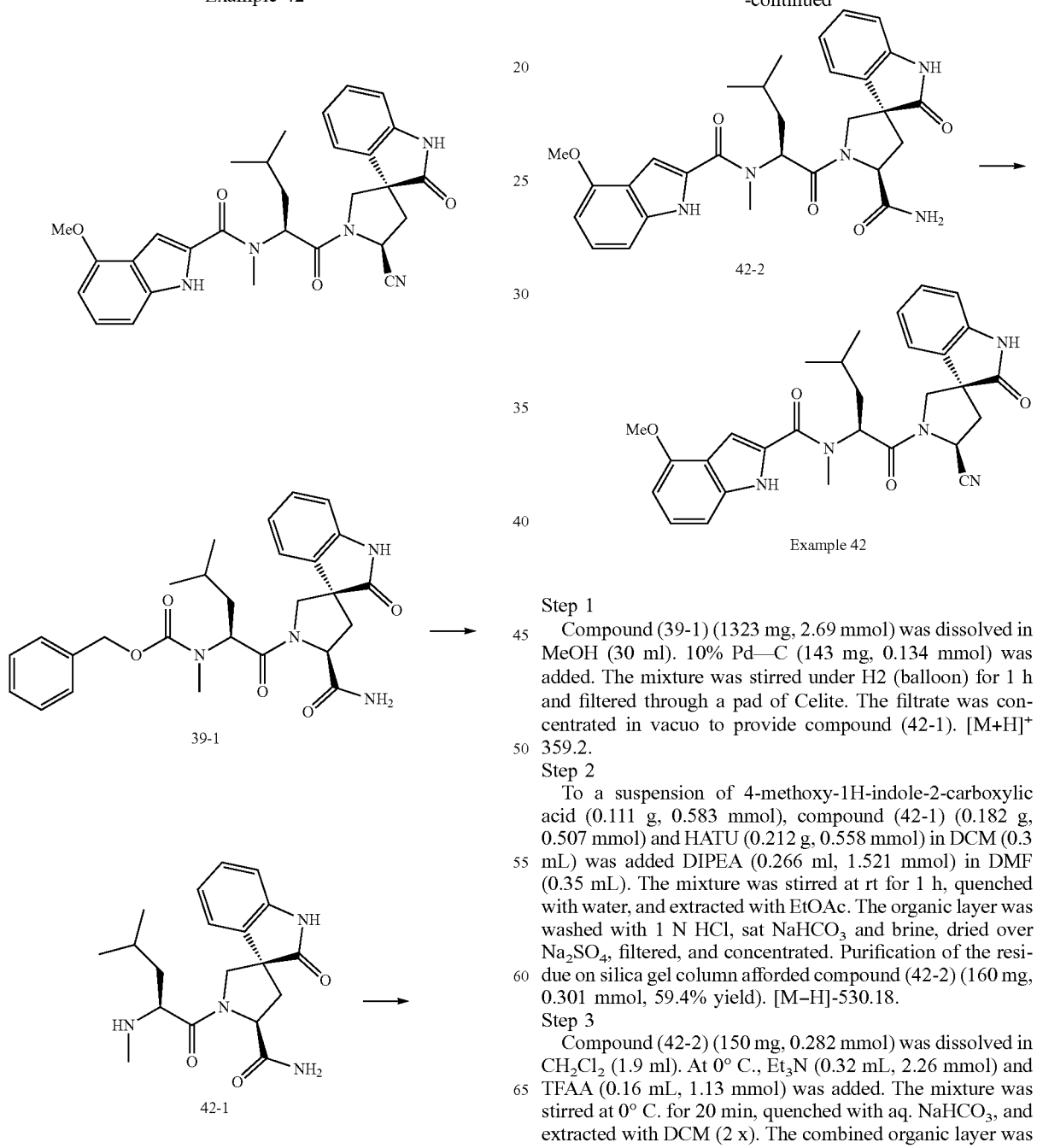 | [M – H]⁻ 507.20 |

Example 42

Step 1

Compound (39-1) (1323 mg, 2.69 mmol) was dissolved in MeOH (30 ml). 10% Pd—C (143 mg, 0.134 mmol) was added. The mixture was stirred under H2 (balloon) for 1 h and filtered through a pad of Celite. The filtrate was concentrated in vacuo to provide compound (42-1). [M+H]⁺ 359.2.

Step 2

To a suspension of 4-methoxy-1H-indole-2-carboxylic acid (0.111 g, 0.583 mmol), compound (42-1) (0.182 g, 0.507 mmol) and HATU (0.212 g, 0.558 mmol) in DCM (0.3 mL) was added DIPEA (0.266 ml, 1.521 mmol) in DMF (0.35 mL). The mixture was stirred at rt for 1 h, quenched with water, and extracted with EtOAc. The organic layer was washed with 1 N HCl, sat NaHCO₃ and brine, dried over Na₂SO₄, filtered, and concentrated. Purification of the residue on silica gel column afforded compound (42-2) (160 mg, 0.301 mmol, 59.4% yield). [M–H]-530.18.

Step 3

Compound (42-2) (150 mg, 0.282 mmol) was dissolved in CH₂Cl₂ (1.9 ml). At 0° C., Et₃N (0.32 mL, 2.26 mmol) and TFAA (0.16 mL, 1.13 mmol) was added. The mixture was stirred at 0° C. for 20 min, quenched with aq. NaHCO₃, and extracted with DCM (2 x). The combined organic layer was dried over Na$_2$SO$_4$ and concentrated in vacuo. Purification of the residue on silica gel with 0-40% acetone/cyclohexane provided Example 42 (114 mg, 0.222 mmol, 79% yield). [M−H]$^-$ 512.18; $^1$H NMR (400 MHz, Methanol-d$_4$) δ 7.15 (t, J=8.0 Hz, 1H), 7.05 (t, J=7.8 Hz, 1H), 7.01-6.94 (m, 2H), 6.90 (s, 1H), 6.85 (dd, J=15.4, 7.7 Hz, 2H), 6.52 (d, J=7.7 Hz, 1H), 5.53 (brs, 1H), 5.19 (t, J=8.0 Hz, 1H), 4.21 (d, J=11.0 Hz, 1H), 3.99 (d, J=11.0 Hz, 1H), 3.96 (s, 3H), 3.40 (s, 3H), 2.75-2.60 (m, 2H), 1.96-1.76 (m, 2H), 1.63 (ddt, J=14.6, 13.0, 6.6 Hz, 1H), 1.47 (s, 1H), 1.26 (t, J=7.1 Hz, 1H), 1.01 (m, 6H).

The following examples were prepared employing similar protocol as described above.

| Example | Structure | MS | NMR |
|---|---|---|---|
| 43 | 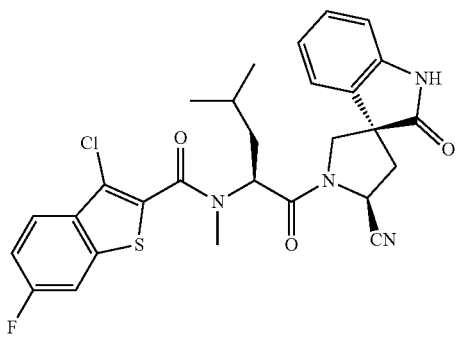 [SMILES: CC(C)C[C@@H](C(=O)N1C[C@]2(C[C@H]1C#N)C(=O)Nc1ccccc12)N(C)C(=O)c1sc2cc(F)ccc2c1Cl] | [M + Na]$^+$ 575.11 | $^1$H NMR (400 MHz, Acetone-d$_6$) δ 9.58 (s, 1H), 7.77-7.68 (m, 2H), 7.27 (td, J = 8.9, 2.3 Hz, 1H), 7.17 (t, J = 7.6 Hz, 1H), 7.03 (d, J = 7.3 Hz, 1H), 6.91 (t, J = 7.2 Hz, 2H), 5.36 (dd, J = 9.7, 5.2 Hz, 1H), 5.08 (t, J = 8.2 Hz, 1H), 4.10 (d, J = 10.5 Hz, 1H), 3.96 (d, J = 10.5 Hz, 1H), 3.00 (s, 3H), 2.71-2.56 (m, 2H), 1.82 (m, 1H), 1.74-1.61 (m, 2H), 0.89 (m, 6H). |
| 44 | 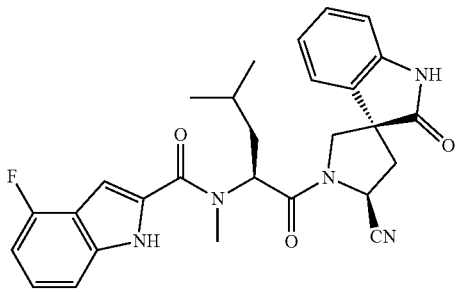 [SMILES: CC(C)C[C@@H](C(=O)N1C[C@]2(C[C@H]1C#N)C(=O)Nc1ccccc12)N(C)C(=O)c1cc2c(F)cccc2[nH]1] | [M + Na]$^+$ 524.19 | $^1$H NMR (400 MHz, Acetone-d$_6$) δ 10.70 (s, 1H), 9.67 (s, 1H), 7.33 (d, J = 8.2 Hz, 1H), 7.22 (td, J = 8.0, 5.2 Hz, 1H), 7.03 (d, J = 7.7 Hz, 2H), 6.96-6.88 (m, 2H), 6.87-6.76 (m, 2H), 5.59 (dd, J = 9.5, 5.6 Hz, 1H), 5.21 (t, J = 8.2 Hz, 1H), 4.28 (d, J = 10.7 Hz, 1H), 4.00 (d, J = 10.6 Hz, 1H), 3.46 (s, 3H), 2.83-2.64 (m, 2H), 1.94 (ddd, J = 14.5, 9.6, 5.2 Hz, 1H), 1.79 (ddd, J = 14.2, 8.7, 5.6 Hz, 1H), 1.64 (dtd, J = 8.7, 6.7, 5.1 Hz, 1H), 0.99 (m, 6H). |
| 45 | 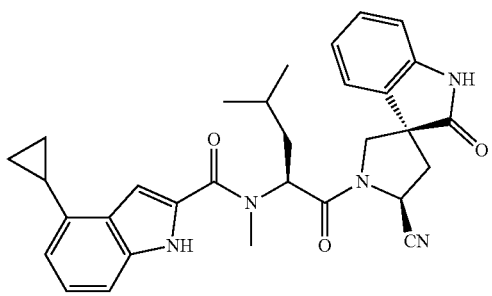 [SMILES: CC(C)C[C@@H](C(=O)N1C[C@]2(C[C@H]1C#N)C(=O)Nc1ccccc12)N(C)C(=O)c1cc2c(C3CC3)cccc2[nH]1] | [M + Na]$^+$ 546.23 | $^1$H NMR (400 MHz, Acetone-d$_6$) δ 10.39 (s, 1H), 9.67 (s, 1H), 7.29 (d, J = 8.3 Hz, 1H), 7.17-7.03 (m, 4H), 6.95-6.84 (m, 2H), 6.65 (d, J = 7.2 Hz, 1H), 5.61 (m, 1H), 5.20 (t, J = 8.2 Hz, 1H), 4.27 (d, J = 10.7 Hz, 1H), 4.01 (d, J = 10.6 Hz, 1H), 3.47 (s, 3H), 2.83-2.63 (m, 2H), 2.32 (br s, 1H), 1.92 (ddd, J = 14.3, 9.3, 5.2 Hz, 1H), 1.86-1.74 (m, 1H), 1.64 (dt, J = 13.7, 6.8 Hz, 1H), 1.01 (m, 8H), 0.84-0.78 (m, 2H). |
| 46 | 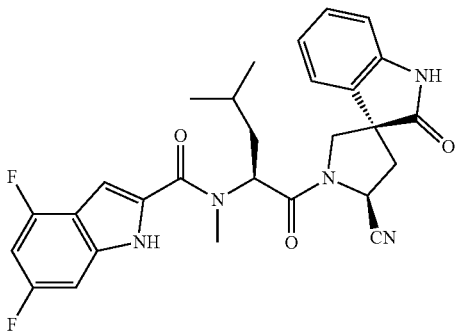 [SMILES: CC(C)C[C@@H](C(=O)N1C[C@]2(C[C@H]1C#N)C(=O)Nc1ccccc12)N(C)C(=O)c1cc2c(F)cc(F)cc2[nH]1] | [M + Na]$^+$ 542.17 | $^1$H NMR (400 MHz, Acetone-d$_6$) δ 10.79 (s, 1H), 9.67 (s, 1H), 7.04 (m, 3H), 6.96 (s, 1H), 6.91 (d, J = 7.7 Hz, 1H), 6.85-6.70 (m, 2H), 5.59 (dd, J = 9.5, 5.6 Hz, 1H), 5.21 (t, J = 8.3 Hz, 1H), 4.30 (d, J = 10.8 Hz, 1H), 3.98 (d, J = 10.6 Hz, 1H), 3.45 (s, 3H), 2.78-2.66 (m, 2H), 1.95 (td, J = 9.4, 4.7 Hz, 1H), 1.78 (ddd, J = 14.2, 8.7, 5.5 Hz, 1H), 1.63 (dt, J = 13.8, 6.4 Hz, 1H), 0.98 (m, 6H). |

-continued

| Example | Structure | MS | NMR |
|---|---|---|---|
| 47 | 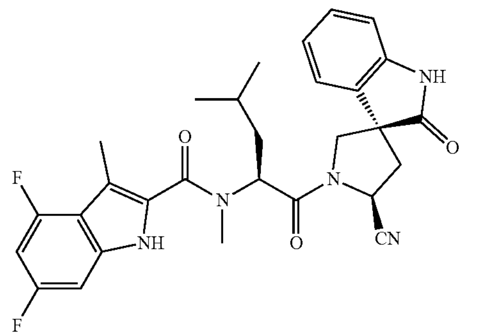 [SMILES: Cc1c(C(=O)N(C)[C@@H](CC(C)C)C(=O)N2C[C@]3(C[C@H]2C#N)C(=O)Nc2ccccc23)[nH]c2cc(F)cc(F)c12] | [M + Na]+ 556.18 | 1H NMR (500 MHz, Acetone-d6) δ 10.47 (s, 1H), 9.71 (s, 1H), 7.28 (td, J = 7.7, 1.2 Hz, 1H), 7.16 (d, J = 7.4 Hz, 1H), 7.02 (t, J = 7.3 Hz, 2H), 6.96 (s, 1H), 6.66 (ddd, J = 11.3, 10.1, 2.1 Hz, 1H), 5.37 (s, 1H), 5.19 (t, J = 8.3 Hz, 1H), 4.32 (br s, 1H), 4.07 (br s, 1H), 3.20 (s, 3H), 2.82-2.66 (m, 2H), 2.27 (s, 3H), 2.00-1.91 (m, 1H), 1.81 (s, 1H), 1.72 (s, 1H), 1.05 (d, J = 6.5 Hz, 3H), 0.99 (br s, 3H). |
| 48 | 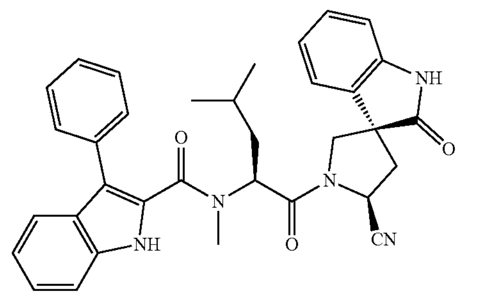 [SMILES: CC(C)C[C@@H](C(=O)N1C[C@]2(C[C@H]1C#N)C(=O)Nc1ccccc12)N(C)C(=O)c1[nH]c2ccccc2c1-c1ccccc1] | [M + Na]+ 582.22 | 1H NMR (500 MHz, Acetone-d6) δ 10.37 (s, 1H), 9.72 (s, 1H), 7.73 (d, J = 8.0 Hz, 1H), 7.55-7.46 (m, 5H), 7.39 (tt, J = 5.8, 2.9 Hz, 1H), 7.31-7.23 (m, 2H), 7.15 (t, J = 7.6 Hz, 1H), 7.11 (d, J = 7.5 Hz, 1H), 7.04 (d, J = 7.8 Hz, 1H), 6.94 (t, J = 7.5 Hz, 1H), 5.31 (dd, J = 10.7, 4.9 Hz, 1H), 5.15 (t, J = 8.3 Hz, 1H), 4.34 (d, J = 10.5 Hz, 1H), 4.05 (d, J = 10.5 Hz, 1H), 2.77 (s, 3H), 2.70 (m, 2H), 1.82-1.72 (m, 1H), 1.62 (ddd, J = 14.4, 9.6, 4.9 Hz, 1H), 1.41 (m, 1H), 0.99 (d, J = 6.5 Hz, 3H), 0.93 (d, J = 6.7 Hz, 3H). |
| 49 | 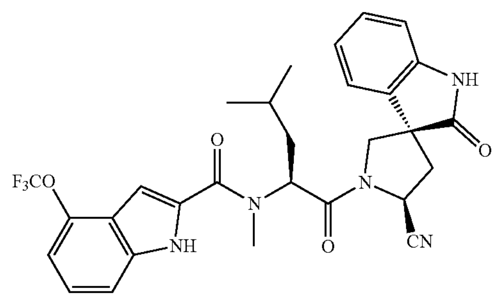 [SMILES: CC(C)C[C@@H](C(=O)N1C[C@]2(C[C@H]1C#N)C(=O)Nc1ccccc12)N(C)C(=O)c1cc2c(OC(F)(F)F)cccc2[nH]1] | [M + Na]+ 590.20 | 1H NMR (400 MHz, Acetone-d6) δ 10.81 (s, 1H), 9.66 (s, 1H), 7.53 (d, J = 8.3 Hz, 1H), 7.31 (t, J = 8.0 Hz, 1H), 7.10-6.96 (m, 4H), 6.91 (d, J = 7.4 Hz, 1H), 6.81 (t, J = 7.5 Hz, 1H), 5.60 (dd, J = 9.4, 5.8 Hz, 1H), 5.21 (t, J = 8.2 Hz, 1H), 4.28 (d, J = 10.6 Hz, 1H), 4.00 (d, J = 10.6 Hz, 1H), 3.46 (s, 3H), 2.82-2.60 (m, 2H), 2.00-1.90 (m, 1H), 1.85-1.74 (m, 1H), 1.64 (dt, J = 13.8, 6.6 Hz, 1H), 0.99 (m, 6H). |
| 50 | 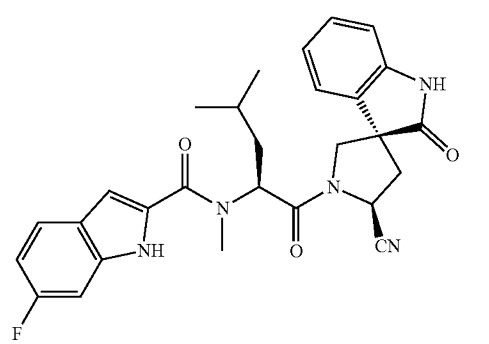 [SMILES: CC(C)C[C@@H](C(=O)N1C[C@]2(C[C@H]1C#N)C(=O)Nc1ccccc12)N(C)C(=O)c1cc2ccc(F)cc2[nH]1] | [M + Na]+ 524.22 | 1H NMR (400 MHz, Acetone-d6) δ 10.51 (s, 1H), 9.67 (s, 1H), 7.66 (s, 1H), 7.24-7.16 (m, 1H), 7.08-6.98 (m, 2H), 6.92 (d, J = 8.3 Hz, 3H), 6.82 (s, 1H), 5.59 (dd, J = 9.5, 5.7 Hz, 1H), 5.21 (t, J = 8.3 Hz, 1H), 4.29 (d, J = 10.8 Hz, 1H), 3.99 (d, J = 10.6 Hz, 1H), 3.43 (s, 3H), 2.78-2.63 (m, 2H), 2.00-1.91 (m, 1H), 1.77 (m, 1H), 1.61 (m, 1H), 0.98 (m, 6H). |
| 51 | 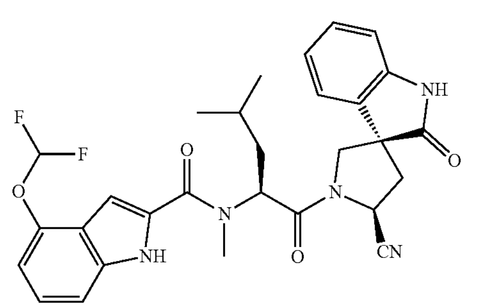 [SMILES: CC(C)C[C@@H](C(=O)N1C[C@]2(C[C@H]1C#N)C(=O)Nc1ccccc12)N(C)C(=O)c1cc2c(OC(F)F)cccc2[nH]1] | [M + Na]+ 572.22 | 1H NMR (400 MHz, Acetone-d6) δ 10.69 (s, 1H), 9.66 (s, 1H), 7.39 (d, J = 8.3 Hz, 1H), 7.25 (t, J = 8.0 Hz, 1H), 7.15 (s, 1H), 7.03 (d, J = 7.6 Hz, 2H), 6.97-6.79 (m, 4H), 5.59 (dd, J = 9.4, 5.6 Hz, 1H), 5.21 (t, J = 8.2 Hz, 1H), 4.28 (d, J = 10.8 Hz, 1H), 4.00 (d, J = 10.6 Hz, 1H), 3.46 (s, 3H), 2.78-2.66 (m, 2H), 2.00-1.90 (m, 1H), 1.79 (ddd, J = 14.2, 8.8, 5.7 Hz, 1H), 1.64 (dt, J = 14.0, 6.8 Hz, 1H), 0.99 (m, 6H). |

-continued

| Example | Structure | MS | NMR |
|---|---|---|---|
| 52 | 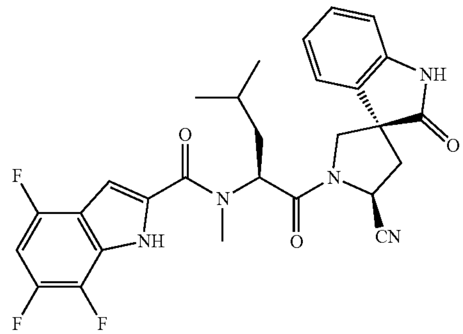 [SMILES: CC(C)C[C@@H](C(=O)N1C[C@]2(C[C@H]1C#N)C(=O)Nc1ccccc12)N(C)C(=O)c1cc2c(F)cc(F)c(F)c2[nH]1] | [M + Na]+ 560.20 | 1H NMR (400 MHz, Acetone-d6) δ 9.67 (s, 1H), 7.04 (dd, J = 14.4, 7.4 Hz, 2H), 6.93 (ddd, J = 10.6, 8.9, 5.1 Hz, 3H), 6.84 (t, J = 7.5 Hz, 1H), 5.61-5.53 (m, 1H), 5.22 (t, J = 8.3 Hz, 1H), 4.25 (d, J = 10.6 Hz, 1H), 3.99 (d, J = 10.7 Hz, 1H), 3.43 (s, 3H), 2.82-2.73 (m, 5H), 2.76-2.64 (m, 1H), 1.80 (ddd, J = 14.2, 8.7, 5.6 Hz, 1H), 1.64 (dt, J = 13.7, 6.6 Hz, 1H), 1.44 (s, 3H), 0.99 (dd, J = 18.3, 6.6 Hz, 5H). |
| 53 | 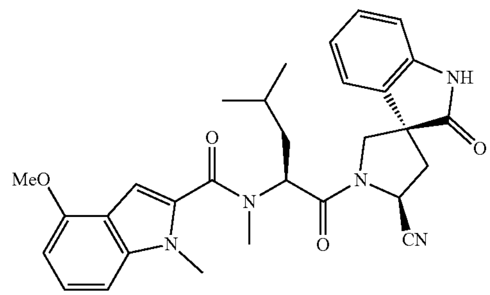 [SMILES: COc1cccc2c1cc(C(=O)N(C)[C@@H](CC(C)C)C(=O)N1C[C@]3(C[C@H]1C#N)C(=O)Nc1ccccc13)n2C] | [M + Na]+ 550.25 | 1H NMR (400 MHz, Acetone-d6) δ 9.72 (s, 1H), 7.26 (td, J = 7.7, 1.3 Hz, 1H), 7.19 (t, J = 8.1 Hz, 1H), 7.13 (s, 1H), 7.05-6.95 (m, 3H), 6.63-6.55 (m, 2H), 5.56 (br s, 1H), 5.24 (t, J = 8.3 Hz, 1H), 4.40 (d, J = 10.9 Hz, 1H), 4.05 (d, J = 10.6 Hz, 1H), 3.95 (s, 3H), 3.47 (s, 3H), 2.83 (d, J = 0.5 Hz, 4H), 2.78-2.66 (m, 2H), 1.98 (ddd, J = 14.1, 9.6, 4.8 Hz, 1H), 1.79 (ddd, J = 13.8, 8.7, 5.6 Hz, 1H), 1.71 (br s, 1H), 1.05 (d, J = 6.5 Hz, 3H), 1.00 (d, J = 6.2 Hz, 3H). |
| 54 | 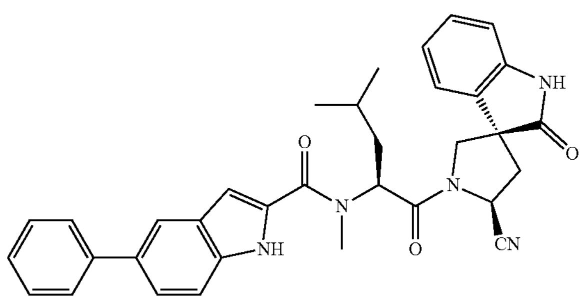 [SMILES: CC(C)C[C@@H](C(=O)N1C[C@]2(C[C@H]1C#N)C(=O)Nc1ccccc12)N(C)C(=O)c1cc2cc(-c3ccccc3)ccc2[nH]1] | [M + Na]+ 582.26 | 1H NMR (400 MHz, Acetone-d6) δ 10.50 (s, 1H), 9.67 (s, 1H), 7.91 (s, 1H), 7.69 (d, J = 7.7 Hz, 2H), 7.58 (s, 2H), 7.47 (t, J = 7.7 Hz, 2H), 7.38-7.29 (m, 1H), 7.07 (s, 2H), 6.94 (d, J = 9.1 Hz, 2H), 6.88 (s, 1H), 5.59 (br s, 1H), 5.22 (t, J = 7.9 Hz, 1H), 4.29 (br s, 1H), 4.01 (d, J = 10.5 Hz, 1H), 2.77-2.66 (m, 2H), 1.94 (br s, 1H), 1.85-1.73 (m, 1H), 1.63 (br s, 1H), 1.02 (d, J = 6.6 Hz, 3H), 0.97 (br s, 3H). |
| 55 | 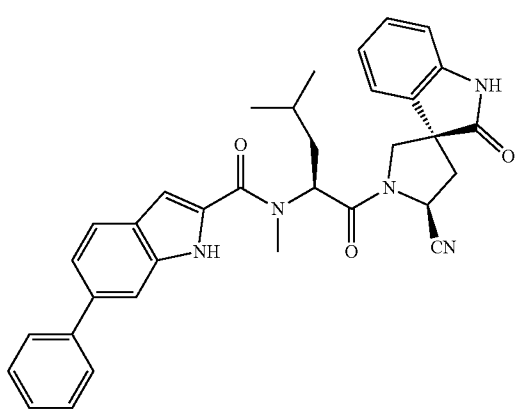 [SMILES: CC(C)C[C@@H](C(=O)N1C[C@]2(C[C@H]1C#N)C(=O)Nc1ccccc12)N(C)C(=O)c1cc2ccc(-c3ccccc3)cc2[nH]1] | [M + Na]+ 582.26 | 1H NMR (500 MHz, Acetone-d6) δ 10.48 (s, 1H), 9.67 (s, 1H), 7.76 (s, 1H), 7.73-7.67 (m, 2H), 7.48 (dd, J = 8.4, 7.1 Hz, 2H), 7.41 (d, J = 8.4 Hz, 1H), 7.39-7.33 (m, 1H), 7.09 (s, 2H), 7.05 (s, 1H), 6.94 (d, J = 7.8 Hz, 2H), 6.87 (s, 1H), 5.61 (d, J = 9.5 Hz, 1H), 5.22 (t, J = 8.2 Hz, 1H), 4.29 (d, J = 10.1 Hz, 1H), 4.01 (d, J = 10.6 Hz, 1H), 3.46 (s, 3H), 2.78-2.65 (m, 2H), 1.94 (m, 1H), 1.79 (m, 1H), 1.64 (dt, J = 13.8, 6.7 Hz, 1H), 1.02 (d, J = 6.7 Hz, 3H), 0.97 (d, J = 6.3 Hz, 3H). |

| Example | Structure | MS | NMR |
|---|---|---|---|
| 56 | 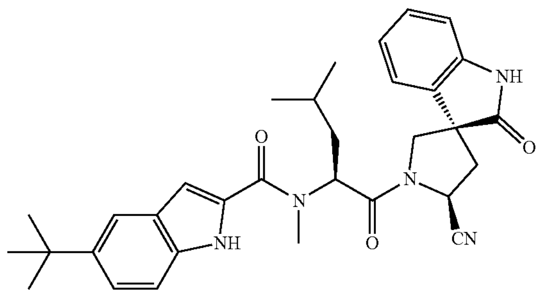 [SMILES: CC(C)C[C@@H](C(=O)N1C[C@]2(C[C@H]1C#N)C(=O)Nc1ccccc12)N(C)C(=O)c1cc2cc(C(C)(C)C)ccc2[nH]1] | [M − H]⁻ 538.1 | ¹H NMR (400 MHz, Acetone-d₆) δ 10.28 (s, 1H), 9.67 (s, 1H), 7.62 (s, 1H), 7.45-7.34 (m, 2H), 7.12 (s, 1H), 7.06 (s, 1H), 6.94 (d, J = 7.8 Hz, 1H), 6.87 (d, J = 15.3 Hz, 2H), 5.57 (dd, J = 9.6, 5.5 Hz, 1H), 5.21 (t, J = 8.1 Hz, 1H), 4.27 (br s, 1H), 4.01 (d, J = 10.5 Hz, 1H), 3.43 (s, 3H), 2.68 (m, 2H), 1.93 (m, 1H), 1.83-1.72 (m, 1H), 1.61 (dd, J = 13.8, 6.7 Hz, 1H), 1.38 (s, 9H), 1.01 (d, J = 6.6 Hz, 3H), 0.95 (br s, 3H). |
| 57 | 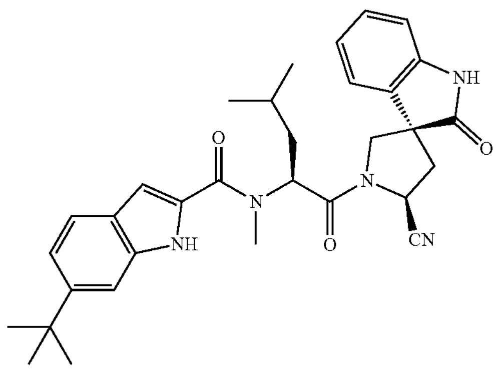 [SMILES: CC(C)C[C@@H](C(=O)N1C[C@]2(C[C@H]1C#N)C(=O)Nc1ccccc12)N(C)C(=O)c1cc2ccc(C(C)(C)C)cc2[nH]1] | [M − H]⁻ 538.1 | ¹H NMR (400 MHz, Acetone-d₆) δ 10.25 (s, 1H), 9.66 (s, 1H), 7.55 (s, 1H), 7.50 (d, J = 1.5 Hz, 1H), 7.21 (d, J = 8.5 Hz, 1H), 7.11 (s, 1H), 7.06 (s, 1H), 6.94 (d, J = 7.8 Hz, 1H), 6.89 (s, 1H), 6.82 (s, 1H), 5.58 (dd, J = 9.5, 5.6 Hz, 1H), 5.21 (t, J = 8.2 Hz, 1H), 4.24 (br s, 1H), 4.01 (d, J = 10.6 Hz, 1H), 3.42 (s, 3H), 2.83 (d, J = 0.8 Hz, 3H), 2.78-2.63 (m, 2H), 1.91 (m, 1H), 1.78 (ddd, J = 14.1, 8.7, 5.6 Hz, 1H), 1.62 (dt, J = 13.8, 6.7 Hz, 1H), 1.37 (s, 9H), 0.98 (d, J = 6.4 Hz, 3H), 0.95 (br s, 3H). |
| 58 | 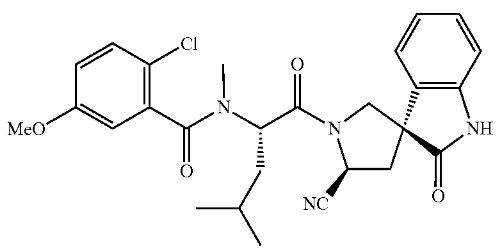 [SMILES: COc1ccc(Cl)c(C(=O)N(C)[C@@H](CC(C)C)C(=O)N2C[C@]3(C[C@H]2C#N)C(=O)Nc2ccccc23)c1] | [M + Na]⁺ 531.15, 533.10 | ¹H NMR (500 MHz, Methanol-d₄) δ 7.38-7.29 (m, 2H), 7.07-6.94 (m, 5H), 5.52 (t, J = 7.5 Hz, 1H), 5.21 (q, J = 8.0 Hz, 1H), 4.17 (d, J = 11.8 Hz, 1H), 4.07 (dd, J = 19.0, 10.5 Hz, 1H), 3.82-3.73 (m, 3H), 3.23 (s 3 H), 2.72 (qd, J = 13.2, 8.4 Hz, 2H), 1.85 (m, 3H), 1.05 (m, 6H). |
| 59 | 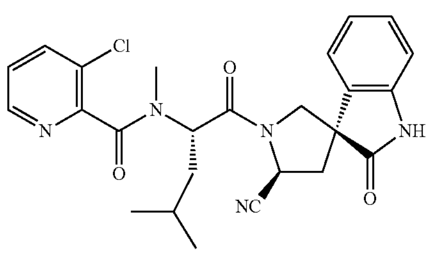 [SMILES: CC(C)C[C@@H](C(=O)N1C[C@]2(C[C@H]1C#N)C(=O)Nc1ccccc12)N(C)C(=O)c1ncccc1Cl] | [M + Na]⁺ 480.27, 450.10 | ¹H NMR (500 MHz, Acetone-d₆) δ 9.70 (s, 1H), 8.49 (dd, J = 4.7, 1.4 Hz, 1H), 7.91 (dd, J = 8.2, 1.4 Hz, 1H), 7.47 (dd, J = 8.3, 4.7 Hz, 1H), 7.39-7.13 (m, 2H), 7.06-6.97 (m, 2H), 5.60 (dd, J = 9.7, 5.1 Hz, 1H), 5.23-5.16 (m, 1H), 4.26 (dd, J = 10.5, 1.0 Hz, 1H), 4.11 (d, J = 10.6 Hz, 1H), 2.82 (s, 3 H), 2.82-2.76 (m, 1H), 2.70 (dd, J = 13.2, 7.6 Hz, 1H), 2.00-1.87 (m, 1H), 1.83-1.70 (m, 3H), 1.03 (t, J = 6.5 Hz, 6H). |
| 60 | 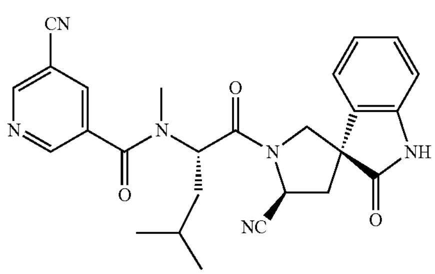 [SMILES: CC(C)C[C@@H](C(=O)N1C[C@]2(C[C@H]1C#N)C(=O)Nc1ccccc12)N(C)C(=O)c1cncc(C#N)c1] | [M + H]⁺ 471.24 | ¹H NMR (400 MHz, Acetone-d₆) δ 9.79 (s, 1H), 8.99 (d, J = 2.0 Hz, 1H), 8.50 (d, J = 2.1 Hz, 1H), 7.71 (t, J = 2.1 Hz, 1H), 7.33 (td, J = 7.7, 1.4 Hz, 1H), 7.13-7.05 (m, 2H), 7.01 (td, J = 7.5, 1.1 Hz, 1H), 5.54 (dd, J = 9.0, 6.0 Hz, 1H), 5.24 (t, J = 8.5 Hz, 1H), 4.38 (dd, J = 10.7, 1.3 Hz, 1H), 4.12-3.96 (m, 1H), 3.04 (s, 3H), 2.82-2.67 (m, 2H), 1.92 (ddd, J = 14.0, 8.9, 5.4 Hz, 1H), 1.82 (ddd, J = 14.0, 8.5, 6.1 Hz, 1H), 1.78-1.65 (m, 1H), 1.01 (dd, J = 14.7, 6.5 Hz, 6H). |

| Example | Structure | MS | NMR |
|---|---|---|---|
| 61 | 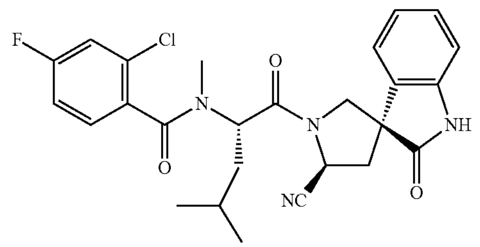 [SMILES: CC(C)C[C@@H](C(=O)N1C[C@]2(C[C@H]1C#N)C(=O)Nc1ccccc12)N(C)C(=O)c1ccc(F)cc1Cl] | [M + Na]+ 519.04, 521.08 | 1H NMR (400 MHz, Acetone-d6) δ 9.79 (s, 1H), 7.49-7.23 (m, 3H), 7.20-6.90 (m, 4H), 5.59 (dd, J = 8.6, 6.3 Hz, 1H), 5.23 (br, 1H), 4.21 (d, J = 10.8 Hz, 1H), 4.08 (br, 1H), 2.85 (s, 3 H)2.74 (td, J = 14.0, 13.0, 8.5 Hz, 2H), 1.97-1.61 (m, 3H), 1.01 (t, J = 6.3 Hz, 6H). |
| 62 | 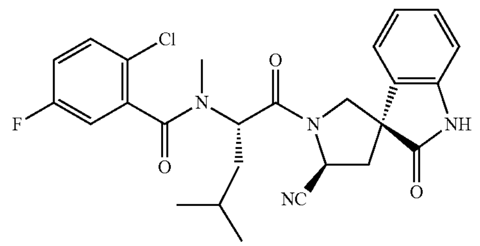 [SMILES: CC(C)C[C@@H](C(=O)N1C[C@]2(C[C@H]1C#N)C(=O)Nc1ccccc12)N(C)C(=O)c1cc(F)ccc1Cl] | [M + Na]+ 519.19 521.11 | 1H NMR (400 MHz, Acetone-$d_6$) δ 9.80 (s, 1H), 7.50 (s, 1H), 7.31 (d, J = 21.4 Hz, 1H), 7.22 (td, J = 8.6, 3.1 Hz, 1H), 7.07 (d, J = 26.1 Hz, 4H), 5.58 (t, J = 7.4 Hz, 1H), 5.22 (d, J = 9.0 Hz, 1H), 4.23 (d, J = 10.6 Hz, 1H), 4.16-3.97 (m, 1H), 2.82 (s, 3 H), 2.80-2.67 (m, 2H), 1.94-1.64 (m, 3H), 1.01 (t, J = 6.4 Hz, 6H). |
| 63 | 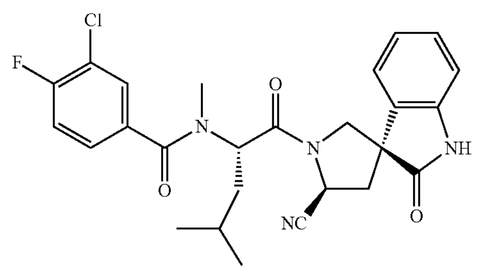 [SMILES: CC(C)C[C@@H](C(=O)N1C[C@]2(C[C@H]1C#N)C(=O)Nc1ccccc12)N(C)C(=O)c1ccc(F)c(Cl)c1] | [M + Na]+ 519.13, 521.02 | 1H NMR (400 MHz, Acetone-$d_6$) δ 9.78 (s, 1H), 7.35 (td, J = 7.6, 1.5 Hz, 1H), 7.28 (t, J = 8.9 Hz, 1H), 7.18-7.03 (m, 4H), 7.04-6.94 (m, 2H), 5.51 (dd, J = 8.9, 6.0 Hz, 1H), 5.23 (t, J = 8.5 Hz, 1H), 4.42-4.26 (m, 1H), 4.00 (d, J = 10.7 Hz, 1H), 2.97 (s, 3H), 2.82-2.60 (m, 2H), 1.89 (ddd, J = 14.2, 10.9, 5.5 Hz, 1H), 1.79 (ddd, J = 14.0, 8.4, 6.1 Hz, 1H), 1.69 (dq, J = 13.9, 6.6 Hz, 1H), 1.00 (dd, J = 14.5, 6.5 Hz, 6H). |
| 64 | 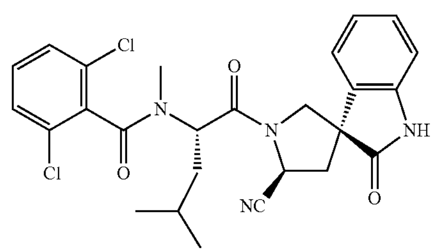 [SMILES: CC(C)C[C@@H](C(=O)N1C[C@]2(C[C@H]1C#N)C(=O)Nc1ccccc12)N(C)C(=O)c1c(Cl)cccc1Cl] | [M + Na]+ 535.11, 537.00 | 1H NMR (400 MHz, Acetone-$d_6$) δ 9.73 (s, 1H), 7.49 (ddt, J = 7.3, 3.9, 1.9 Hz, 1H), 7.46-7.42 (m, 2H), 7.28 (tt, J = 7.7, 1.1 Hz, 1H), 7.15 (d, J = 7.5 Hz, 1H), 7.01 (dt, J = 7.5, 3.7 Hz, 2H), 5.62-5.54 (m, 1H), 5.20 (t, J = 8.4 Hz, 1H), 4.27 (d, J = 10.3 Hz, 1H), 4.15 (d, J = 10.3 Hz, 1H), 2.90 (s, 3H), 2.79-2.61 (m, 2H), 1.98-1.68 (m, 3H), 1.03 (dd, J = 8.9, 6.5 Hz, 6H). |
| 65 | 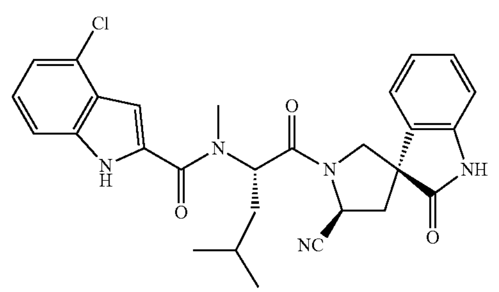 | [M + Na]+ 540.13, 542.10 | 1H NMR (400 MHz, Acetone-$d_6$) δ 10.77 (s, 1H), 9.67 (s, 1H), 7.47 (d, J = 8.2 Hz, 1H), 7.23 (t, J = 7.9 Hz, 1H), 7.14 (dd, J = 7.5, 0.8 Hz, 1H), 7.04 (d, J = 7.4 Hz, 2H), 6.95-6.89 (m, 2H), 6.84 (t, J = 7.5 Hz, 1H), 5.60 (dd, J = 9.5, 5.7 Hz, 1H), 5.22 (t, J = 8.2 Hz, 1H), 4.27 (d, J = 10.7 Hz, 1H), 4.01 (d, J = 10.6 Hz, 1H), 3.47 (s, 3H), 2.81-2.63 (m, 2H), 1.94 (td, J = 9.3, 4.7 Hz, 1H), 1.80 (ddd, J = 14.2, 8.7, 5.7 Hz, 1H), 1.65 (dpd, J = 8.6, 6.6, 5.2 Hz, 1H), 0.99 (m, 6H). |
| 66 | 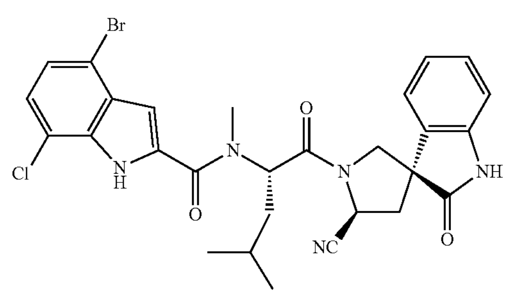 [SMILES: CC(C)C[C@@H](C(=O)N1C[C@]2(C[C@H]1C#N)C(=O)Nc1ccccc12)N(C)C(=O)c1cc2c(Br)ccc(Cl)c2[nH]1] | [M − H]− 594.05, 596.03 | 1H NMR (400 MHz, Acetone-$d_6$) δ 9.69 (s, 1H), 7.61 (d, J = 8.2 Hz, 1H), 7.49 (d, J = 8.2 Hz, 1H), 7.39 (s, 1H), 7.19-7.08 (m, 2H), 7.08-6.97 (m, 1H), 6.93 (t, J = 8.7 Hz, 1H), 5.44 (dd, J = 9.7, 5.4 Hz, 1H), 5.22 (td, J = 8.3, 3.9 Hz, 1H), 4.13-3.97 (m, 2H), 3.62 (s, 3H), 2.84-2.61 (m, 2H), 1.86 (ddd, J = 14.5, 9.0, 5.5 Hz, 1H), 1.79-1.58 (m, 2H), 1.10-0.90 (m, 6H). |

| Example | Structure | MS | NMR |
|---|---|---|---|
| 67 | 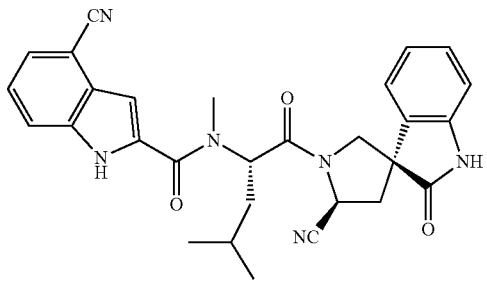 [SMILES: CC(C)C[C@@H](C(=O)N1C[C@]2(C[C@H]1C#N)C(=O)Nc1ccccc12)N(C)C(=O)c1cc2c(C#N)cccc2[nH]1] | [M + H]+ 509.22 | 1H NMR (400 MHz, Acetone-d6) δ 11.02 (s, 1H), 9.67 (s, 1H), 7.84 (d, J = 8.3 Hz, 1H), 7.59 (dd, J = 7.3, 0.9 Hz, 1H), 7.41 (dd, J = 8.4, 7.3 Hz, 1H), 7.13-6.94 (m, 3H), 6.96-6.77 (m, 2H), 5.60 (dd, J = 9.4, 5.7 Hz, 1H), 5.23 (t, J = 8.2 Hz, 1H), 4.26 (d, J = 10.7 Hz, 1H), 4.00 (d, J = 10.7 Hz, 1H), 3.49 (s, 3H), 2.81-2.66 (m, 2H), 2.00-1.88 (m, 1H), 1.81 (ddd, J = 14.2, 8.6, 5.7 Hz, 1H), 1.66 (dtd, J = 8.4, 6.6, 5.1 Hz, 1H), 1.00 (dd, J = 16.8, 6.6 Hz, 6H). |
| 68 | 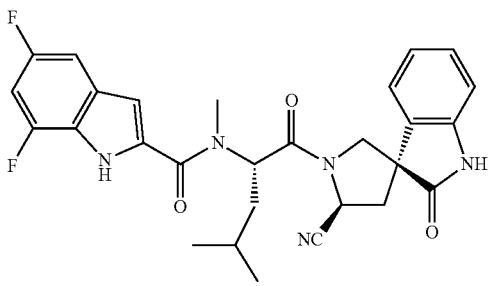 | [M + H]+ 509.22 | 1H NMR (400 MHz, Acetone-d6) δ 10.75 (s, 1H), 9.68 (s, 1H), 7.21 (d, J = 9.2 Hz, 1H), 7.13-6.99 (m, 2H), 6.96 (d, J = 9.7 Hz, 2H), 6.88 (s, 2H), 5.56 (br, 1H), 5.22 (t, J = 8.3 Hz, 1H), 4.24 (d, J = 10.7 Hz, 1H), 3.99 (d, J = 10.6 Hz, 1H), 3.40 (s, 3H), 2.77-2.60 (m, 2H), 1.98 (s, 1H), 1.87-1.70 (m, 1H), 1.63 (s, 1H), 0.99 (dd, J = 17.8, 6.5 Hz, 6H). |
| 69 | 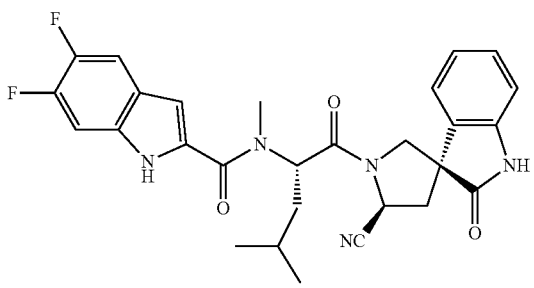 [SMILES: CC(C)C[C@@H](C(=O)N1C[C@]2(C[C@H]1C#N)C(=O)Nc1ccccc12)N(C)C(=O)c1cc2cc(F)c(F)cc2[nH]1] | [M + Na]+ 542.22 | 1H NMR (400 MHz, Acetone-d6) δ 10.61 (s, 1H), 9.67 (s, 1H), 7.54 (s, 1H), 7.38 (dd, J = 11.0, 6.9 Hz, 1H), 7.16-6.96 (m, 2H), 6.93 (br, 2H), 6.81 (br, 1H), 5.57 (d, J = 9.3 Hz, 1H), 5.21 (t, J = 8.3 Hz, 1H), 4.29 (d, J = 10.8 Hz, 1H), 3.99 (d, J = 10.6 Hz, 1H), 3.42 (s, 3H), 2.72 (qd, J = 13.2, 8.3 Hz, 2H), 1.99-1.89 (m, 1H), 1.77 (ddd, J = 14.2, 8.8, 5.5 Hz, 1H), 1.62 (dq, J = 14.1, 6.7 Hz, 1H), 0.98 (dd, J = 20.8, 6.5 Hz, 6H). |
| 70 | 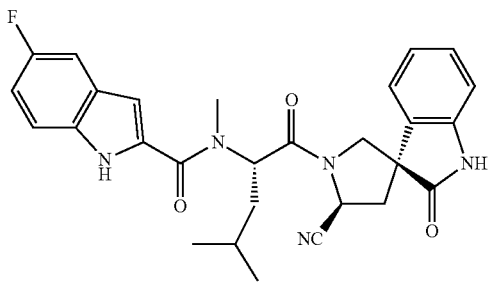 [SMILES: CC(C)C[C@@H](C(=O)N1C[C@]2(C[C@H]1C#N)C(=O)Nc1ccccc12)N(C)C(=O)c1cc2cc(F)ccc2[nH]1] | [M + Na]+ 524.20 | 1H NMR (400 MHz, Acetone-d6) δ 10.53 (s, 1H), 9.68 (s, 1H), 7.50 (dd, J = 9.0, 4.5 Hz, 1H), 7.33 (d, J = 9.6 Hz, 1H), 7.16-6.98 (m, 3H), 6.89 (dd, J = 26.7, 10.6 Hz, 3H), 5.64-5.46 (m, 1H), 5.21 (t, J = 8.2 Hz, 1H), 4.27 (d, J = 10.6 Hz, 1H), 4.00 (d, J = 10.6 Hz, 1H), 3.43 (s, 3H), 2.71 (tt, J = 13.3, 6.4 Hz, 2H), 1.97-1.88 (m, 1H), 1.78 (ddd, J = 14.2, 8.8, 5.6 Hz, 1H), 1.63 (dd, J = 13.7, 7.0 Hz, 1H), 0.98 (dd, J = 20.0, 6.5 Hz, 6H). |
| 71 | 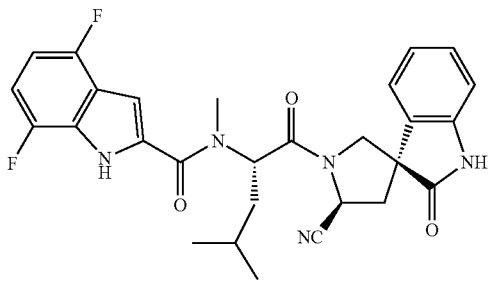 [SMILES: CC(C)C[C@@H](C(=O)N1C[C@]2(C[C@H]1C#N)C(=O)Nc1ccccc12)N(C)C(=O)c1cc2c(F)ccc(F)c2[nH]1] | [M + Na]+ 542.21 | 1H NMR (400 MHz, Acetone-d6) δ 10.96 (s, 1H), 9.67 (s, 1H), 7.04 (d, J = 7.6 Hz, 2H), 7.00-6.89 (m, 3H), 6.85 (t, J = 7.5 Hz, 1H), 6.77 (ddd, J = 9.8, 8.5, 3.0 Hz, 1H), 5.57 (dd, J = 9.5, 5.7 Hz, 1H), 5.22 (t, J = 8.3 Hz, 1H), 4.26 (d, J = 10.7 Hz, 1H), 4.00 (d, J = 10.7 Hz, 1H), 2.80-2.64 (m, 2H), 1.00 (dd, J = 18.1, 6.6 Hz, 6H). |

-continued

| Example | Structure | MS | NMR |
|---|---|---|---|
| 72 | 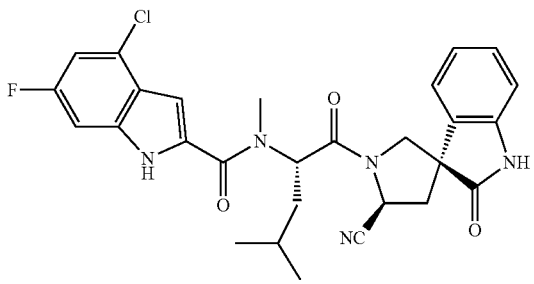 [SMILES: CC(C)C[C@@H](C(=O)N1C[C@]2(C[C@H]1C#N)C(=O)Nc1ccccc12)N(C)C(=O)c1cc2c(Cl)cc(F)cc2[nH]1] | [M + H]+ 536.11 | 1H NMR (400 MHz, Acetone-d6) δ 10.84 (s, 1H), 9.67 (s, 1H), 7.27-7.14 (m, 1H), 7.11-6.98 (m, 3H), 6.98-6.87 (m, 2H), 6.82 (t, J = 7.5 Hz, 1H), 5.59 (dd, J = 9.5, 5.6 Hz, 1H), 5.21 (t, J = 8.3 Hz, 1H), 4.29 (d, J = 10.7 Hz, 1H), 3.99 (d, J = 10.6 Hz, 1H), 3.47 (s, 3H), 2.79-2.62 (m, 2H), 1.99-1.87 (m, 1H), 1.79 (ddd, J = 14.2, 8.8, 5.7 Hz, 1H), 1.63 (dddd, J = 13.2, 11.7, 8.8, 6.5 Hz, 1H), 0.99 (dd, J = 19.1, 6.6 Hz, 6H). |
| 73 | 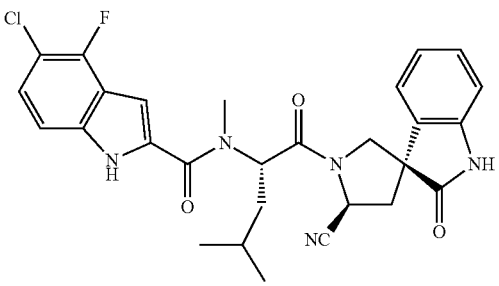 [SMILES: CC(C)C[C@@H](C(=O)N1C[C@]2(C[C@H]1C#N)C(=O)Nc1ccccc12)N(C)C(=O)c1cc2c(F)c(Cl)ccc2[nH]1] | [M − H]− 534.24, 535.68 | 1H NMR (400 MHz, Acetone-d6) δ 10.87 (s, 1H), 9.68 (s, 1H), 7.36 (d, J = 8.7 Hz, 1H), 7.28 (dd, J = 8.8, 6.9 Hz, 1H), 7.03 (dd, J = 11.8, 7.4 Hz, 2H), 6.97(s, 1H), 6.91 (d, J = 7.7 Hz, 1H), 6.82 (t, J = 7.5 Hz, 1H), 5.59 (dd, J = 9.4, 5.7 Hz, 1H), 5.22 (t, J = 8.3 Hz, 1H), 4.28 (d, J = 10.7 Hz, 1H), 3.99 (d, J = 10.6 Hz, 1H), 3.46 (s, 3H), 2.78-2.65 (m, 2H), 1.99-1.89 (m, 1H), 1.79 (ddd, J = 14.2, 8.7, 5.6 Hz, 1H), 1.72-1.44 (m, 1H), 0.99 (m, 6H). |
| 74 | 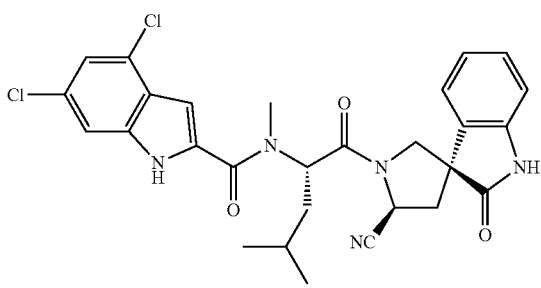 [SMILES: CC(C)C[C@@H](C(=O)N1C[C@]2(C[C@H]1C#N)C(=O)Nc1ccccc12)N(C)C(=O)c1cc2c(Cl)cc(Cl)cc2[nH]1] | [M − H]− 550.13, 552.14 | 1H NMR (400 MHz, Acetone-d6) δ 10.89 (s, 1H), 9.67 (s, 1H), 7.52 (s, 1H), 7.19 (d, J = 1.7 Hz, 1H), 7.08-6.97 (m, 2H), 6.97-6.88 (m, 2H), 6.82 (t, J = 7.5 Hz, 1H), 5.59 (dd, J = 9.5, 5.6 Hz, 1H), 5.22 (t, J = 8.3 Hz, 1H), 4.29 (d, J = 10.7 Hz, 1H), 3.99 (d, J = 10.6 Hz, 1H), 3.47 (s, 3H), 2.79- 2.63 (m, 2H), 2.02-1.87 (m, 1H), 1.79 (ddd, J = 14.2, 8.7, 5.6 Hz, 1H), 1.64 (dtd, J = 8.7, 6.7, 5.1 Hz, 1H), 0.99 (m, 6H). |
| 75 | 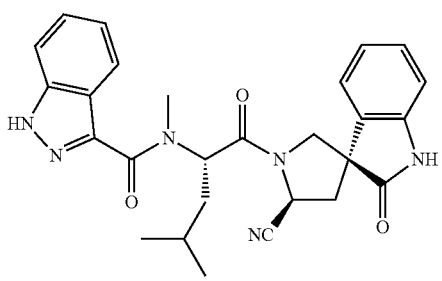 [SMILES: CC(C)C[C@@H](C(=O)N1C[C@]2(C[C@H]1C#N)C(=O)Nc1ccccc12)N(C)C(=O)c1n[nH]c2ccccc12] | [M − H]− 483.16 | |
| 76 | 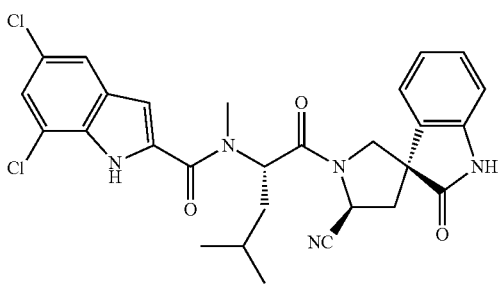 [SMILES: CC(C)C[C@@H](C(=O)N1C[C@]2(C[C@H]1C#N)C(=O)Nc1ccccc12)N(C)C(=O)c1cc2cc(Cl)cc(Cl)c2[nH]1] | [M − H]− 550.07, 551.95 | 1H NMR (400 MHz, Acetone-d6) δ 10.31 (s, 1H), 9.67 (s, 1H), 7.63 (s, 1H), 7.32 (s, 1H), 7.14-6.88 (m, 3H), 6.82 (d, J = 13.9 Hz, 2H), 5.53 (s, 1H), 5.20 (t, J = 8.4 Hz, 1H), 4.25 (d, J = 10.8 Hz, 1H), 3.95 (d, J = 10.6 Hz, 1H), 3.36 (s, 3H), 2.68 (td, J = 14.1, 13.3, 8.4 Hz, 2H), 1.85 (br, 1H), 1.79 (m, J1H), 1.61 (m, 1H), 0.96 (dd, J = 16.7, 6.6 Hz, 6H). |

-continued

| Example | Structure | MS | NMR |
|---|---|---|---|
| 77 | 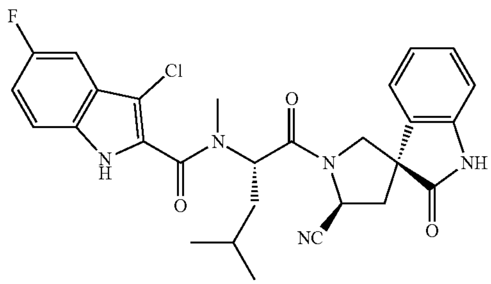 [SMILES: CC(C)C[C@@H](C(=O)N1C[C@]2(C[C@H]1C#N)C(=O)Nc1ccccc12)N(C)C(=O)c1[nH]c2ccc(F)cc2c1Cl] | [M + H]+ 536.15, 538.06 | 1H NMR (400 MHz, Acetone-d6) δ 10.80 (s, 1H), 9.72 (s, 1H), 7.51 (dd, J = 9.1, 4.3 Hz, 1H), 7.25 (t, J = 7.9 Hz, 2H), 7.18 (d, J = 7.4 Hz, 1H), 7.16-7.08 (m, 1H), 6.99 (dd, J = 17.6, 7.9 Hz, 2H), 5.47-5.30 (m, 1H), 5.21 (t, J = 8.1 Hz, 1H), 4.26 (d, J = 10.5 Hz, 1H), 4.09 (d, J = 10.5 Hz, 1H), 3.24 (s, 3H), 2.86-2.63 (m, 2H), 2.03-1.93 (m, 1H), 1.82 (d, J = 15.3 Hz, 2H), 1.02 (dd, J = 23.0, 6.0 Hz, 6484.20 H). |
| 78 | 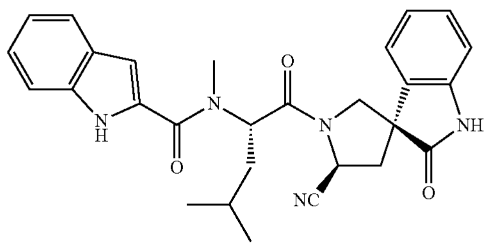 [SMILES: CC(C)C[C@@H](C(=O)N1C[C@]2(C[C@H]1C#N)C(=O)Nc1ccccc12)N(C)C(=O)c1cc2ccccc2[nH]1] | [M + H]+ 484.20 | 1H NMR (400 MHz, Acetone-d6) δ 10.43 (s, 1H), 9.67 (s, 1H), 7.64 (s, 1H), 7.49 (d, J = 8.3 Hz, 1H), 7.23 (ddd, J = 8.2, 6.9, 1.1 Hz, 1H), 7.06 (q, J = 9.4, 8.4 Hz, 3H), 6.89 (dd, J = 20.9, 11.6 Hz, 3H), 5.59 (dd, J = 9.5, 5.6 Hz, 1H), 5.21 (t, J = 8.2 Hz, 1H), 4.27 (d, J = 10.6 Hz, 1H), 4.01 (d, J = 10.6 Hz, 1H), 3.44 (s, 3H), 2.79-2.63 (m, 2H), 1.94 (ddd, J = 19.1, 9.7, 4.9 Hz, 1H), 1.78 (ddd, J = 14.2, 8.7, 5.6 Hz, 1H), 1.71-1.55 (m, 1H), 0.98 (dd, J = 20.7, 6.5 Hz, 6H). |
| 79 | 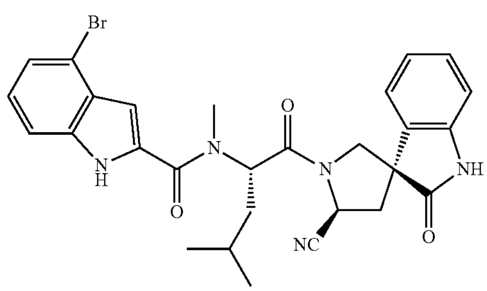 [SMILES: CC(C)C[C@@H](C(=O)N1C[C@]2(C[C@H]1C#N)C(=O)Nc1ccccc12)N(C)C(=O)c1cc2c(Br)cccc2[nH]1] | [M − H]− 560.00, 562.00 | 1H NMR (400 MHz, Acetone-d6) δ 10.79 (s, 1H), 9.67 (s, 1H), 7.52 (d, J = 8.2 Hz, 1H), 7.31 (d, J = 7.5 Hz, 1H), 7.17 (t, J = 7.9 Hz, 1H), 7.04 (d, J = 7.6 Hz, 2H), 6.97-6.78 (m, 3H), 5.60 (dd, J = 9.4, 5.7 Hz, 1H), 5.21 (t, J = 8.2 Hz, 1H), 4.33-4.02 (m, 1H), 4.00 (d, J = 10.6 Hz, 1H), 3.47 (s, 3H), 2.79-2.63 (m, 2H), 1.94 (ddd, J = 14.4, 9.5, 5.2 Hz, 1H), 1.80 (ddd, J = 14.2, 8.6, 5.6 Hz, 1H), 1.72-1.57 (m, 1H), 0.99 (dd, J = 18.4, 6.5 Hz, 6H). |
| 80 | 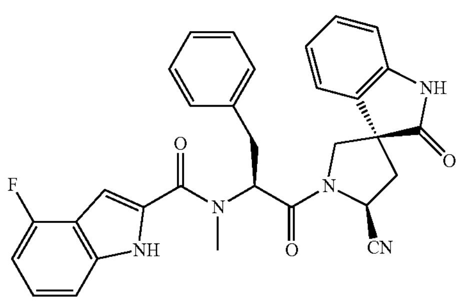 [SMILES: CN(C(=O)c1cc2c(F)cccc2[nH]1)[C@@H](Cc1ccccc1)C(=O)N1C[C@]2(C[C@H]1C#N)C(=O)Nc1ccccc12] | [M − H]− 534.19 | 1H NMR (400 MHz, Acetone-d6) δ 10.59 (s, 1H), 9.64 (s, 1H), 7.42-7.35 (m, 2H), 7.32-7.21 (m, 3H), 7.24-7.13 (m, 2H), 7.02 (dt, J = 7.4, 1.9 Hz, 2H), 6.92-6.85 (m, 1H), 6.85-6.74 (m, 3H), 5.76 (dd, J = 8.6, 6.7 Hz, 1H), 5.21 (t, J = 8.3 Hz, 1H), 4.24 (d, J = 10.6 Hz, 1H), 3.73 (d, J = 10.6 Hz, 1H), 3.53 (s, 3H), 3.40 (dd, J = 14.0, 6.7 Hz, 1H), 3.26 (dd, J = 14.1, 8.6 Hz, 1H), 2.72 (ddd, J = 13.3, 8.5, 1.1 Hz, 1H), 2.62 (dd, J = 13.2, 8.0 Hz, 1H). |
| 81 | 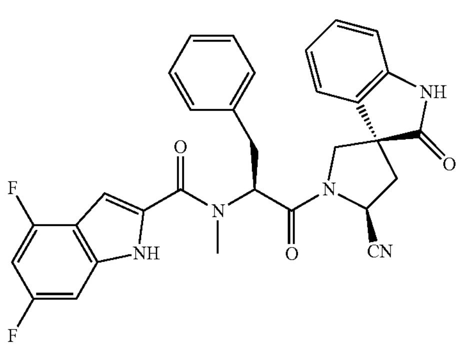 [SMILES: CN(C(=O)c1cc2c(F)cc(F)cc2[nH]1)[C@@H](Cc1ccccc1)C(=O)N1C[C@]2(C[C@H]1C#N)C(=O)Nc1ccccc12] | [M − H]− 552.18 | 1H NMR (400 MHz, Acetone-d6) δ 10.69 (s, 1H), 9.65 (s, 1H), 7.41-7.34 (m, 2H), 7.29-7.21 (m, 2H), 7.24-7.13 (m, 1H), 7.07-6.97 (m, 3H), 6.89 (d, J = 7.6 Hz, 1H), 6.85 (s, 1H), 6.79 (t, J = 7.5 Hz, 1H), 6.72 (td, J = 10.3, 2.1 Hz, 1H), 5.76 (dd, J = 8.8, 6.6 Hz, 1H), 5.21 (t, J = 8.3 Hz, 1H), 4.25 (d, J = 10.7 Hz, 1H), 3.73 (d, J = 10.6 Hz, 1H), 3.52 (s, 3H), 3.39 (dd, J = 14.1, 6.7 Hz, 1H), 3.26 (dd, J = 14.1, 8.8 Hz, 1H), 2.72 (ddd, J = 13.2, 8.5, 1.2 Hz, 1H), 2.63 (dd, J = 13.3, 8.1 Hz, 1H). |

-continued

| Example | Structure | MS | NMR |
|---|---|---|---|
| 82 | 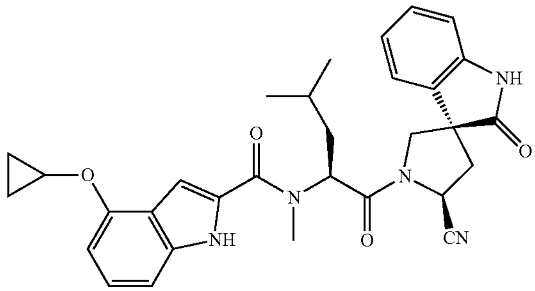 [SMILES: CC(C)C[C@@H](C(=O)N1C[C@]2(C[C@H]1C#N)C(=O)Nc1ccccc12)N(C)C(=O)c1cc2c(OC3CC3)cccc2[nH]1] | [M + Na]⁺ 562.24 | $^1$H NMR (400 MHz, Acetone-$d_6$) δ 10.39 (s, 1H), 9.67 (s, 1H), 7.17 (t, J = 7.9 Hz, 1H), 7.13-6.96 (m, 3H), 6.87 (td, J = 18.4, 16.6, 7.2 Hz, 5H), 5.58 (d, J = 9.4 Hz, 1H), 5.20 (t, J = 8.2 Hz, 1H), 4.27 (d, J = 10.8 Hz, 1H), 4.03-3.92 (m, 1H), 3.43 (s, 3H), 3.38 (d, J = 7.2 Hz, 1H), 2.78-2.62 (m, 2H), 1.99-1.85 (m, 1H), 1.77 (dt, J = 14.2, 7.2 Hz, 1H), 1.63 (dd, J = 14.3, 7.7 Hz, 1H), 1.45-1.35 (m, 2H), 1.34-1.28 (m, 1H), 1.19 (q, J = 8.0, 7.3 Hz, 1H), 1.01 (d, J = 6.7 Hz, 3H), 0.95 (d, J = 6.6 Hz, 3H). |
| 83 | 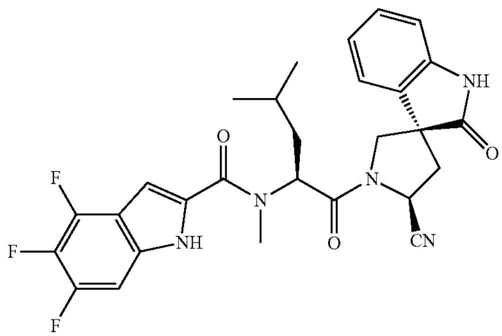 [SMILES: CC(C)C[C@@H](C(=O)N1C[C@]2(C[C@H]1C#N)C(=O)Nc1ccccc12)N(C)C(=O)c1cc2c(F)c(F)c(F)cc2[nH]1] | [M + Na]⁺ 560.19 | 1H NMR (400 MHz, Acetone-$d_6$) δ 10.87 (s, 1H), 9.69 (s, 1H), 7.31-7.20 (m, 1H), 7.09-6.95 (m, 3H), 6.91 (d, J = 7.7 Hz, 1H), 6.80 (t, J = 7.5 Hz, 1H), 5.58 (dd, J = 9.5, 5.6 Hz, 1H), 5.21 (t, J = 8.3 Hz, 1H), 4.29 (d, J = 10.7 Hz, 1H), 3.98 (d, J = 10.6 Hz, 1H), 3.46 (s, 3H), 2.81-2.58 (m, 2H), 1.94 (ddd, J = 14.4, 9.6, 5.0 Hz, 1H), 1.78 (ddd, J = 14.2, 8.8, 5.6 Hz, 1H), 1.70-1.55 (m, 1H), 1.01 (d, J = 6.6 Hz, 3H), 0.96 (d, J = 6.5 Hz, 3H). |
| 84 | 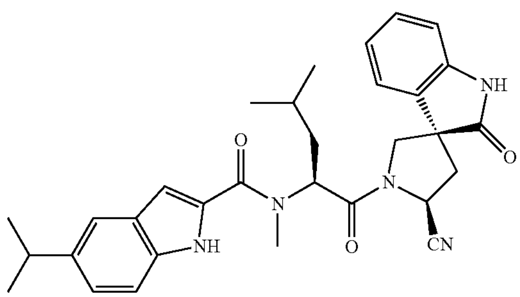 [SMILES: CC(C)C[C@@H](C(=O)N1C[C@]2(C[C@H]1C#N)C(=O)Nc1ccccc12)N(C)C(=O)c1cc2cc(C(C)C)ccc2[nH]1] | [M + Na]⁺ 548.26 | $^1$H NMR (400 MHz, Acetone-$d_6$) δ 10.28 (s, 1H), 9.68 (s, 1H), 7.54 (s, 1H), 7.20-6.97 (m, 3H), 6.97-6.72 (m, 3H), 5.58 (dd, J = 9.4, 5.6 Hz, 1H), 5.21 (t, J = 8.2 Hz, 1H), 4.25 (d, J = 10.6 Hz, 1H), 4.01 (d, J = 10.6 Hz, 1H), 3.43 (s, 3H), 3.01 (td, J = 13.5, 6.6 Hz, 1H), 2.81-2.60 (m, 2H), 2.01-1.85 (m, 1H), 1.78 (ddd, J = 14.2, 8.7, 5.6 Hz, 1H), 1.63 (dq, J = 13.6, 6.6 Hz, 1H), 1.29 (d, J = 6.9 Hz, 6H), 1.01 (d, J = 6.6 Hz, 3H), 0.99-0.89 (m, 3H). |
| 85 | 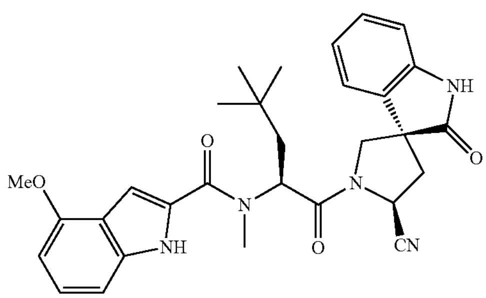 [SMILES: COc1cccc2[nH]c(C(=O)N(C)[C@@H](CC(C)(C)C)C(=O)N3C[C@]4(C[C@H]3C#N)C(=O)Nc3ccccc34)cc12] | [M + Na]⁺ 550.24 | $^1$H NMR (400 MHz, Chloroform-d) δ 8.81 (s, 1H), 8.14 (s, 1H), 7.20 (t, J = 8.0 Hz, 1H), 7.04-6.89 (m, 3H), 6.83 (d, J = 7.8 Hz, 1H), 6.73-6.58 (m, 2H), 6.50 (d, J = 7.8 Hz, 1H), 5.59 (t, J = 6.4 Hz, 1H), 5.00 (t, J = 8.6 Hz, 1H), 4.65 (d, J = 10.4 Hz, 1H), 4.01-3.91 (m, 1H), 3.99 (s, 3H), 3.49 (s, 3H), 2.94-2.78 (m, 1H), 2.51 (dd, J = 13.2, 8.5 Hz, 1H), 2.11 (q, J = 6.5, 5.3 Hz, 1H), 1.74 (dd, J = 14.3, 6.0 Hz, 1H), 0.99 (s, 9H). |
| 86 | 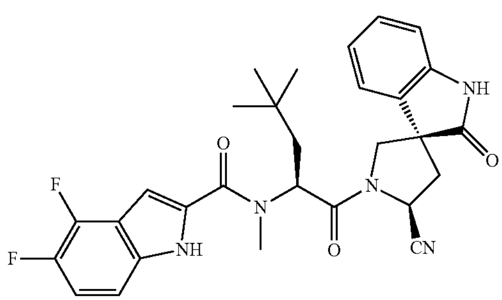 [SMILES: CN(C(=O)c1cc2c(F)c(F)ccc2[nH]1)[C@@H](CC(C)(C)C)C(=O)N1C[C@]2(C[C@H]1C#N)C(=O)Nc1ccccc12] | [M + Na]⁺ 556.21 | $^1$H NMR (500 MHz, Chloroform-d) δ 9.21 (s, 1H), 8.67 (s, 1H), 7.10 (ddd, J = 10.6, 8.9, 7.3 Hz, 1H), 7.07-6.89 (m, 2H), 6.89-6.74 (m, 2H), 6.74-6.54 (m, 2H), 5.55 (t, J = 6.4 Hz, 1H), 5.03 (t, J = 8.5 Hz, 1H), 4.48 (d, J = 10.5 Hz, 1H), 3.98 (d, J = 10.5 Hz, 1H), 3.48 (s, 3H), 2.86 (dd, J = 13.3, 8.7 Hz, 1H), 2.52 (ddd, J = 13.3, 8.4, 1.3 Hz, 1H), 2.20-2.13 (m, 1H), 1.73 (dd, J = 14.3, 6.0 Hz, 1H), 0.99 (s, 9H). |

| Example | Structure | MS | NMR |
|---|---|---|---|
| 87 | 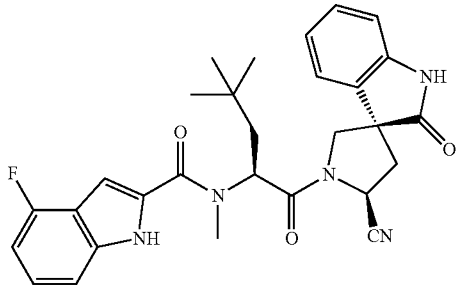 [SMILES: CN(C(=O)c1cc2c(F)cccc2[nH]1)[C@@H](CC(C)(C)C)C(=O)N1C[C@]2(C[C@H]1C#N)C(=O)Nc1ccccc12] | [M + Na]⁺ 538.22 | |
| 88 | 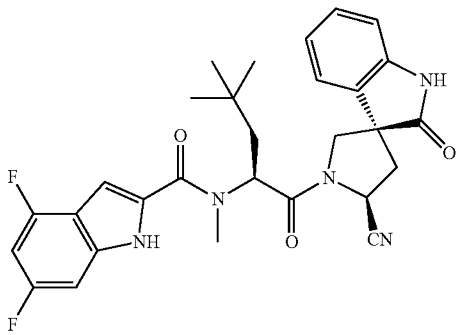 [SMILES: CN(C(=O)c1cc2c(F)cc(F)cc2[nH]1)[C@@H](CC(C)(C)C)C(=O)N1C[C@]2(C[C@H]1C#N)C(=O)Nc1ccccc12] | [M + Na]⁺ 556.21 | $^1$H NMR (400 MHz, Chloroform-d) δ 9.34 (s, 1H), 8.79 (s, 1H), 6.96 (t, J = 7.6 Hz, 1H), 6.89-6.79 (m, 3H), 6.73-6.54 (m, 3H), 5.57 (t, J = 6.4 Hz, 1H), 5.03 (t, J = 8.5 Hz, 1H), 4.51 (d, J = 10.5 Hz, 1H), 3.97 (d, J = 10.5 Hz, 1H), 3.47 (s, 3H), 2.85 (dd, J = 13.3, 8.5 Hz, 1H), 2.52 (dd, J = 13.3, 8.5 Hz, 1H), 2.21-2.11 (m, 1H), 1.76 (d, J = 6.2 Hz, 1H), 0.99 (s, 9H). |

Example 89

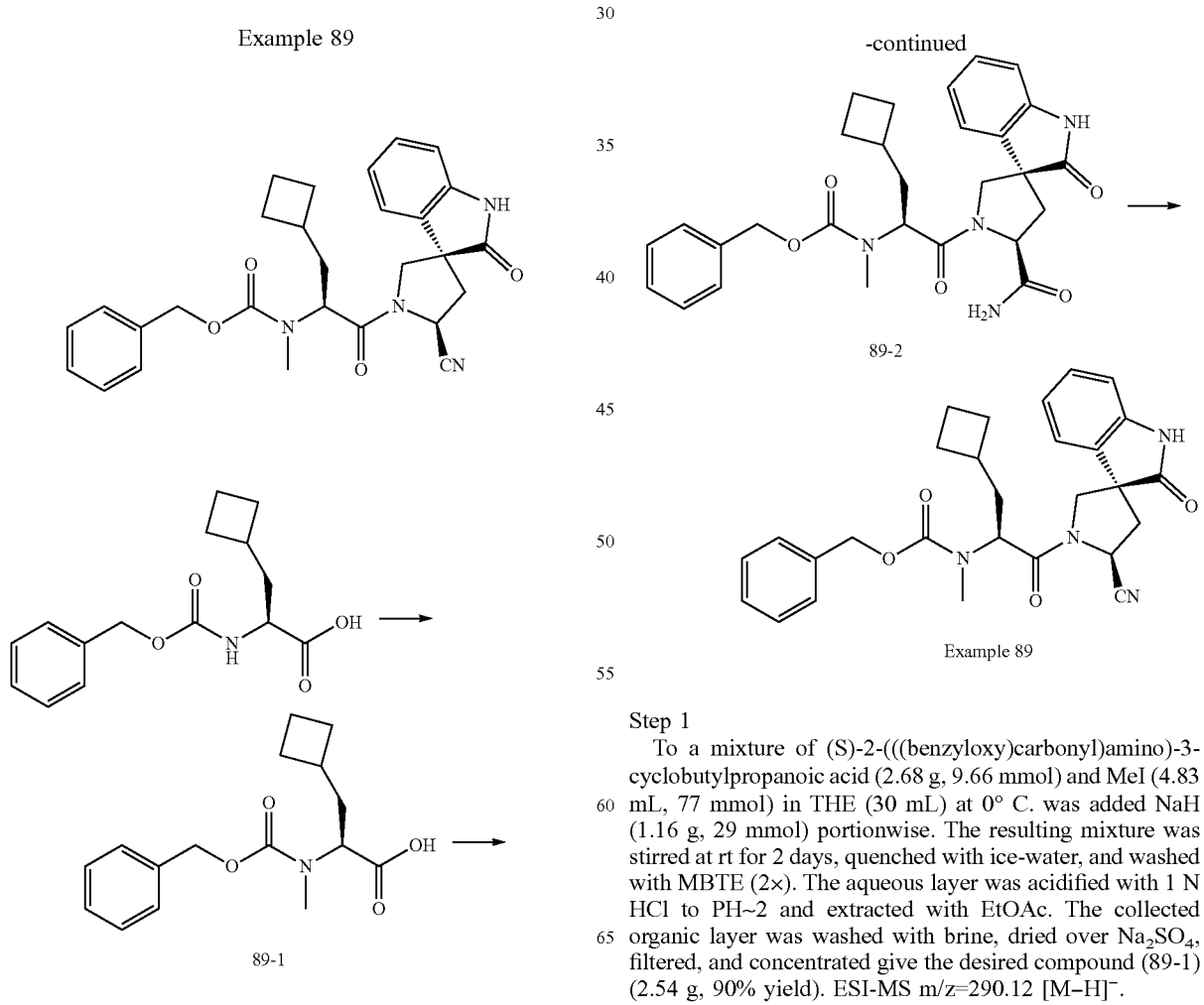

Step 1

To a mixture of (S)-2-(((benzyloxy)carbonyl)amino)-3-cyclobutylpropanoic acid (2.68 g, 9.66 mmol) and MeI (4.83 mL, 77 mmol) in THF (30 mL) at 0° C. was added NaH (1.16 g, 29 mmol) portionwise. The resulting mixture was stirred at rt for 2 days, quenched with ice-water, and washed with MBTE (2×). The aqueous layer was acidified with 1 N HCl to PH~2 and extracted with EtOAc. The collected organic layer was washed with brine, dried over Na₂SO₄, filtered, and concentrated give the desired compound (89-1) (2.54 g, 90% yield). ESI-MS m/z=290.12 [M–H]⁻.

Step 2

To a solution of compound (1-4) (2.33 g, 6.96 mmol), compound (89-1) (2.54 g, 8.70 mmol) and 4-methylmorpholine (3.06 mL, 27.9 mmol) in DCM/DMF (5/5 mL) was added HATU (2.78 g, 7.31 mmol). The mixture was stirred at rt for 2 h, quenched with water, and extracted with EtOAc. The collected organic layer was washed with water, 1N HCl, sat NaHCO₃ and brine, dried over Na₂SO₄, filtered, and concentrated. Purification of the residue on silica gel column provided compound (89-2) (3.16 g, 90% yield). ESI-MS m/z=503.19 [M−H]⁻.

Step 3

To a mixture of compound (89-2) (45 mg, 0.089 mmol) and Et₃N (99 µl, 0.713 mmol) in DCM (1 mL) at 0° C. was added dropwise TFAA (50.4 µl, 0.357 mmol). The resulting mixture was stirred at rt for 30 min, quenched with cold sat. NaHCO₃ solution, and extracted with EtOAc. The collected organic layer was washed with water, 1N HCl, sat NaHCO₃, and brine, dried over Na₂SO₄, filtered, and concentrated. Purification of the residue on silica gel column provided Example 89 (23 mg, 53% yield). ESI-MS m/z=485.19 [M−H]⁻.

The following example was prepared employing similar protocol as described above.

| Example # | Structure | MS |
|---|---|---|
| 90 | 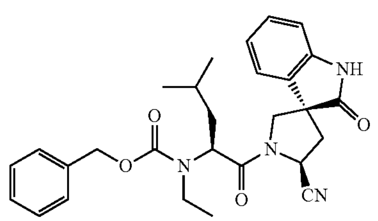 [SMILES: CCN(C(=O)OCc1ccccc1)[C@@H](CC(C)C)C(=O)N1C[C@]2(C[C@H]1C#N)C(=O)Nc1ccccc12] | [M − H] 487.19 |

Example 91

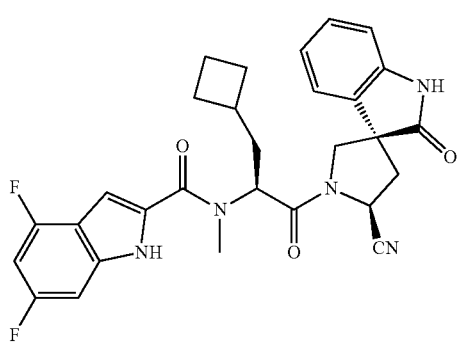 [SMILES: CN(C(=O)c1cc2c(F)cc(F)cc2[nH]1)[C@@H](CC1CCC1)C(=O)N1C[C@]2(C[C@H]1C#N)C(=O)Nc1ccccc12]

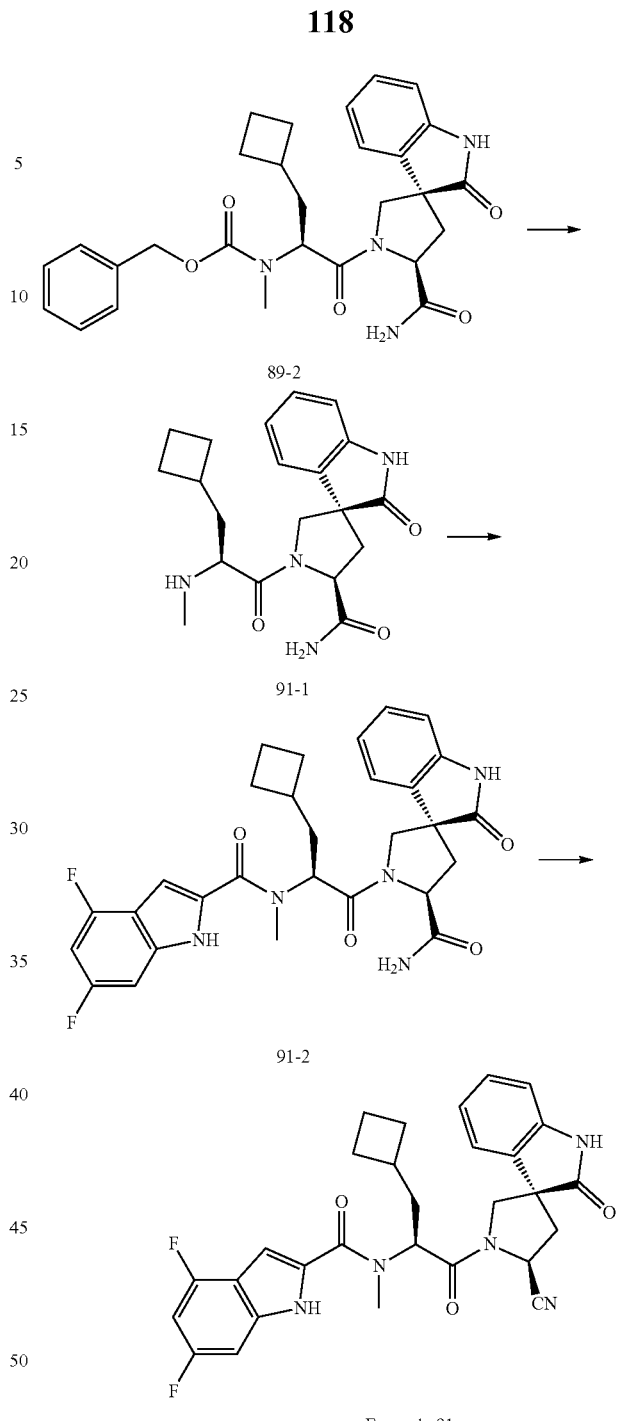

Example 91

Step 1

A mixture of compound (89-2) (65 mg, 0.13 mmol) and Pd—C (13.7 mg, 0.013 mmol) in MeOH (1 mL) was treated with H2 using a hydrogen balloon. After 1 h, the mixture was diluted with DCM, filtered through celite, and concentrated to give compound (91-1) (48 mg, 100%). ESI-MS m/z=369.19 [M−H]⁻.

Step 2

To a mixture of compound (91-1) (0.032 g, 0.086 mmol), 4,6-difluoro-1H-indole-2-carboxylic acid (0.021 g, 0.108 mmol), DIPEA (0.045 mL, 0.258 mmol) in DCM/DMF (0.5/0.5 mL) at rt was added HATU (39 mg, 0.103 mmol). The resulting mixture was stirred at rt for 20 h, quenched water, and extracted with EtOAc. The collected organic layer was washed with water and brine, dried over Na₂SO₄, filtered, and concentrated. Purification of the residue on silica gel column provided compound (91-2) (34 mg, 72% yield). ESI-MS m/z=548.21 [M–H].

Step 3

To a mixture of compound (91-2) (34 mg, 0.062 mmol) and Et₃N (86 μl, 0.619 mmol) in DCM (1 mL) at 0° C. was added TFAA (44 μl, 0.31 mmol). The mixture was stirred at rt for 30 min, quenched with cold sat. NaHCO₃, and extracted with EtOAc. The collected organic layer was washed with 1 N HCl, sat. NaHCO₃, brine, dried over Na₂SO₄, filtered, and concentrated. Purification of the residue on silica gel chromatography with 0-40% acetone/cyclohexane provided Example 91 (17 mg, 52% yield). ESI-MS m/z=530.20 [M–H]⁻. ¹H NMR (400 MHz, Acetone-d₆) δ 10.65 (s, 1H), 9.51 (s, 1H), 6.97-6.83 (m, 3H), 6.81-6.72 (m, 2H), 6.67 (t, J=7.6 Hz, 1H), 6.60 (td, J=10.3, 2.1 Hz, 1H), 5.28 (t, J=7.4 Hz, 1H), 5.05 (t, J=8.2 Hz, 1H), 4.08 (d, J=10.7 Hz, 1H), 3.82 (d, J=10.6 Hz, 1H), 3.28 (s, 3H), 2.69 (s, 1H), 2.67-2.48 (m, 2H), 2.22 (hept, J=7.7 Hz, 1H), 1.89 (d, J=7.4 Hz, 3H), 1.74-1.53 (m, 4H).

The following examples were prepared employing similar protocol as described above.

| Example # | Structure | MS | NMR |
|---|---|---|---|
| 92 | 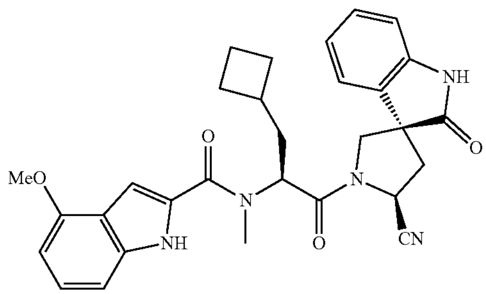 [SMILES: COc1cccc2[nH]c(C(=O)N(C)[C@@H](CC3CCC3)C(=O)N3C[C@]4(C[C@H]3C#N)C(=O)Nc3ccccc34)cc12] | [M – H]⁻ 524.23 | ¹H NMR (400 MHz, Acetone-d₆) δ 10.25 (s, 1H), 9.50 (s, 1H), 7.05-6.97 (m, 1H), 6.96-6.85 (m, 3H), 6.75 (dd, J = 4.9, 2.7 Hz, 2H), 6.68 (t, J = 7.5 Hz, 1H), 6.43-6.36 (m, 1H), 5.28 (t, J = 7.5 Hz, 1H), 5.04 (t, J = 8.1 Hz, 1H), 4.09 (d, J = 10.6 Hz, 1H), 3.83 (d, J = 9.9 Hz, 4H), 3.28 (s, 3H), 2.69 (s, 1H), 2.60 (ddd, J = 13.3, 8.6, 1.0 Hz, 1H), 2.53 (dd, J = 13.3, 7.6 Hz, 1H), 2.22 (dt, J = 15.0, 7.7 Hz, 1H), 1.89 (d, J = 7.6 Hz, 2H), 1.89 (s, 1H), 1.74-1.63 (m, 1H), 1.66-1.53 (m, 3H). |
| 93 | 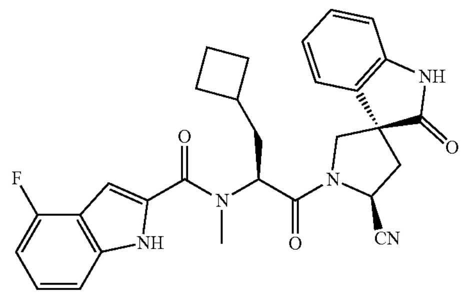 [SMILES: CN(C(=O)c1cc2c(F)cccc2[nH]1)[C@@H](CC1CCC1)C(=O)N1C[C@]2(C[C@H]1C#N)C(=O)Nc1ccccc12] | [M – H]⁻ 512.18 | ¹H NMR (400 MHz, Acetone-d₆) δ 10.72 (s, 1H), 9.66 (s, 1H), 7.33 (d, J = 8.3 Hz, 1H), 7.21 (td, J = 8.0, 5.2 Hz, 1H), 7.04 (d, J = 7.6 Hz, 2H), 6.94-6.87 (m, 2H), 6.87-6.76 (m, 2H), 5.44 (t, J = 7.5 Hz, 1H), 5.21 (t, J = 8.2 Hz, 1H), 4.22 (d, J = 10.6 Hz, 1H), 3.98 (d, J = 10.6 Hz, 1H), 3.44 (s, 3H), 2.76 (ddd, J = 13.3, 8.6, 1.0 Hz, 1H), 2.68 (dd, J = 13.3, 7.8 Hz, 1H), 2.38 (p, J = 7.7 Hz, 1H), 2.04 (m, 2H), 2.03 (s, 1H), 1.98 (s, 1H), 1.89-1.68 (m, 4H). |
| 94 | 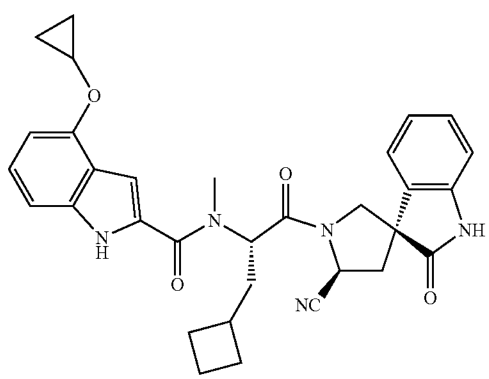 [SMILES: CN(C(=O)c1cc2c(OC3CC3)cccc2[nH]1)[C@@H](CC1CCC1)C(=O)N1C[C@]2(C[C@H]1C#N)C(=O)Nc1ccccc12] | [M + Na]⁺ 57.25 | |
| 95 | 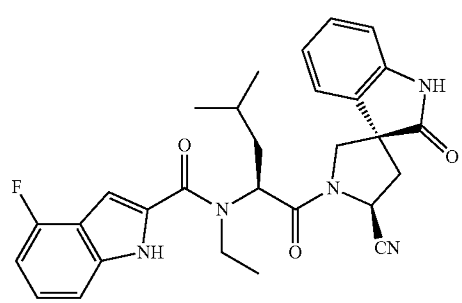 [SMILES: CCN(C(=O)c1cc2c(F)cccc2[nH]1)[C@@H](CC(C)C)C(=O)N1C[C@]2(C[C@H]1C#N)C(=O)Nc1ccccc12] | [M – H]⁻ 514.22 | |

Example 96

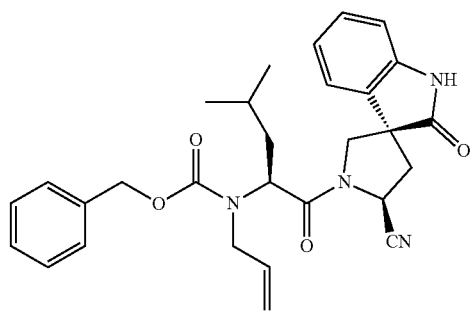 [SMILES: C=CCN(C(=O)OCc1ccccc1)[C@@H](CC(C)C)C(=O)N1C[C@]2(C[C@H]1C#N)C(=O)Nc1ccccc12]

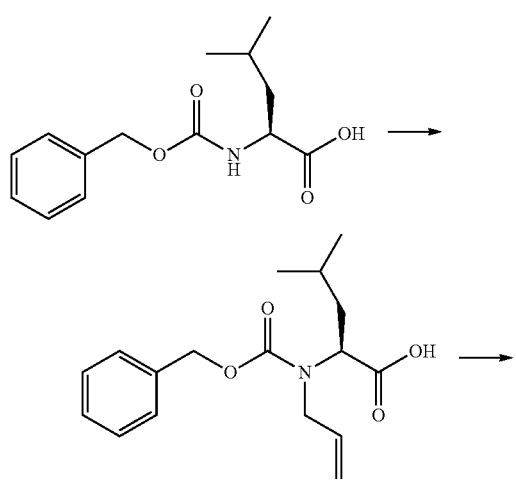

96-1

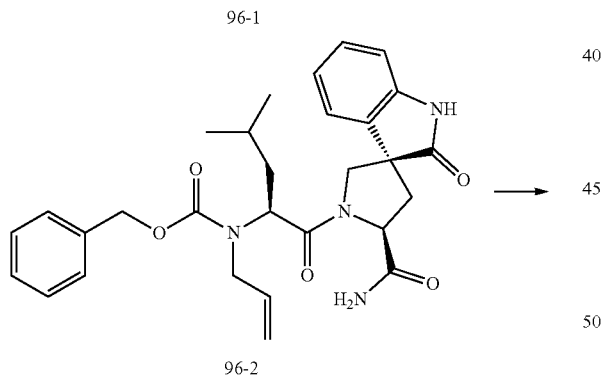

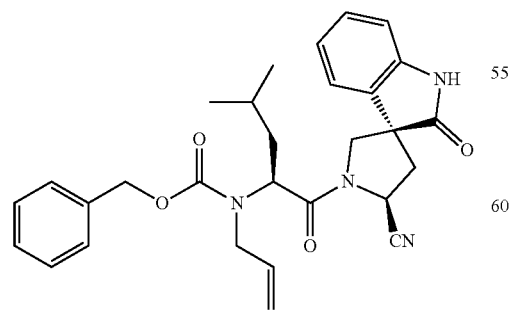

Example 96

Step 1

To a solution of ((benzyloxy)carbonyl)-L-leucine (1.56 g, 5.88 mmol) and 3-iodoprop-1-ene (0.807 mL, 8.82 mmol) in THF (30 mL) at 0° C. was added NaH (0.706 g, 17.64 mmol) in portions. The mixture was stirred at rt for 4 days, quenched with ice-water, and washed with MBTE twice. The aqueous layer was acidified with 1 N HCl to PH~2, and extracted with EtOAc. The collected organic layer was washed with brine, dry over $Na_2SO_4$, filtered, and concentrated to afford compound (96-1) (1.15 g, 64.0% yield). ESI-MS m/z=304.12 [M–H]$^-$.

Step 2

To a mixture of compound (1-4) (221 mg, 0.826 mmol), compound (96-1) (265 mg, 0.868 mmol) and DIPEA (577 µl, 3.31 mmol) in DCM/DMF (0.8/0.8 mL) was added HATU (314 mg, 0.826 mmol). The resulting mixture was stirred at rt for 16 h, quenched with water, and extracted with EtOAc. The organic layer was washed with water, 1N HCl, sat $NaHCO_3$ and brine, dried over $Na_2SO_4$, filtered, and concentrated. Purification of the residue by silica gel chromatography with 0-10% MeOH/DCM provided compound (96-2) (262 mg, 61.1% yield). ESI-MS m/z=517.20 [M–H]$^-$.

Step 3

To a mixture of compound (96-2) (22 mg, 0.042 mmol) and $Et_3N$ (59.1 µl, 0.424 mmol) in DCM (1 mL) at 0° C. was added TFAA (30.0 µl, 0.212 mmol). The mixture was stirred at rt for 30 min, quenched with cold sat. $NaHCO_3$ solution, and extracted with EtOAc. The organic layer was washed with water, 1N HCl, sat $NaHCO_3$ and brine, dried over $Na_2SO_4$, filtered, and concentrated. Purification of the residue on silica gel chromatography with 0-50% acetone/cyclohexane provided Example 96 (20 mg, 94% yield). ESI-MS m/z=499.20 [M–H].

Example 97

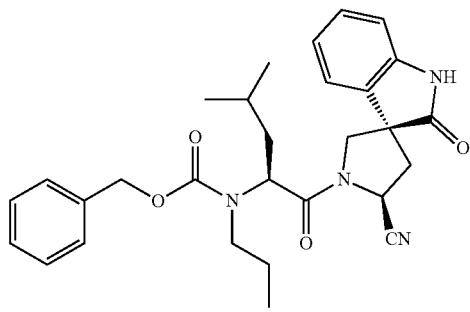 [SMILES: CCCN(C(=O)OCc1ccccc1)[C@@H](CC(C)C)C(=O)N1C[C@]2(C[C@H]1C#N)C(=O)Nc1ccccc12]

96-2

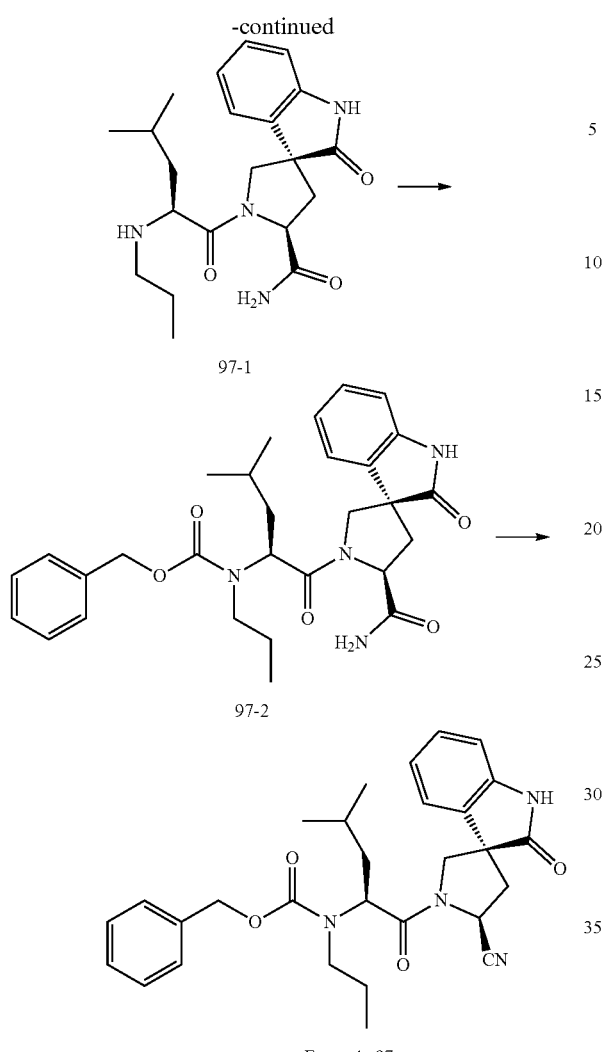

97-1

97-2

Example 97

Step 1

A mixture of compound (96-2) (105 mg, 0.202 mmol) and Pd—C (21.55 mg, 0.020 mmol) in MeOH (3 mL) was stirred under $H_2$ using a hydrogen balloon. After 1 h, the mixture was diluted with DCM, filtered through celite, and concentrated to give compound (97-1) (79 mg, 100%). ESI-MS m/z=385.19 [M−H]⁻.

Step 2

To a mixture of compound (97-1) (0.039 g, 0.10 mmol) in DCM/DMF (0.5/0.5 mL) and $Et_3N$ (0.098 mL, 0.70 mmol) was added Cbz-Cl (0.042 mL, 0.30 mmol). The mixture was stirred at rt for 16 h, quenched with aqueous $NH_3$, and extracted with EtOAc. The organic layer was washed with water and brine, dried over $N_2SO_4$, filtered, and concentrated. Purification of the residue by silica gel chromatography with 0-10% MeOH/DCM provided (97-2) (10 mg, 19% yield). ESI-MS m/z=519.22 [M−H]⁻.

Step 3

To a mixture compound (97-2) (10 mg, 0.019 mmol) and $Et_3N$ (53.5 µl, 0.384 mmol) in DCM (0.5 mL) was added TFAA (27.1 µl, 0.192 mmol) at 0° C. quenched with cold sat. $NaHCO_3$ solution, and extracted with EtOAc. The organic layer was washed with 1 N HCl, sat. $NaHCO_3$ solution and brine, dried over $Na_2SO_4$, filtered, and concentrated. Purification of the residue by silica gel chromatography with 0-50% acetone/cyclohexane provided Example 97 (7.0 mg, 72.5% yield) ESI-MS m/z=501.22 [M−H]⁻.

Example 98

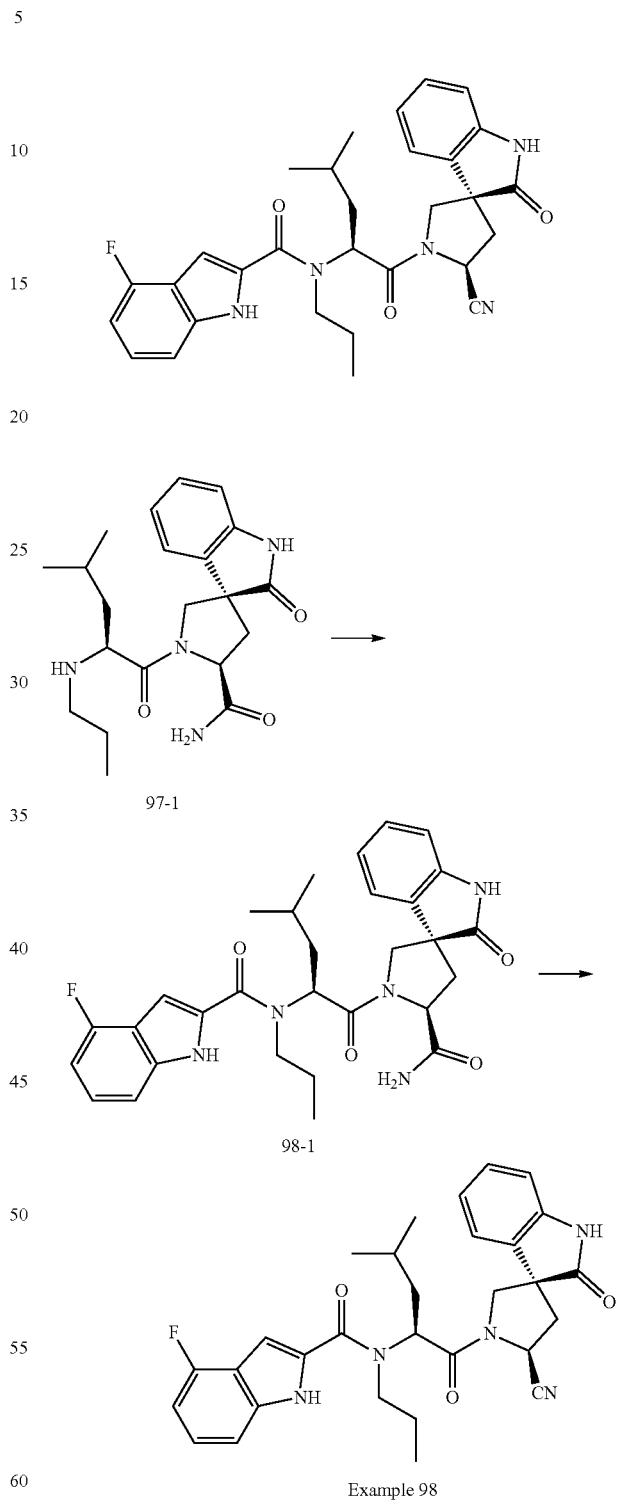

97-1

98-1

Example 98

Step 1

A mixture of 4-fluoro-1H-indole-2-carboxylic acid (0.054 g, 0.30 mmol) and 1-chloro-N,N,2-trimethylprop-1-en-1-amine (0.044 mL, 0.330 mmol) in DCM (1 mL) was stirred at rt for 1 h. The resulting mixture was added to a solution of compound (97-1) and Et₃N (0.108 mL, 0.85 mmol) in DCM/DMF (0.5/0.5 mL). The resulting mixture was stirred rt for 20 h, quenched aqueous NH₃, and extracted with EtOAc. The organic layer was washed with water and brine, dried over Na₂SO₄, filtered, and concentrated. Purification of the residue by silica gel chromatography with 0-10% MeOH/DCM provided compound (98-1)(40 mg, 69% yield). ESI-MS m/z=546.23 [M–H]⁻.

Step 2

To a mixture of compound (98-1) (40 mg, 0.073 mmol) and Et₃N (10.18 µl, 0.073 mmol) in DCM (1 mL) at 0° C. was added TFAA (10.32 µl, 0.073 mmol). The mixture was stirred at rt for 30 min, quenched with cold sat. NaHCO₃, and extracted with EtOAc. The organic layer was washed with 1 N HCl, sat. NaHCO₃ and brine, dried over Na₂SO₄, filtered, and concentrated. Purification of the residue by silica gel chromatography with 0-50% acetone/cyclohexane provided Example 98 (35 mg, 90% yield) ESI-MS m/z=528.20 [M–H]⁻.

The following example was prepared employing similar protocol as described above.

| Example # | Structure | MS |
|---|---|---|
| 99 | 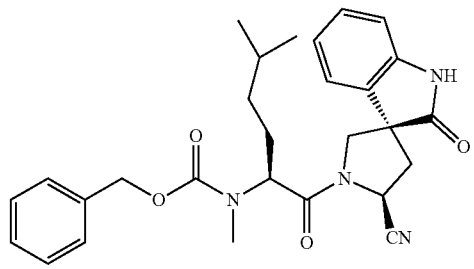 [SMILES: CC(C)CC[C@@H](C(=O)N1C[C@]2(C[C@H]1C#N)C(=O)Nc1ccccc12)N(C)C(=O)OCc1ccccc1] | [M – H] 546.23 |

Example 100

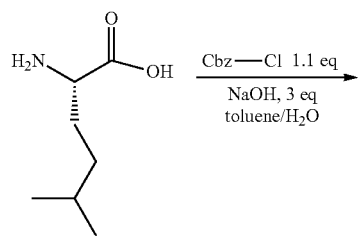

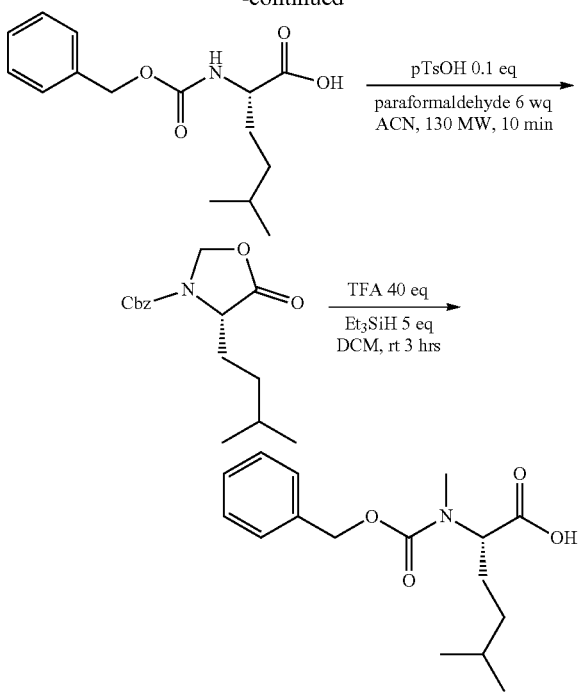

Synthesis of (S)-2-(((benzyloxy)carbonyl)(methyl) amino)-5-methylhexanoic acid

Step 1

To a mixture of (S)-2-amino-5-methylhexanoic acid (0.9 g, 6.20 mmol) in toluene/water (12.4 mL/3 mL) at 0° C. was added 2N NaOH (9.30 mL, 18.59 mmol), followed by addition of Cbz-Cl (0.973 mL, 6.82 mmol). After stirring at rt for 2 hrs, the two layers were separated, and the aqueous layer was washed with MBTE (2×), and then acidified to pH~ 2 with 1 N HCl solution at 0° C. The mixture was extracted with EtOAc (3×). The combined organics were washed with brine, dried over Na₂SO₄, and concentrated to give (S)-2-(((benzyloxy)carbonyl)amino)-5-methylhexanoic acid (1.42 g, 5.08 mmol, 82% yield), which was used in the next step without further purification. LC-MS, ES–: 277.77 [M–1].

Step 2

To a solution of (S)-2-(((benzyloxy)carbonyl)amino)-5-methylhexanoic acid (660 mg, 2.363 mmol) and paraformaldehyde (426 mg, 14.18 mmol)) in dry acetonitrile (11.8 mL) was added 4-methylbenzenesulfonic acid hydrate (44.9 mg, 0.236 mmol). The resulting mixture was heated under microwave at 130° C. for 10 min. After cooling to rt, the mixture was filtered through celite, concentrated, and chased with DCM to give the crude benzyl (S)-4-isopentyl-5-oxooxazolidine-3-carboxylate as a sticky oil, which was used in the next step without further purification.

Step 3

To the crude benzyl (S)-4-isopentyl-5-oxooxazolidine-3-carboxylate from previous step was added DCM (24 mL), triethylsilane (1.89 mL, 11.81 mmol), and 2,2,2-trifluoroacetic acid (7.28 mL, 95 mmol). The mixture was stirred at rt for 2 hrs, concentrated, and chased with DCM (3×). The residue was basified with 1N NaOH at 0° C. to pH~ 10, and washed with EtOAc (1×) and MBTE (1×). The aqueous layer was acidified to pH~ 2 with 1N HCl, and extracted with EtOAc (2×). The combined organics were washed with brine, dried, and concentrated to give (S)-2-(((benzyloxy)carbonyl)(methyl)amino)-5-methylhexanoic acid (715 mg, 92% yield for 2 steps). 1H NMR (400 MHz, DMSO-d$_6$) δ 12.56 (s, 1H), 7.41-7.27 (m, 5H), 5.17-5.00 (m, 2H), 4.48 (ddd, J=27.4, 11.1, 4.7 Hz, 1H), 2.81 (s, 2H, N-Me rotamer), 2.78 (s, 1H, N-Me rotamer), 1.84 (tq, J=9.6, 4.6, 4.1 Hz, 1H), 1.70 (ddd, J=14.4, 9.6, 4.5 Hz, 1H), 1.52 (dt, J=12.8, 6.5 Hz, 1H), 1.21-0.99 (m, 2H), 0.84 (dd, J=9.2, 6.6 Hz, 6H).

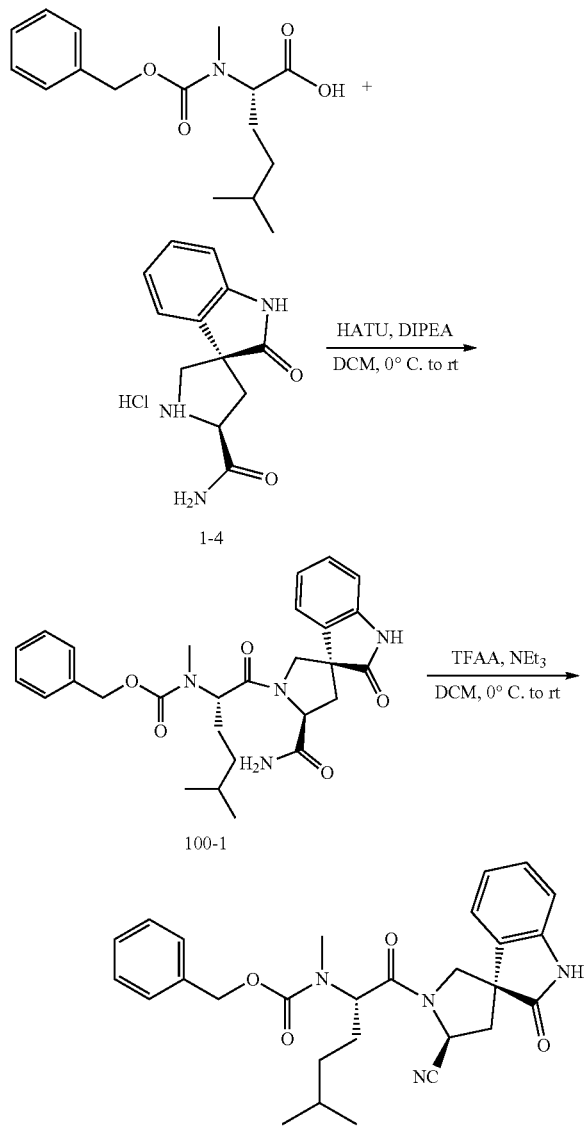

Synthesis of Example 100

Step 1

To a mixture of (S)-2-(((benzyloxy)carbonyl)(methyl) amino)-5-methylhexanoic acid (300 mg, 1.023 mmol) and (1-4) (261 mg, 0.974 mmol) in dry CH$_2$Cl$_2$ (2.96 mL) at 0° C. was added DIPEA (510 μl, 2.92 mmol) and HATU (481 mg, 1.266 mmol). The resulting mixture was stirred at rt for 2 hrs. The mixture was diluted with DCM, washed with water (2×), brine, dried, and concentrated. Purification of the residue on silica gel chromatography with 0-10% MeOH/ DCM provided benzyl ((S)-1-((3R,5'S)-5'-carbamoyl-2-oxospiro[indoline-3,3'-pyrrolidin]-1'-yl)-5-methyl-1-oxohexan-2-yl)(methyl)carbamate (100-1) (189 mg, 38% yield). LC-MS, ES−: 505.0 [M−1].

Step 2

To a mixture of compound (100-1) (31 mg, 0.061 mmol) and Et$_3$N (85 μL, 0.612 mmol) in dry DCM (0.8 mL) at 0° C. was added TFAA (43.2 μl, 0.306 mmol). After stirring at rt for 1 h, the reaction mixture was diluted with DCM, washed with sat NaHCO$_3$, water, brine, dried and concentrated. Purification of the residue by silica gel chromatography with 0-40% acetone/cyclohexane provided Example 100 (25 mg, 84% yield). LC-MS, ES$^+$: 488.96 [M+1].

The following examples were prepared employing similar protocol as described above.

| Example # | Structure | MS |
|---|---|---|
| 100 | 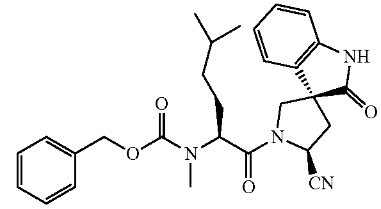 [SMILES: CC(C)CC[C@@H](C(=O)N1C[C@]2(C[C@H]1C#N)C(=O)Nc1ccccc12)N(C)C(=O)OCc1ccccc1] | above |
| 101 | 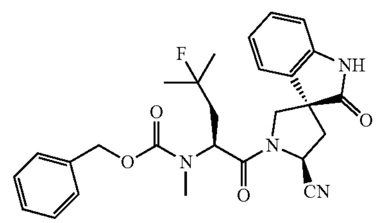 [SMILES: CN(C(=O)OCc1ccccc1)[C@@H](CC(C)(C)F)C(=O)N1C[C@]2(C[C@H]1C#N)C(=O)Nc1ccccc12] | [M + Na]$^+$ 515.20 |
| 102 | 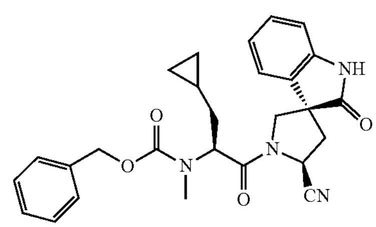 [SMILES: CN(C(=O)OCc1ccccc1)[C@@H](CC1CC1)C(=O)N1C[C@]2(C[C@H]1C#N)C(=O)Nc1ccccc12] | [M + Na]$^+$ 495.19 |
| 103 | 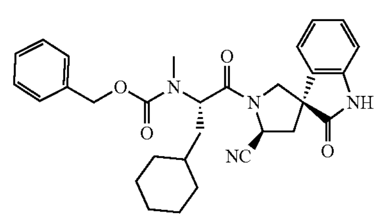 | [M + H]$^+$ 533.33 |

Example 104

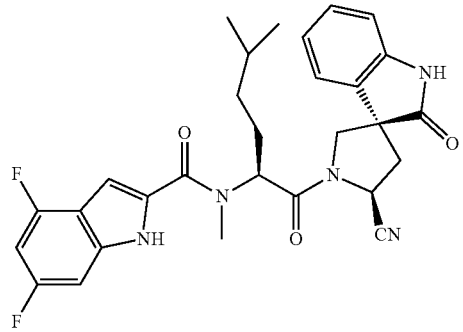 [SMILES: CC(C)CC[C@@H](C(=O)N1C[C@]2(C[C@H]1C#N)C(=O)Nc1ccccc12)N(C)C(=O)c1cc2c(F)cc(F)cc2[nH]1]

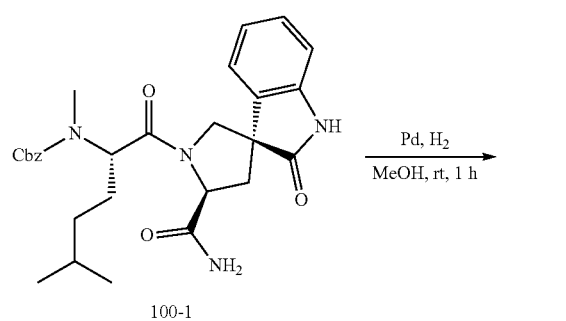

100-1

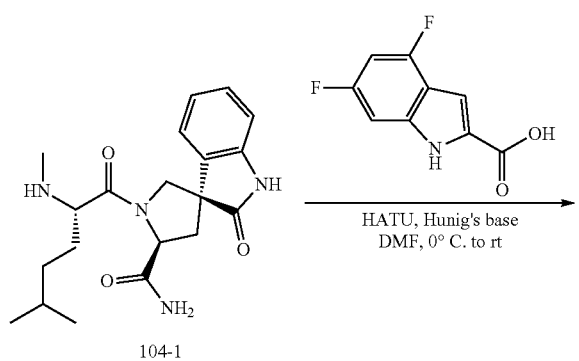

104-1

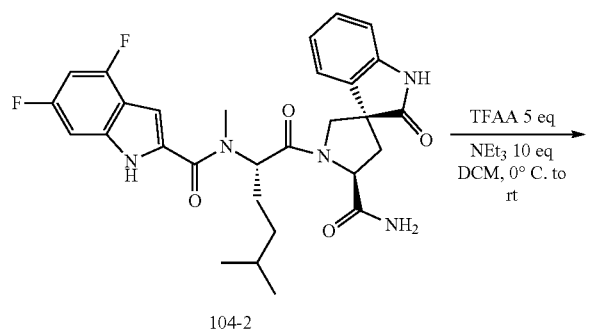

104-2

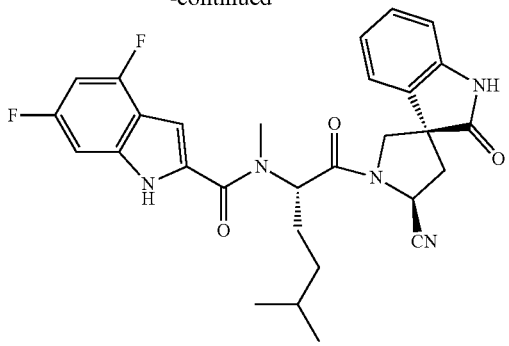

Example 104

Step 1

A mixture of compound (100-1) (152 mg, 0.300 mmol) and 10% Pd—C (31.9 mg, 0.030 mmol) in MeOH (3.00 mL) was stirred at rt under a hydrogen balloon. After 1 h, the reaction mixture was filtered through celite, rinsed with MeOH, and concentrated to give the crude (3R,5'S)-1'-((S)-5-methyl-2-(methylamino)hexanoyl)-2-oxospiro[indoline-3,3'-pyrrolidine]-5'-carboxamide (104-1) (112 mg, 0.301 mmol, 100% yield), which was used in the next step directly. LC-MS, ES+: 372.99 [M+H]$^+$.

Step 2

To a mixture of compound (104-1) (85 mg, 0.228 mmol) and 4,6-difluoro-1H-indole-2-carboxylic acid (47.2 mg, 0.240 mmol) in dry DMF (1.14 mL) at 0° C. were added Hunig's base (122 µL, 0.685 mmol) and HATU (113 mg, 0.297 mmol). The resulting mixture was then stirred at rt for 1 h, diluted with DCM, washed with water (2×) and brine. The organic layer was dried and concentrated. The crude product (104-2) was used in the next step without further purification. LC-MS, ES−: 550.2 [M−H].

Step 3

A mixture of crude (3R,5'S)-1'-((S)-2-(4,6-difluoro-N-methyl-1H-indole-2-carboxamido)-5-methylhexanoyl)-2-oxospiro[indoline-3,3'-pyrrolidine]-5'-carboxamide (104-2) (0.121 g, 0.22 mmol) and Et$_3$N (0.307 mL, 2.20 mmol) in DCM (2.9 mL) at 0° C. was treated with TFAA (0.155 mL, 1.100 mmol). After stirring at rt for 30 min, the reaction mixture was diluted with DCM, washed with sat NaHCO$_3$, water and brine, dried, and concentrated. Purification of the residue by silica gel chromatography with 0-40% acetone/cyclohexane provided Example 104 (62 mg, 53% yield for 3 steps). LC-MS, ES−: 532.01 [M−H]. 1H NMR (400 MHz, Acetone-d$_6$) δ 10.84 (s, 1H), 9.69 (s, 1H), 7.12-6.99 (m, 3H), 6.97-6.93 (m, 1H), 6.90 (d, J=7.6 Hz, 1H), 6.86-6.78 (m, 1H), 6.74 (td, J=10.3, 2.1 Hz, 1H), 5.45 (dd, J=8.8, 6.4 Hz, 1H), 5.22 (t, J=8.2 Hz, 1H), 4.26 (d, J=10.7 Hz, 1H), 3.99 (d, J=10.7 Hz, 1H), 3.46 (s, 3H), 2.74-2.64 (m, 2H), 2.04-1.91

The following examples were prepared employing similar protocol as described above.

| Example # | Structure | MS | NMR |
|---|---|---|---|
| 105 | 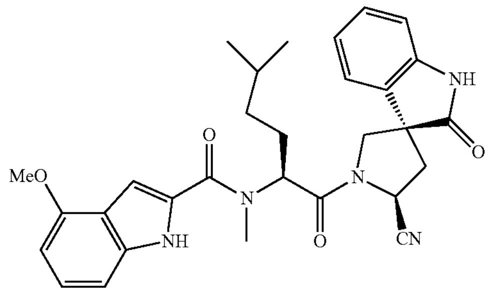 [SMILES: COc1cccc2[nH]c(C(=O)N(C)[C@@H](CCC(C)C)C(=O)N3C[C@]4(C[C@H]3C#N)C(=O)Nc3ccccc34)cc12] | [M + H]+ 528.00 | |
| 106 | 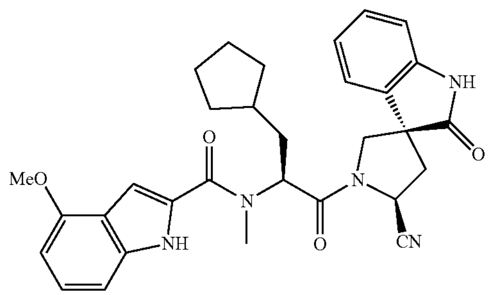 [SMILES: COc1cccc2[nH]c(C(=O)N(C)[C@@H](CC3CCCC3)C(=O)N3C[C@]4(C[C@H]3C#N)C(=O)Nc3ccccc34)cc12] | [M + H]+ 539.97 | 1H NMR (400 MHz, Acetone-d6) δ 10.39 (s, 1H), 9.65 (s, 1H), 7.20-7.12 (m, 1H), 7.12-6.99 (m, 3H), 6.95-6.87 (m, 2H), 6.82 (t, J = 7.5 Hz, 1H), 6.54 (dd, J = 7.7, 0.7 Hz, 1H), 5.55 (dd, J = 9.1, 5.7 Hz, 1H), 5.20 (t, J = 8.2 Hz, 1H), 4.29 (d, J = 10.7 Hz, 1H), 3.99 (d, J = 10.6 Hz, 1H), 3.96 (s, 3H), 3.45 (s, 3H), 2.81-2.63 (m, 2H), 2.05-1.98 (m, 1H), 1.96-1.90 (m, 1H), 1.88-1.79 (m, 3H), 1.67-1.58 (m, 2H), 1.52-1.45 (m, 2H), 1.31-1.14 (m, 2H). |
| 107 | 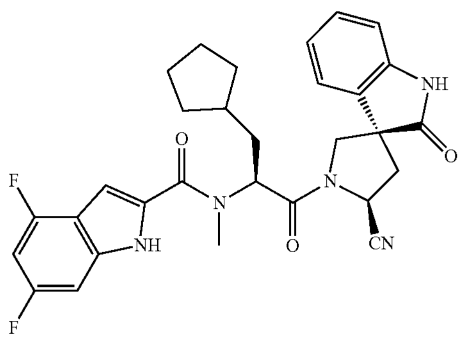 [SMILES: CN(C(=O)c1cc2c(F)cc(F)cc2[nH]1)[C@@H](CC1CCCC1)C(=O)N1C[C@]2(C[C@H]1C#N)C(=O)Nc1ccccc12] | [M + H]+ 545.95 | 1H NMR (400 MHz, Acetone-d6) δ 10.80 (s, 1H), 9.67 (s, 1H), 7.08 (dd, J = 9.4, 2.0 Hz, 1H), 7.05-6.97 (m, 2H), 6.96 (s, 1H), 6.91 (d, J = 7.7 Hz, 1H), 6.80 (dd, J = 13.7, 6.1 Hz, 1H), 6.77-6.68 (m, 1H), 5.55 (dd, J = 9.1, 5.7 Hz, 1H), 5.21 (t, J = 8.3 Hz, 1H), 4.29 (d, J = 10.7 Hz, 1H), 3.98 (d, J = 10.6 Hz, 1H), 3.46 (s, 3H), 2.75-2.64 (m, 2H), 2.06-1.99 (m, 1H), 1.99-1.89 (m, 1H), 1.83 (p, J = 6.3 Hz, 3H), 1.63 (q, J = 6.9, 5.8 Hz, 2H), 1.51 (dt, J = 14.5, 5.3 Hz, 2H), 1.32-1.11 (m, 2H). |
| 108 | 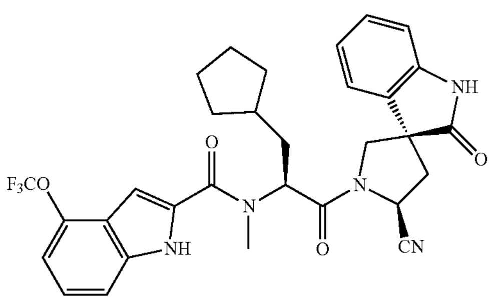 [SMILES: CN(C(=O)c1cc2c(OC(F)(F)F)cccc2[nH]1)[C@@H](CC1CCCC1)C(=O)N1C[C@]2(C[C@H]1C#N)C(=O)Nc1ccccc12] | [M − H]− 592.00 | 1H NMR (400 MHz, Acetone-d6) δ 10.82 (s, 1H), 9.65 (s, 1H), 7.50 (d, J = 8.3 Hz, 1H), 7.28 (t, J = 8.0 Hz, 1H), 7.07-6.93 (m, 4H), 6.87 (d, J = 7.7 Hz, 1H), 6.78 (t, J = 7.5 Hz, 1H), 5.54 (dd, J = 9.1, 5.9 Hz, 1H), 5.19 (t, J = 8.2 Hz, 1H), 4.25 (d, J = 10.7 Hz, 1H), 3.98 (d, J = 10.6 Hz, 1H), 2.72-2.62 (m, 2H), 1.99 (dd, J = 8.9, 5.1 Hz, 1H), 1.92 (dt, J = 13.6, 6.3 Hz, 1H), 1.86-1.76 (m, 3H), 1.64-1.56 (m, 2H), 1.53-1.43 (m, 2H), 1.27-1.16 (m, 2H). |
| 109 | 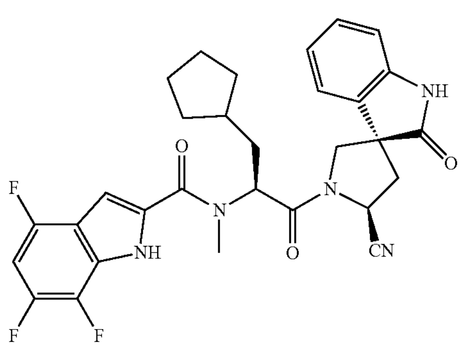 [SMILES: CN(C(=O)c1cc2c(F)cc(F)c(F)c2[nH]1)[C@@H](CC1CCCC1)C(=O)N1C[C@]2(C[C@H]1C#N)C(=O)Nc1ccccc12] | [M − H]− 561.99 | 1H NMR (400 MHz, Acetone-d6) δ 11.10 (s, 1H), 9.60 (s, 1H), 6.98-6.91 (m, 2H), 6.84 (tt, J = 9.0, 4.0 Hz, 3H), 6.74 (t, J = 7.5 Hz, 1H), 5.45 (dd, J = 9.0, 5.8 Hz, 1H), 5.14 (t, J = 8.3 Hz, 1H), 4.17 (d, J = 10.7 Hz, 1H), 3.91 (d, J = 10.6 Hz, 1H), 3.36 (s, 3H), 2.65-2.55 (m, 2H), 1.97-1.91 (m, 1H), 1.91-1.83 (m, 1H), 1.80-1.72 (m, 3H), 1.59-1.51 (m, 2H), 1.49-1.38 (m, 2H), 1.24-1.09 (m, 2H). |

| Example # | Structure | MS | NMR |
|---|---|---|---|
| 110 | 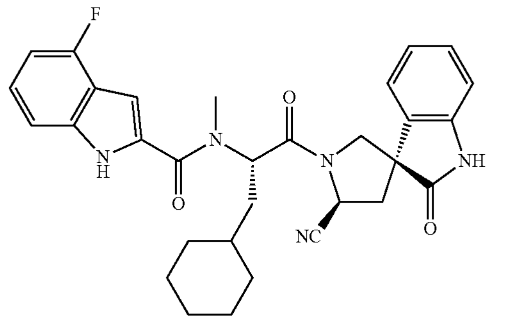 [SMILES: CN(C(=O)c1cc2c(F)cccc2[nH]1)[C@@H](CC1CCCCC1)C(=O)N1C[C@]2(C[C@H]1C#N)C(=O)Nc1ccccc12] | [M + Na]+ 564.20 | 1H NMR (400 MHz, Acetone-d6) δ 10.73 (s, 1H), 9.67 (s, 1H), 7.33 (d, J = 8.2 Hz, 1H), 7.22 (td, J = 8.0, 5.2 Hz, 1H), 7.04 (d, J = 7.9 Hz, 2H), 6.99-6.89 (m, 2H), 6.91-6.75 (m, 2H), 5.62 (dt, J = 9.5, 4.6 Hz, 1H), 5.21 (t, J = 8.2 Hz, 1H), 4.27 (d, J = 10.6 Hz, 1H), 3.99 (d, J = 10.6 Hz, 1H), 3.47 (s, 3H), 2.79-2.62 (m, 2H), 1.87 (dddd, J = 38.4, 18.2, 9.6, 4.4 Hz, 4H), 1.76-1.56 (m, 3H), 1.42-0.82 (m, 6H). |
| 111 | 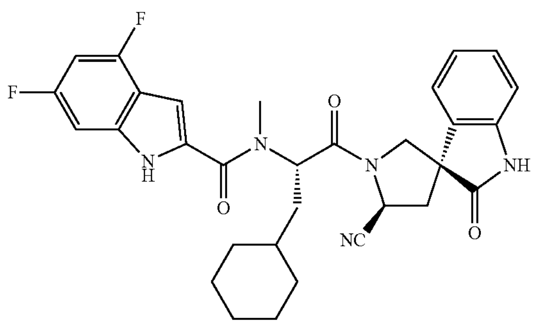 [SMILES: CN(C(=O)c1cc2c(F)cc(F)cc2[nH]1)[C@@H](CC1CCCCC1)C(=O)N1C[C@]2(C[C@H]1C#N)C(=O)Nc1ccccc12] | [M − H]− 558.26 | 1H NMR (400 MHz, Acetone-d6) δ 10.83 (s, 1H), 9.68 (s, 1H), 7.17-6.93 (m, 4H), 6.91 (d, J = 7.7 Hz, 1H), 6.82 (t, J = 7.5 Hz, 1H), 6.75 (td, J = 10.3, 2.1 Hz, 1H), 5.71-5.56 (m, 1H), 5.21 (t, J = 8.3 Hz, 1H), 4.28 (d, J = 10.7 Hz, 1H), 3.99 (d, J = 10.6 Hz, 1H), 3.47 (s, 3H), 2.81-2.63 (m, 2H), 1.98-1.78 (m, 4H), 1.75-1.54 (m, 3H), 1.37-0.84 (m, 6H). |
| 112 | 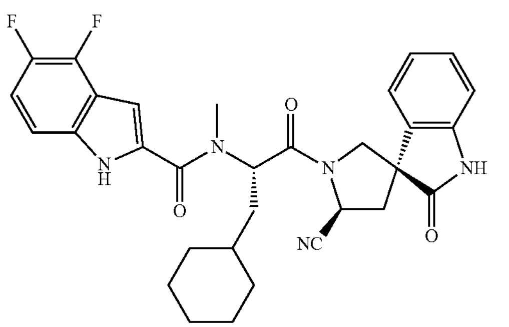 [SMILES: CN(C(=O)c1cc2c(F)c(F)ccc2[nH]1)[C@@H](CC1CCCCC1)C(=O)N1C[C@]2(C[C@H]1C#N)C(=O)Nc1ccccc12] | [M + H]+ 560.15 | 1H NMR (400 MHz, Acetone-d6) δ 10.80 (s, 1H), 9.68 (s, 1H), 7.31 (dd, J = 9.0, 3.5 Hz, 1H), 7.20 (ddd, J = 11.2, 8.9, 7.5 Hz, 1H), 7.13-6.95 (m, 3H), 6.91 (d, J = 7.7 Hz, 1H), 6.84 (t, J = 7.6 Hz, 1H), 5.66-5.49 (m, 1H), 5.21 (t, J = 8.2 Hz, 1H), 4.26 (d, J = 10.7 Hz, 1H), 3.99 (d, J = 10.6 Hz, 1H), 3.47 (s, 3H), 2.79-2.64 (m, 2H), 1.94-1.76 (m, 4H), 1.76-1.55 (m, 3H), 1.38-0.89 (m, 6H). |
| 113 | 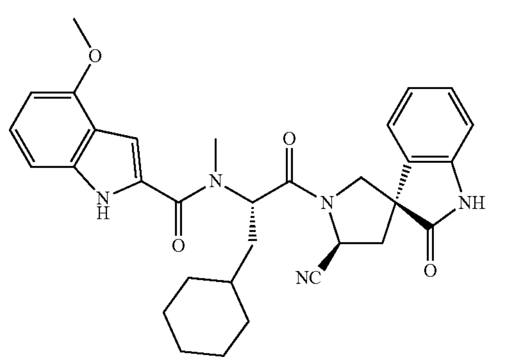 [SMILES: COc1cccc2[nH]c(C(=O)N(C)[C@@H](CC3CCCCC3)C(=O)N3C[C@]4(C[C@H]3C#N)C(=O)Nc3ccccc34)cc12] | [M − H]− 552.08 | 1H NMR (400 MHz, Methanol-d4) δ 7.16 (t, J = 8.0 Hz, 1H), 7.06 (t, J = 7.7 Hz, 1H), 7.02-6.94 (m, 2H), 6.93-6.80 (m, 3H), 6.53 (d, J = 7.7 Hz, 1H), 5.54 (m, 1H), 5.18 (t, J = 7.9 Hz, 1H), 4.61 (s, 0H), 4.20 (d, J = 10.7 Hz, 1H), 3.96 (s, 3H), 3.95 (d, J = 2.8 Hz, 1H), 3.40 (s, 3H), 2.70 (dd, J = 12.0, 6.0 Hz, 1H), 2.67 (m, 1H), 1.86-1.67 (m, 7H), 1.25-0.93 (m, 6H). |

|Example #|Structure|MS|NMR|
|---|---|---|---|
|114| 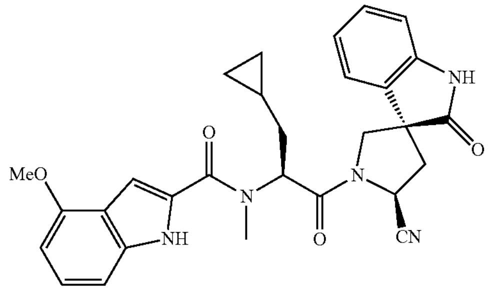 [SMILES: COc1cccc2[nH]c(C(=O)N(C)[C@@H](CC3CC3)C(=O)N3C[C@]4(C[C@H]3C#N)C(=O)Nc3ccccc34)cc12] |[M + Na]+ 534.21|1H NMR (500 MHz, Chloroform-d) δ 8.98 (s, 1H), 8.27 (s, 1H), 7.20 (t, J = 8.0 Hz, 1H), 7.10-7.04 (m, 1H), 7.02-6.88 (m, 2H), 6.88-6.76 (m, 3H), 6.50 (d, J = 7.8 Hz, 1H), 5.42 (t, J = 7.5 Hz, 1H), 5.02 (t, J = 8.5 Hz, 1H), 4.56 (d, J = 10.5 Hz, 1H), 4.03 (d, J = 10.5 Hz, 1H), 3.96 (s, 3H), 3.51 (s, 3H), 2.85 (dd, J = 13.2, 8.6 Hz, 1H), 2.52 (ddd, J = 13.2, 8.3, 1.2 Hz, 1H), 1.92 (tq, J = 13.8, 7.4 Hz, 2H), 0.73 (qq, J = 7.6, 5.2, 3.8 Hz, 1H), 0.64-0.43 (m, 2H), 0.20 (ddt, J = 14.6, 9.0, 4.7 Hz, 2H).|
|115| 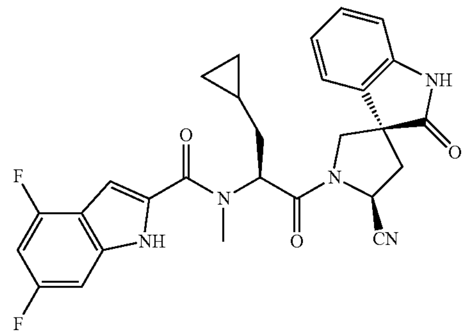 [SMILES: CN(C(=O)c1cc2c(F)cc(F)cc2[nH]1)[C@@H](CC1CC1)C(=O)N1C[C@]2(C[C@H]1C#N)C(=O)Nc1ccccc12] |[M + Na]+ 540.18|1H NMR (400 MHz, Chloroform-d) δ 9.38 (s, 1H), 8.51 (s, 1H), 7.26 (s, 1H), 7.08 (td, J = 7.4, 6.5, 2.1 Hz, 1H), 6.91-6.74 (m, 5H), 6.62 (td, J = 10.0, 2.0 Hz, 1H), 5.39 (t, J = 7.6 Hz, 1H), 5.05 (t, J = 8.4 Hz, 1H), 4.46 (d, J = 10.4 Hz, 1H), 4.04 (d, J = 10.4 Hz, 1H), 3.50 (s, 3H), 2.85 (dd, J = 13.3, 8.3 Hz, 1H), 2.53 (dd, J = 13.3, 8.4 Hz, 1H), 1.92 (h, J = 6.6 Hz, 2H), 0.88-0.66 (m, 1H), 0.66-0.45 (m, 2H), 0.21 (p, J = 4.5 Hz, 2H).|
|116| 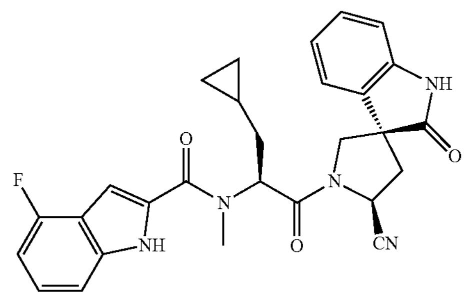 [SMILES: CN(C(=O)c1cc2c(F)cccc2[nH]1)[C@@H](CC1CC1)C(=O)N1C[C@]2(C[C@H]1C#N)C(=O)Nc1ccccc12] |[M + Na]+ 522.19| |
|117| 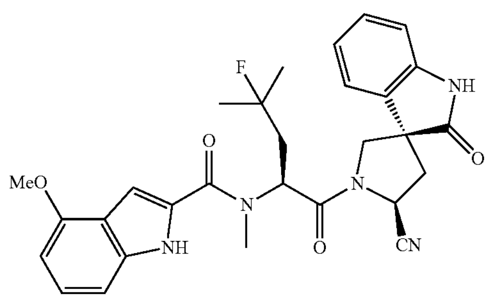 |[M + Na] 554.23|1H NMR (400 MHz, Chloroform-d) δ 9.32 (s, 1H), 9.03 (s, 1H), 7.18 (t, J = 8.0 Hz, 1H), 7.05-6.86 (m, 3H), 6.79 (d, J = 7.8 Hz, 1H), 6.68 (dd, J = 21.4, 7.4 Hz, 2H), 6.47 (d, J = 7.8 Hz, 1H), 5.75 (t, J = 6.5 Hz, 1H), 5.02 (t, J = 8.2 Hz, 1H), 4.48 (d, J = 10.7 Hz, 1H), 4.00 (d, J = 10.8 Hz, 1H), 3.95 (s, 3H), 3.47 (s, 3H), 2.82 (dd, J = 13.4, 8.1 Hz, 1H), 2.55-2.42 (m, 2H), 2.37-2.21 (m, 1H), 1.45 (s, 3H), 1.39 (s, 3H).|
|118| 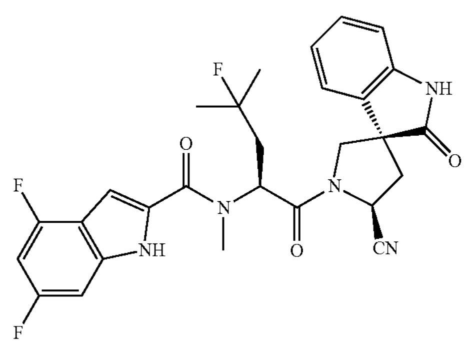 [SMILES: CN(C(=O)c1cc2c(F)cc(F)cc2[nH]1)[C@@H](CC(C)(C)F)C(=O)N1C[C@]2(C[C@H]1C#N)C(=O)Nc1ccccc12] |[M + Na] 560.19| |

Example 119

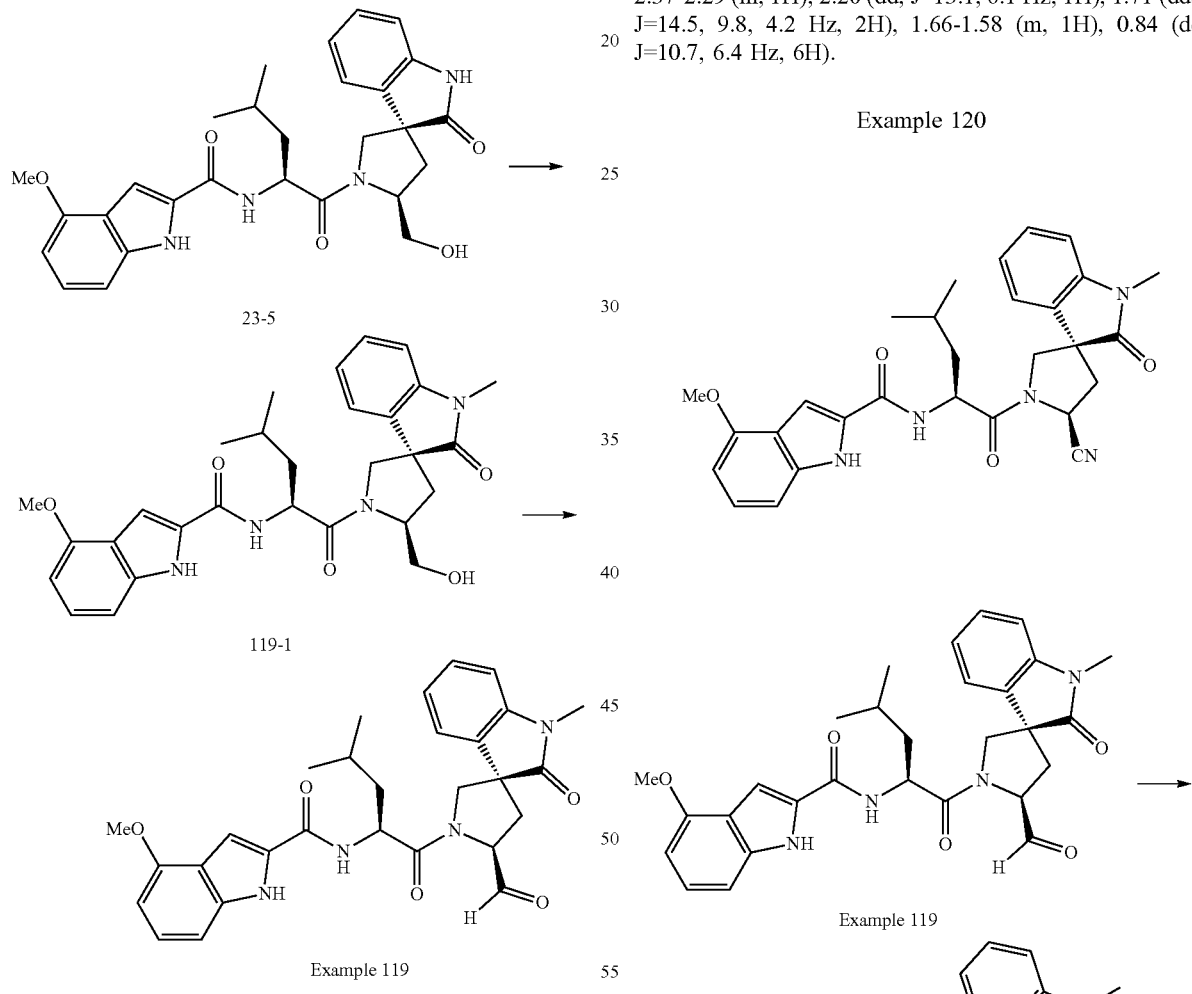

Step 1

To a solution of compound (23-5) (64 mg, 0.127 mmol) in dry acetone (0.634 mL) was added K$_2$CO$_3$ (26.3 mg, 0.190 mmol) and dimethyl sulfate (18.04 µL, 0.190 mmol) at rt. The reaction mixture was then heated and refluxed for 2 hrs. After 2 hrs, another portion of dimethyl sulfate (6.0 µL, 0.06 mmol) was added and the mixture was heated for another 3 hrs. The reaction mixture was concentrated to dryness. The residue was diluted with EtOAc, washed with water, brine, dried, and concentrated. Purification of the residue by silica gel chromatography with 0-50% acetone/cyclohexane provided compound (119-1) (53 mg, 81% yield). LC-MS, ES+: 519.14 [M+H]$^+$.

Step 2

To a solution of compound (119-1) (51 mg, 0.098 mmol) in dry DCM (0.98 mL) at 0° C. was added Dess-Martin periodinane (62.6 mg, 0.148 mmol). The mixture was stirred at 0° C. for 3 hrs. Purification of the crude reaction mixture on silica gel chromatography with 0-55% EtOAc/cyclohexane provided Example 119 (28 mg, 55% yield). LC-MS, ES+: 517.06 [M+H]$^+$. $^1$H NMR (400 MHz, Acetone-d$_6$) δ 10.52 (s, 1H), 9.52 (d, J=1.9 Hz, 1H), 7.75-7.69 (m, 1H), 7.23-7.16 (m, 3H), 7.03-6.95 (m, 2H), 6.92-6.85 (m, 2H), 6.40 (dd, J=7.2, 1.2 Hz, 1H), 4.84 (ddd, J=9.7, 8.3, 4.8 Hz, 1H), 4.54 (ddd, J=9.2, 6.1, 2.0 Hz, 1H), 4.12 (d, J=10.4 Hz, 1H), 3.96 (d, J=10.4 Hz, 1H), 3.79 (s, 3H), 3.07 (s, 3H), 2.37-2.29 (m, 1H), 2.20 (dd, J=13.1, 6.1 Hz, 1H), 1.71 (ddd, J=14.5, 9.8, 4.2 Hz, 2H), 1.66-1.58 (m, 1H), 0.84 (dd, J=10.7, 6.4 Hz, 6H).

Example 120

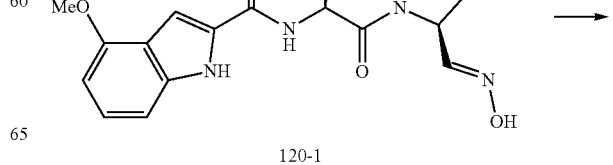

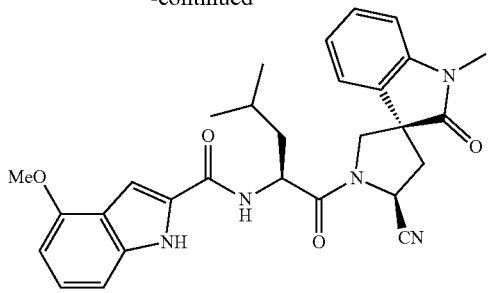

Example 120

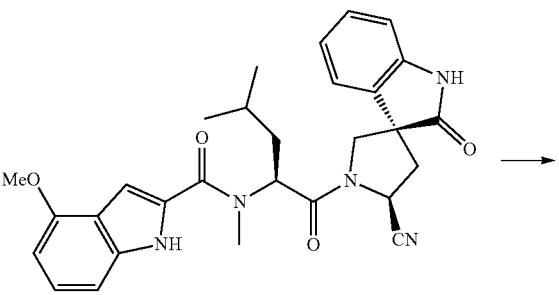

Example 42

Step 1

To a solution of Example 119 (24 mg, 0.046 mmol) in dry DMSO (0.186 mL) was added hydroxylamine hydrochloride (4.36 mg, 0.063 mmol). After stirring at rt for 1 h, the reaction mixture was diluted with EtOAc, washed with water (2×), brine, dried, and concentrated to provide the crude oxime intermediate (118-1) (21 mg), which was directly used in the next step. LC-MS, ES+: 532.13 [M+H]+.

Step 2

To a solution of the crude oxime intermediate (120-1) (21 mg, 0.046 mmol) in dry acetonitrile (0.79 mL) was added Cu(OAc)$_2$ (1.4 mg, 7.9 μmol). The reaction mixture was heated at 70° C. for 1 h and concentrated. Purification of the residue by silica gel chromatography using 0 to 50% acetone/cyclohexane afforded Example 120 (8 mg, 40% yield). LC-MS, ES+: 514.09 [M+H]+. $^1$H NMR (400 MHz, Acetone-d$_6$) δ 10.60 (s, 1H), 7.88 (d, J=8.2 Hz, 1H), 7.35 (dd, J=2.3, 0.8 Hz, 1H), 7.29 (td, J=7.7, 1.2 Hz, 1H), 7.20-7.08 (m, 3H), 7.02 (d, J=7.8 Hz, 1H), 6.95 (td, J=7.6, 1.0 Hz, 1H), 6.55 (dd, J=7.4, 1.0 Hz, 1H), 5.17 (t, J=8.3 Hz, 1H), 4.91 (ddd, J=9.8, 8.2, 4.6 Hz, 1H), 4.34 (d, J=10.3 Hz, 1H), 4.05 (d, J=10.4 Hz, 1H), 3.95 (s, 3H), 3.24 (s, 3H), 2.70 (dd, J=8.3, 3.9 Hz, 2H), 1.85 (ddd, J=12.7, 9.4, 4.7 Hz, 2H), 1.73 (dt, J=9.4, 5.3 Hz, 1H), 0.99 (dd, J=15.9, 6.4 Hz, 6H).

Example 121

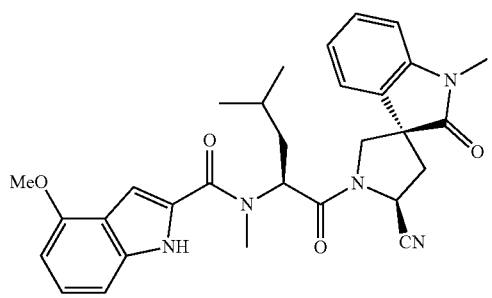 [SMILES: COc1cccc2[nH]c(C(=O)N(C)[C@@H](CC(C)C)C(=O)N3C[C@]4(C[C@H]3C#N)C(=O)N(C)c3ccccc34)cc12]

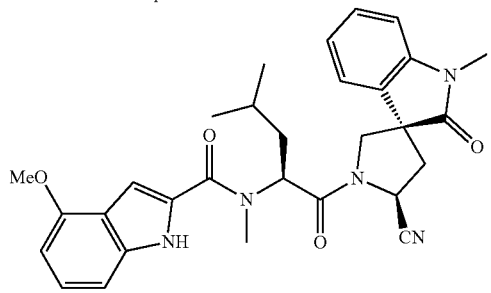

Example 121

Step 1

To a solution of Example 42 (30 mg, 0.058 mmol) in dry acetone (0.29 mL) was added K$_2$CO$_3$ (12.11 mg, 0.088 mmol) and dimethyl sulfate (8.31 μL, 0.088 mmol) at rt. The reaction mixture was then heated to reflux for 3 hrs. The mixture was then concentrated to remove acetone, diluted with EtOAc, washed with water and brine, dried and concentrated. Purification of the residue on silica gel with 0-50% acetone/cyclohexane provided Example 121 (16 mg, 81% yield). LC-MS, ES−: 526.03 [M−1]. $^1$H NMR (400 MHz, Acetone-d$_6$) δ 10.36 (s, 1H), 7.20-7.10 (m, 2H), 7.10-7.03 (m, 2H), 7.00-6.91 (m, 2H), 6.87 (t, J=7.5 Hz, 1H), 6.55 (d, J=7.7 Hz, 1H), 5.57 (dd, J=9.6, 5.6 Hz, 1H), 5.20 (t, J=8.1 Hz, 1H), 4.25 (d, J=10.7 Hz, 1H), 4.00 (d, J=10.6 Hz, 1H), 3.97 (s, 3H), 3.45 (s, 3H), 3.22 (s, 3H), 2.77-2.63 (m, 2H), 1.93 (ddd, J=14.4, 9.6, 5.1 Hz, 1H), 1.77 (ddd, J=14.2, 8.7, 5.6 Hz, 1H), 1.62 (dtd, J=8.6, 6.6, 5.0 Hz, 1H), 0.98 (dd, J=23.1, 6.6 Hz, 6H).

Example 122

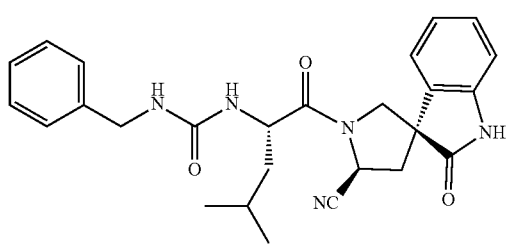 [SMILES: CC(C)C[C@H](NC(=O)NCc1ccccc1)C(=O)N1C[C@]2(C[C@H]1C#N)C(=O)Nc1ccccc12]

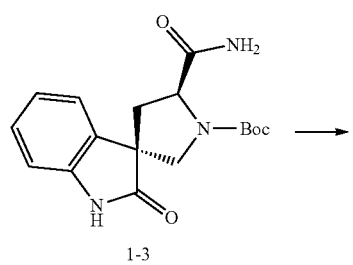

1-3

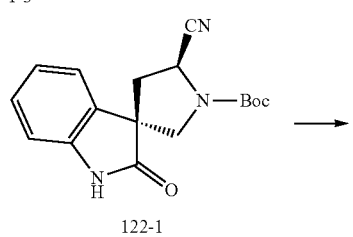

122-1

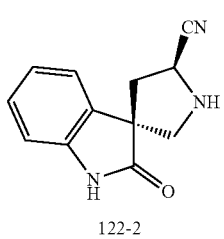

122-2

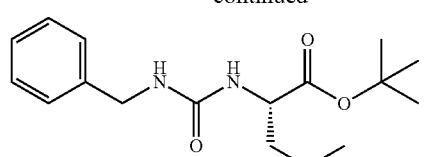

122-3

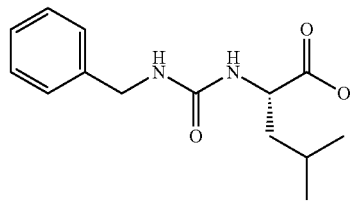

122-4

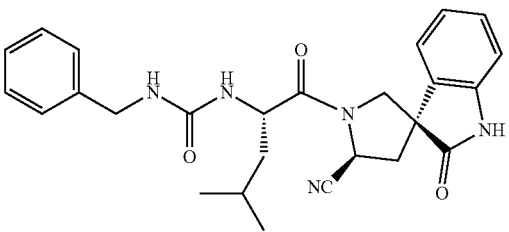

Example 122

Step 1

Compound (1-3) (425 mg, 1.38 mmol) was suspended in DCM (5 mL). Et$_3$N (0.54 mL, 3.9 mmol) and TFAA (0.36 mL, 2.57 mmol) were added dropwise. The mixture was stirred at rt for 30 mins. The 2nd portion of Et$_3$N (0.2 mL) was added, followed by TFAA (0.12 mL). The mixture was stirred at rt for 20 min and concentrated. Purification of the residue on silica gel afforded compound (122-1) (320 mg, 80%). ESI-MS m/z=314.05 [M+H]*.

Step 2

Lutidine (0.18 mL, 1.05 mmol) in DCM (1 mL) was cooled to 0° C. TMSOTf (0.2 mL, 0.95 mmol) was added and the mixture was stirred at 0° C. for 5 mins. In another tube, compound (122-1) (100 mg, 0.32 mmol) in DCM (1 mL) was cooled to 0° C. The TMSOTf/lutidine solution (1.9 mL) was added dropwise and the resulting mixture was stirred at 0° C. for 20 mins.

Aq. NaHCO$_3$ (4 mL) was added and the mixture was stirred for 10 min and extracted with DCM (2×). The combined organic layer was washed with aq. CsF (0.5 M) and brine, dried with Na$_2$SO$_4$, and concentrated to afford compound (122-2) (68 mg, 100%) as a yellow solid. ESI-MS m/z=213.88 [M+H]$^+$.

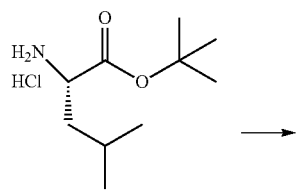

Step 3

Leucine t-butyl ester hydrochloride salt (1.0 g, 4.47 mmol) and benzyl isocyanate (595 mg, 4.47 mmol) was mixed in DCM (6 mL). At 0° C. TEA (1.25 mL, 8.95 mmol) was added. The mixture was stirred at rt for 3 h and concentrated. Purification of the residue on silica provided the compound (122-3) (1.5 g) as a colorless syrup. ESI-MS m/z=321.07 [M+H]$^+$.

Step 4

To a solution of compound (122-3) (1.5 g) in DCM (12 mL) was added TFA (1.27 mL, 23 mmol). The mixture was stirred at rt overnight and concentrated. Purification of the residue on silica provided compound (122-4) (301 mg, 25% for two steps) as light yellow oil. ESI-MS m/z=265.02 [M+H]$^+$.

Step 5

To a solution of compound (122-2) (20 mg, 0.094 mmol) and compound (122-4) (32 mg, 1.122 mol) in DMF (1 mL) was added TCFH (39 mg, 0.14 mmol) and methyl imidazole (23 mg, 0.38 mmol). The reaction was stirred at rt for 15 mins, diluted with EtOAc, and washed with water and brine. The organic layer was dried over Na$_2$SO$_4$ and concentrated. Purification of the residue on silica provided Example 122 (30 mg, 70%) as a yellow solid. ESI-MS m/z=460.31 [M+H]$^+$; $^1$H NMR (400 MHz, Chloroform-d) δ 9.06 (br, 1H), 7.21 (d, J=4.3 Hz, 4H), 7.18-7.11 (m, 1H), 7.06 (t, J=7.8 Hz, 1H), 6.85 (d, J=7.6 Hz, 1H), 6.83-6.73 (m, 1H), 6.65 (d, J=7.9 Hz, 1H), 6.03 (br, 1H), 5.61 (br, 1H), 4.63 (d, J=7.8 Hz, 1H), 4.45 (t, J=8.3 Hz, 1H), 4.33 (d, J=14.6 Hz, 1H), 4.20 (dd, J=20.2, 12.6 Hz, 2H), 3.85 (d, J=10.3 Hz, 1H), 2.72-2.58 (m, 1H), 2.24 (dd, J=13.0, 8.0 Hz, 1H), 1.80-1.46 (m, 3H), 0.98-0.81 (m, 6H).

Example 123

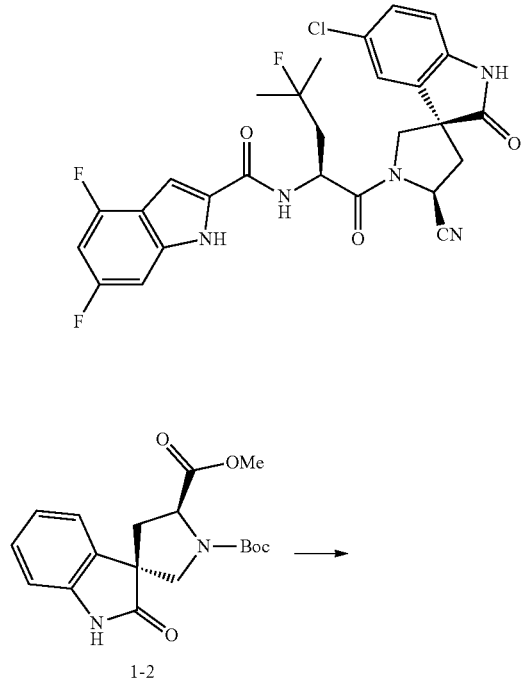

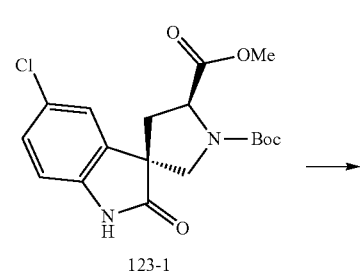

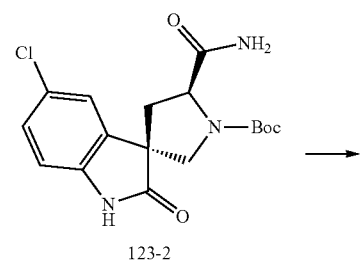

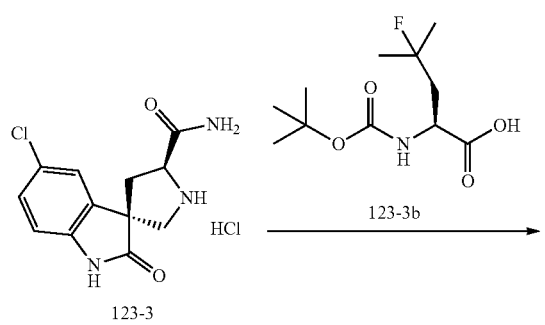

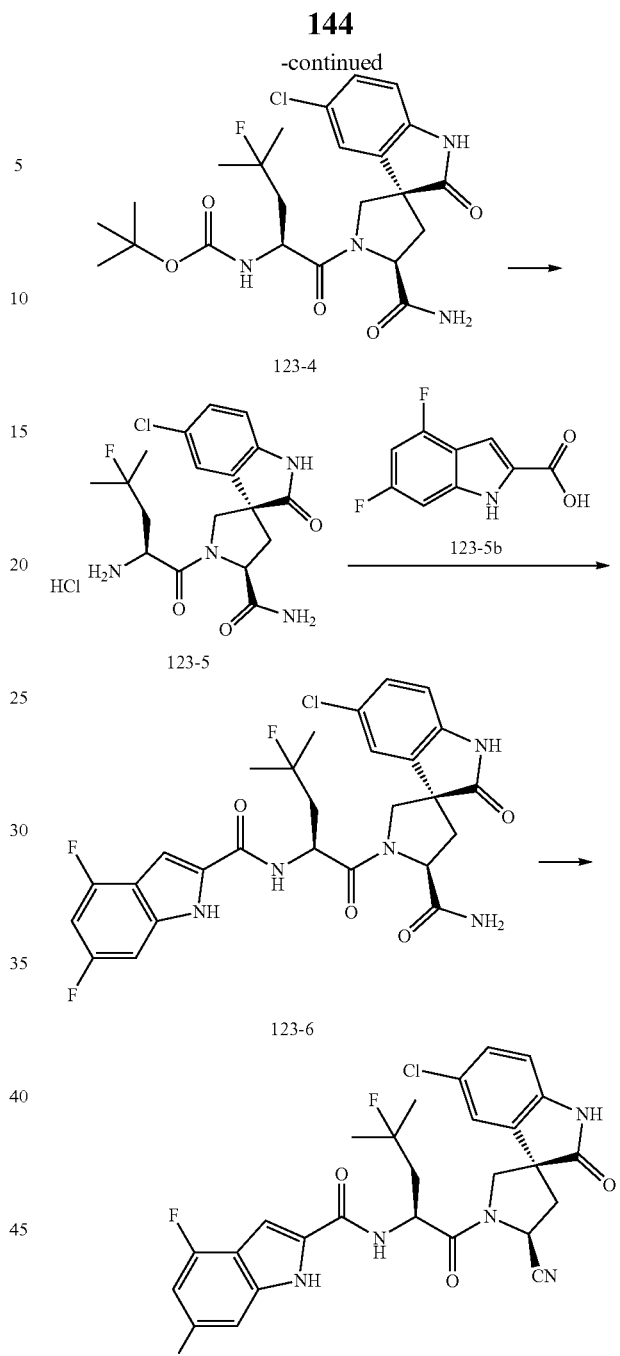

Example 123

Step 1

Compound (1-2) (5.00 g) was dissolved in acetic acid (115 mL). Sulfuryl chloride (2.09 g) was slowly added to the resulting solution at room temperature. The mixture was stirred overnight at room temperature. Then, the reaction mixture was concentrated. The crude residue was dissolved in methylene chloride (100 mL) and triethylamine (5.84 g, 8.05 mL, 4.0 equiv) was added, followed by tert-butyl dicarbonate (4.73 g, 1.5 equiv). Then, the organic layer was washed with 1M HCl (2×50 mL), then brine (100 mL), then dried over magnesium sulfate. Upon concentration, the crude residue was purified by RPHPLC, affording compound (123-1) (2.81 g, 51% yield). [M+H]$^+$, 381.1.

Step 2

Compound (123-1) (2.81 g) was dissolved in 7M methanolic ammonia (36.1 mL) in a 100 mL pressure vessel. The mixture was heated at 60° C. for 36 h. Upon concentration, the crude residue was triturated with acetonitrile to afford compound (123-2) as a colorless solid (1.92 g, 71% yield). [M+H]$^+$, 366.1.

Step 3

Compound (123-2) (1.61 g) was dissolved in 4M HCl/1,4-dioxane (22.0 mL). The resulting mixture was stirred at room temperature for 2 h. Concentration afforded compound (123-4) (1.33 g) as a white solid which was used without further purification. [M+H]$^+$, 266.1.

Step 4

Compound (123-3) (103.0 mg), compound (123-3b) (98.0 mg), and HATU (149.0 mg) were combined in a 40 mL vial equipped with a stir bar. DMF (2.27 mL) was added, followed by DIPEA (179 µL). The resulting mixture was stirred at room temperature overnight. Upon completion, the reaction mixture was diluted with ethyl acetate (50 mL), washed with 1M HCl (2×20 mL) and brine (20 mL), then dried over magnesium sulfate. Upon concentration, the crude residue was purified by silica gel column chromatography (0 to 10% MeOH/DCM) affording compound (123-4) (58.1 mg, 34% yield). [M+H]$^+$, 497.2.

Step 5

Compound (123-4) (58.1 mg) was dissolved in 4M HCl/1,4-dioxane (585 µL). The resulting mixture was stirred for 1.5 h. The reaction mixture was concentrated to afford compound (123-5) (51.0 mg) which was used in the next step without purification. [M+H]$^+$, 397.2.

Step 6

Compound (123-5) (51.0 mg), compound (121-5b) (26.7 mg), and HATU (51.5 mg) were combined in 40 mL vial equipped with a stir bar. DMF (785 µL) was added, followed by DIPEA (62 µL). The resulting mixture was stirred 2.5 h at room temperature. The reaction mixture was diluted with ethyl acetate (100 mL) and washed with 1M HCl (3×20 mL) and brine (20 mL). The organic layer was dried over magnesium sulfate then concentrated. Purification of the crude residue by silica gel column chromatography (0 to 10% MeOH/DCM) afforded compound (123-6) (26.9 mg, 40% yield). [M+H]$^+$, 576.1.

Step 7

Compound (123-6) (26.9 mg) was dissolved in a mixture of MeCN (500 µL) and water (500 µL) in a 20 mL vial. Next, 2,2-dichloroacetonitrile (56 µL) was added, followed by palladium(II) trifluoroacetate (1.5 mg). The vial was sealed and the mixture was heated at 65° C. for 2 h. Additional 2,2-dichloroacetonitrile (56 µL) and palladium(II) trifluoroacetate (1.5 mg) were added, and the mixture was heated at 70° C. for 20 min. Upon cooling to room temperature, the mixture was purified by RPHPLC to afford Example 123 as a white solid (10.0 mg, 38% yield). ESI MS m/z=558.1 [M+H]$^+$. $^1$H NMR (400 MHz, acetone-d$_6$, δ ppm): δ 10.96 (s, 1H), 9.80 (s, 1H), 8.18-8.16 (m, 1H), 7.35-7.34 (m, 1H), 7.15-7.09 (m, 3H), 6.97-6.95 (m, 1H). 6.77-6.72 (m, 1H), 5.23 (app t, J=8.2, 8.2 Hz, 1H), 5.15-5.09 (m, 1H), 4.46 (d, J=10.5 Hz, 1H), 4.06 (10.5 Hz, 1H), 2.85-2.67 (m, 2H), 2.42-2.18 (m, 2H), 1.47 (d, J$_{19F-1H}$=3.2 Hz, 3H), 1.41 (d, J$_{19F-1H}$=3.2 Hz, 3H).

Example 124

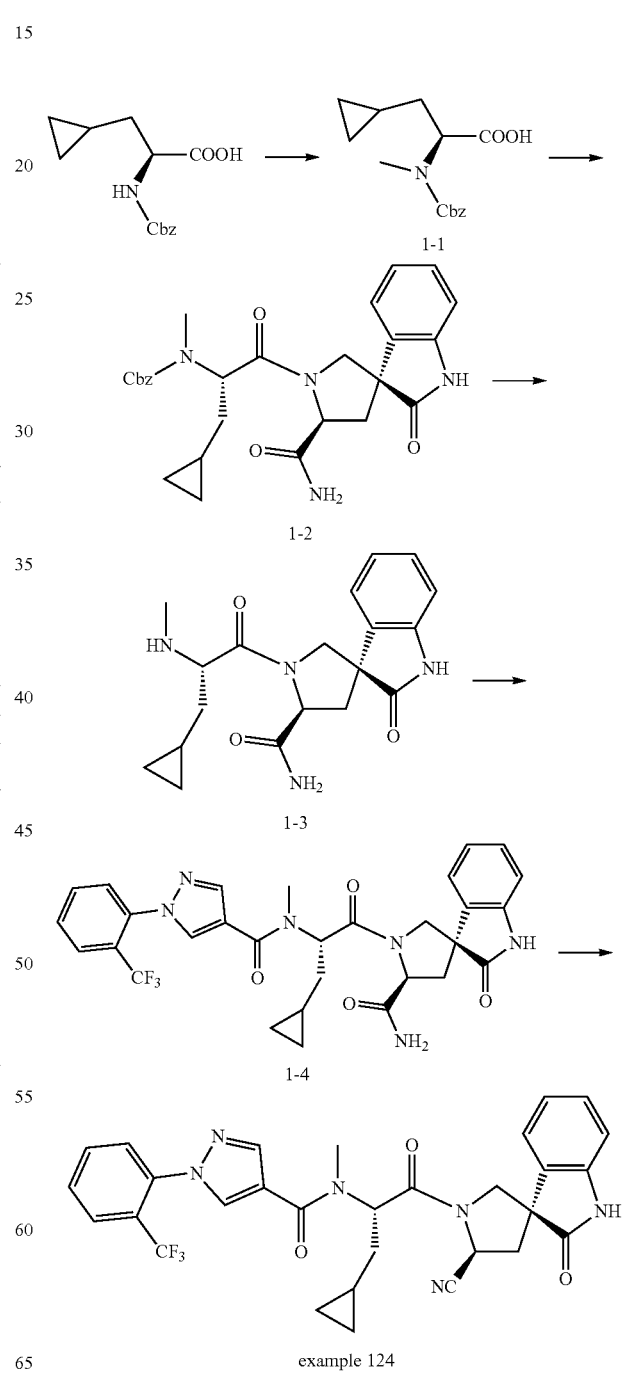

example 124

Step 1

To a mixture of (S)-2-(((benzyloxy)carbonyl)amino)-3-cyclopropylpropanoic acid (2.4 g, 9.12 mmol) and MeI (10.5 g, 72.9 mmol) in THF (30 mL) at 0° C. was added NaH (1.09 g, 27.3 mmol) portion wise and stirred at rt for 2 days. it was quenched with ice-water, extracted with MBTE twice. The aqueous layer was acidified with 1 N HCl to pH~2, extracted with EtOAc, washed with brine, dry over $Na_2SO_4$, filtered, concentrated to give the desired compound (1-1) (2.3 g, 90% yield). ESI-MS m/z=276.12 $[M-H]^-$.

Step 2

To a solution of intermediate 1-5 (5.75 g, 17.18 mmol), compound (1-1) (5.24 g, 18.9 mmol) and N-methyl morpholine (6.08 g, 60.1 mmol) in DCM/DMF (30/10 mL) was added HATU (6.55 g, 17.18 mmol) and stirred at rt for 2 h. It was quenched with water, extracted with EtOAc, washed with water, 1N HCl, sat $NaHCO_3$, brine, dry over $Na_2SO_4$, filtered, concentrated, silica gel column purification to give the desired compound (1-2) (5.94 g, 70% yield). ESI-MS m/z=489.21 $[M-H]^-$.

Step 3

A mixture of compound (1-2) (5.65 g, 11.52 mmol) and Pd—C (10%) (1.23 g, 1.15 mmol) in MeOH (30 mL) was treated with $H_2$ using a hydrogen balloon. After 1 h, it was diluted with DCM, filtered through celite, concentrated to give desired compound (1-3) (4.1 g, 100%). ESI-MS m/z=355.18 [M-H].

Step 4

A mixture of compound (1-3) (50 mg, 0.14 mmol), 1-(2-(trifluoromethyl)phenyl)-1H-pyrazole-4-carboxylic acid (35.9 mg, 0.140 mmol), N-methyl morpholine (35.5 mg, 0.35 mmol) in DCM/DMF (0.5/0.5 mL) at rt was added HATU (53 mg, 0.14 mmol) and stirred rt for 20 h. It was quenched water, extracted with EtOAc, washed with water, brine, dry over $Na_2SO_4$, filtered. concentrated, silica gel column purification to give desired compound (1-4) (60 mg, 72% yield). ESI-MS m/z=593.21 $[M-H]^-$.

Step 5

A mixture of compound (1-4) (60 mg, 0.10 mmol) and $Et_3N$ (113 µl, 0.80 mmol) in DCM (1 mL) at 0° C. was treated with TFAA (57 µl, 0.40 mmol). After 30 mins at rt, it was quenched with cold Sat. $NaHCO_3$, extracted with EtOAc, washed with 1 N HCl, Sat. $NaHCO_3$, brine, dry over $Na_2SO_4$, filtered, concentrated, silica gel column purification to give the compound of example 1 (32 mg, 55% yield) ESI-MS m/z=575.28 [M-H]. $^1$H NMR (400 MHz, Acetone-$d_6$) δ 9.50 (s, 1H), 7.86 (s, 1H), 7.80-7.74 (m, 1H), 7.70 (t, J=7.6 Hz, 1H), 7.59 (dd, J=14.9, 5.8 Hz, 2H), 7.45 (d, J=8.0 Hz, 1H), 6.95 (td, J=7.7, 1.3 Hz, 1H), 6.87 (ddd, J=7.5, 1.4, 0.7 Hz, 1H), 6.74 (dd, J=8.0, 7.0 Hz, 2H), 5.28 (t, J=7.7 Hz, 1H), 5.00 (t, J=8.3 Hz, 1H), 4.21 (d, J=10.7 Hz, 1H), 3.78 (d, J=10.6 Hz, 1H), 3.10 (s, 3H), 2.64-2.44 (m, 2H), 1.66 (dd, J=15.1, 7.7 Hz, 2H), 0.64-0.54 (m, 1H), 0.33-0.23 (m, 2H), 0.05-0.00 (m, 2H).

Example 125

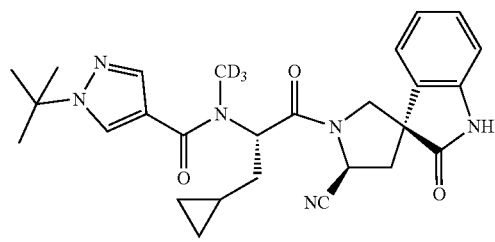 [SMILES: [2H]C([2H])([2H])N(C(=O)c1cnn(C(C)(C)C)c1)[C@@H](CC1CC1)C(=O)N1C[C@]2(C[C@H]1C#N)C(=O)Nc1ccccc12]

The compound of example 125 was prepared employing similar protocol as example 1. ESI-MS m/z=490.27 $[M-H]^-$. $^1$H NMR (400 MHz, Acetone-$d_6$) δ 9.51 (s, 1H), 7.63 (s, 1H), 7.40 (s, 1H), 7.02 (t, J=7.7 Hz, 1H), 6.88-6.82 (m, 1H), 6.77 (dd, J=14.0, 7.5 Hz, 2H), 5.27 (s, 1H), 4.99 (t, J=8.3 Hz, 1H), 4.22 (d, J=10.5 Hz, 1H), 3.77 (d, J=10.7 Hz, 1H), 2.59-2.46 (m, 2H1.65-1.56 (m, 2H), 1.39 (s, 9H), 0.62-0.54 (m, 1H), 0.34-0.25 (m, 2H), 0.06-0.00 (m, 2H).

BIOLOGICAL ACTIVITY

SARS-CoV-2 3C-like (3CL) protease fluorescence assay (FRET): Recombinant SARS-CoV-2 3CL-protease was expressed and purified. TAMRA-SITSAVLQSGFRKMK-Dabcyl-OH peptide 3CLpro substrate was synthesized. Black, low volume, round-bottom, 384 well microplates were used. In a typical assay, 0.85 µL of test compound was dissolved in DMSO then incubated with SARS-CoV-2 3CL-protease (10 nM) in 10 µL assay buffer (50 mM HEPES [pH 7.5], 1 mM DTT, 0.01% BSA, 0.01% Triton-X 100) for 30 min at RT. Next, 10 µL of 3CL-protease substrate (40 µM) in assay buffer was added and the assays were monitored continuously for 1 h in an Envision multimode plate reader operating in fluorescence kinetics mode with excitation at 540 nm and emission at 580 nm at RT. No compound (DMSO only) and no enzyme controls were routinely included in each plate. All experiments were run in duplicate. Data Analysis: SARS-CoV-2 3CL-protease enzyme activity was measured as initial velocity of the linear phase (RFU/s) and normalized to controlled samples DMSO (100% activity) and no enzyme (0% activity) to determine percent residual activity at various concentrations of test compounds (0-10 µM). Data were fitted to normalized activity (variable slope) versus concentration fit in GraphPad Prism 7 to determine $IC_{50}$. All experiments were run in duplicate, and $IC_{50}$ ranges are reported as follows: A<0.1 µM; B 0.1-1 µM; C>1 µM.

TABLE 1

Summary of Activities

| Compound | FRET $IC_{50}$ | Compound | FRET $IC_{50}$ |
|---|---|---|---|
| 1 | B | 2 | A |
| 3 | C | 4 | A |
| 5 | A | 6 | C |
| 7 | A | 8 | A |
| 9 | B | 10 | B |
| 11 | A | 12 | C |
| 13 | A | 14 | B |
| 15 | A | 16 | B |
| 17 | A | 18 | C |
| 19 | A | 20 | A |
| 21 | A | 22 | B |
| 23 | A | 24 | B |
| 25 | A | 26 | B |
| 27 | A | 28 | A |
| 29 | A | 30 | A |
| 31 | B | 32 | A |
| 33 | A | 34 | C |
| 35 | C | 36 | B |
| 37 | B | 38 | C |
| 39 | A | 40 | A |
| 41 | A | 42 | A |
| 43 | B | 44 | A |
| 45 | A | 46 | A |
| 47 | A | 48 | B |
| 49 | A | 50 | A |
| 51 | A | 52 | A |
| 53 | A | 54 | A |
| 55 | A | 56 | A |

TABLE 1-continued

Summary of Activities

| Compound | FRET IC$_{50}$ | Compound | FRET IC$_{50}$ |
|---|---|---|---|
| 57 | A | 58 | A |
| 59 | A | 60 | A |
| 61 | A | 62 | A |
| 63 | A | 64 | A |
| 65 | A | 66 | A |
| 67 | A | 68 | A |
| 69 | A | 70 | A |
| 71 | A | 72 | A |
| 73 | A | 74 | A |
| 75 | A | 76 | A |
| 77 | B | 78 | A |
| 79 | A | 80 | A |
| 81 | A | 82 | A |
| 83 | A | 84 | A |
| 85 | A | 86 | A |
| 87 | A | 88 | A |
| 89 | A | 90 | A |
| 91 | A | 92 | A |
| 93 | A | 94 | A |
| 95 | A | 96 | A |
| 97 | A | 98 | A |
| 99 | A | 100 | A |
| 101 | A | 102 | A |
| 103 | A | 104 | A |
| 105 | A | 106 | A |
| 107 | A | 108 | A |
| 109 | A | 110 | A |
| 111 | A | 112 | A |
| 113 | A | 114 | A |
| 115 | A | 116 | A |
| 117 | — | 118 | — |
| 119 | A | 120 | B |
| 121 | A | 122 | A |
| 123 | A | 124 | A |
| 125 | A | | |

229E Assay Protocol

Viral stock preparation: MRC-5 cells, (a diploid cell culture line composed of fibroblasts, originally developed from the lung tissue of a 14-week-old aborted Caucasian male fetus), were used for the culturing of 229E human corona virus (hCoV). Flasks were inoculated with hCoV-229E and viral stocks were collected once cytopathic effect (CPE) was greater than 70%. Viral stocks in Growth Media (EMEM, 1% Penn/Strep, 1% nonessential amino acids, 10% heat-inactivated FBS) plus 5% glycerol were snap frozen using liquid nitrogen and stored at −80° C. Viral stock titers were quantified by a TCID$_{50}$ (50% median tissue culture infectious dose) assay, as described elsewhere.

229E live virus assay: 384-well black cell-culture-treated plastic clear-bottom plates are used in this assay. Using an ECHO liquid dispenser, 3-fold serial dilutions of control and test compounds suspended in DMSO are added to the plate wells in duplicate in a total volume of 125 nL per well. MRC-5 cells below passage 17 are seeded into the inner 240 wells of the 384-well plate at 1,500 cells per well in a volume of 12.5 μL using Growth Media. Viral stock is then added to the wells at a multiplicity of infection (MOI) of 0.05 in a volume of 12.5 μL per well, bringing the total volume of each well to ~25 μL. Each plate has a control row of 20 wells with cells plus DMSO and virus but no compound (positive control, max CPE, minimum ATPlite signal), and a row with cells plus DMSO but no compound or virus (negative control, minimum CPE, maximum ATPlite signal), and a row with no cells or virus or compound (background plate/reagent control). The control wells with cells but no virus are given an additional 12.5 μL of growth media containing an equal quantity of glycerol as those wells receiving the viral stock in order to keep consistent in media and volume conditions. The outer 2 rows/columns of wells are filled with 30 μL of moat media (DMEM, 1% Penn/Strep) to act as a thermal and evaporative barrier around the test wells. Following addition of all components, the sides of the plates are gently tapped by hand to promote even cell distribution across the wells. Upon confirmation of cell distribution, plates are incubated at 34° C. in a CO$_2$ humidity-controlled incubator for 6 days. Following the 6-day incubation period, the plates are read using ATPlite (12.5 μL added per well), which quantifies the amount of ATP (a measure of cell health) present in each well. Assay plates are read using an Envision luminometer. These data are used to calculate the percent cell health per well relative to the negative control wells and the EC$_{50}$ of each compound is calculated using ExcelFit software and 4-parameter logistical curve fitting analysis.

All experiments were run in duplicate, and EC$_{50}$ ranges are reported as follows: A<0.1 μM; B 0.1-1 μM; C>1 μM.

TABLE 2

Summary of Activities

| Compound | 229E EC$_{50}$ | Compound | 229E EC$_{50}$ |
|---|---|---|---|
| 1 | B | 2 | B |
| 3 | C | 4 | B |
| 5 | B | 6 | — |
| 7 | — | 8 | — |
| 9 | — | 10 | — |
| 11 | A | 12 | B |
| 13 | A | 14 | A |
| 15 | A | 16 | B |
| 17 | A | 18 | B |
| 19 | A | 20 | A |
| 21 | A | 22 | — |
| 23 | A | 24 | A |
| 25 | A | 26 | A |
| 27 | A | 28 | A |
| 29 | A | 30 | A |
| 31 | B | 32 | B |
| 33 | C | 34 | C |
| 35 | C | 36 | B |
| 37 | B | 38 | — |
| 39 | C | 40 | B |
| 41 | C | 42 | A |
| 43 | A | 44 | A |
| 45 | A | 46 | A |
| 47 | B | 48 | B |
| 49 | A | 50 | A |
| 51 | A | 52 | A |
| 53 | — | 54 | — |
| 55 | — | 56 | — |
| 57 | — | 58 | B |
| 59 | C | 60 | B |
| 61 | C | 62 | C |
| 63 | C | 64 | C |
| 65 | A | 66 | A |
| 67 | — | 68 | — |
| 69 | — | 70 | — |
| 71 | — | 72 | — |
| 73 | — | 74 | — |
| 75 | — | 76 | — |
| 77 | — | 78 | — |
| 79 | — | 80 | — |
| 81 | — | 82 | A |
| 83 | — | 84 | — |
| 85 | A | 86 | A |
| 87 | A | 88 | A |
| 89 | B | 90 | B |
| 91 | A | 92 | A |
| 93 | A | 94 | — |
| 95 | B | 96 | B |
| 97 | C | 98 | B |
| 99 | — | 100 | B |
| 101 | — | 102 | C |

151

TABLE 2-continued

Summary of Activities

| Compound | 229E EC$_{50}$ | Compound | 229E EC$_{50}$ |
|---|---|---|---|
| 103 | B | 104 | A |
| 105 | A | 106 | — |
| 107 | — | 108 | — |
| 109 | — | 110 | — |
| 111 | — | 112 | — |
| 113 | A | 114 | A |
| 115 | A | 116 | A |
| 117 | — | 118 | — |
| 119 | B | 120 | C |
| 121 | B | 122 | B |
| 123 | A | 124 | A |
| 125 | A | | |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by the formula

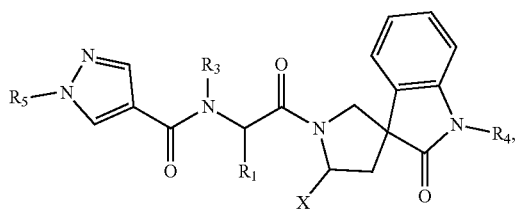

wherein

X is CN;

R$_3$ is hydrogen, methyl or CD$_3$;

R$_1$ is C$_1$-C$_8$-alkyl, arylalkyl or C$_3$-C$_6$-cycloalkyl-C$_1$-C$_4$-alkyl;

R$_4$ is hydrogen; and

R$_5$ is C$_1$-C$_6$-alkyl or phenyl optionally substituted with 1 to 3 substituents independently selected from halogen, C$_1$-C$_6$-alkyl and C$_1$-C$_6$-haloalkyl.

152

2. The compound of claim 1, wherein the compound is

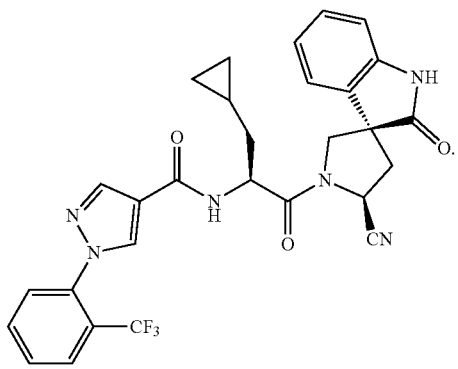 [SMILES: N#C[C@@H]1C[C@@]2(CN1C(=O)[C@H](CC1CC1)NC(=O)c1cnn(-c3ccccc3C(F)(F)F)c1)C(=O)Nc1ccccc12]

3. The compound of claim 1, wherein the compound is

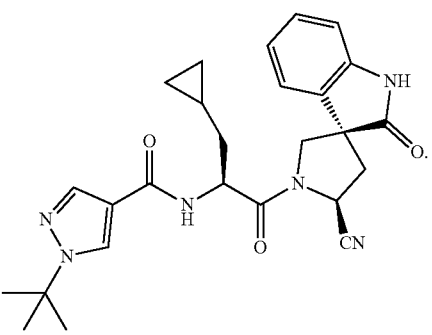 [SMILES: CC(C)(C)n1cc(C(=O)N[C@@H](CC2CC2)C(=O)N2C[C@]3(C[C@H]2C#N)C(=O)Nc2ccccc23)cn1]

4. A pharmaceutical composition comprising the compound of claim 1 and a pharmaceutically acceptable carrier or excipient.

5. A pharmaceutical composition comprising the compound of claim 2 and a pharmaceutically acceptable carrier or excipient.

6. A pharmaceutical composition comprising the compound of claim 3 and a pharmaceutically acceptable carrier or excipient.

7. A method of treating a coronavirus infection in a subject in need thereof, comprising administering to the subject a therapeutically effective amount of the compound of claim 1.

8. A method of treating a coronavirus infection in a subject in need thereof, comprising administering to the subject a therapeutically effective amount of the compound of claim 2.

9. A method of treating a coronavirus infection in a subject in need thereof, comprising administering to the subject a therapeutically effective amount of the compound of claim 3.

* * * * *